United States Patent
Wan et al.

(10) Patent No.: US 9,273,054 B2
(45) Date of Patent: Mar. 1, 2016

(54) SUBSTITUTED PYRIMIDO[1,6-A]PYRIMIDINES AS LP-PLA$_2$ INHIBITORS

(75) Inventors: Zehong Wan, Shanghai (CN); Kai Long, Shanghai (CN); Xiaomin Zhang, Shanghai (CN); Haihua Yu, Shanghai (CN)

(73) Assignee: Glaxo Group Limited, Brentford, Middlesex (GB)

( * ) Notice: Subject to any disclaimer, the term of this patent is extended or adjusted under 35 U.S.C. 154(b) by 106 days.

(21) Appl. No.: 14/234,687

(22) PCT Filed: Jul. 25, 2012

(86) PCT No.: PCT/EP2012/064598
§ 371 (c)(1),
(2), (4) Date: Jan. 24, 2014

(87) PCT Pub. No.: WO2013/014185
PCT Pub. Date: Jan. 31, 2013

(65) Prior Publication Data
US 2014/0179716 A1    Jun. 26, 2014

(30) Foreign Application Priority Data

Jul. 27, 2011  (WO) ............... PCT/CN2011/077702

(51) Int. Cl.
*A61K 31/519* (2006.01)
*C07D 239/70* (2006.01)
*C07D 487/04* (2006.01)

(52) U.S. Cl.
CPC .................................... *C07D 487/04* (2013.01)

(58) Field of Classification Search
CPC ........................... A61K 31/519; C07D 239/70
USPC ....................................... 514/259.5; 544/282
See application file for complete search history.

(56) References Cited

U.S. PATENT DOCUMENTS

2013/0030012 A1*  1/2013  Long et al. ................. 514/259.5

FOREIGN PATENT DOCUMENTS

WO    WO 03/087088    10/2003
WO    WO 2008/048867   4/2008

OTHER PUBLICATIONS

Jordan, V. C. Nature Reviews: Drug Discovery, 2, 2003, 205.*
Hackam, et al. JAMA, 296(14), 2006, 1731-1732.*
PCT Search Report for PCT/EP2012/064598 dated Sep. 13, 2012.

* cited by examiner

*Primary Examiner* — Douglas M Willis
(74) *Attorney, Agent, or Firm* — Fang Qian; William R. Majarian

(57) ABSTRACT

The present invention relates to novel compounds that inhibit Lp-PLA$_2$ activity, processes for their preparation, to compositions containing them and to their use in the treatment of diseases associated with the activity of Lp-PLA$_2$, for example atherosclerosis, Alzheimer's disease.

12 Claims, No Drawings

SUBSTITUTED PYRIMIDO[1,6-A]PYRIMIDINES AS LP-PLA$_2$ INHIBITORS

RELATED APPLICATION

The present application claims priority from PCT International Application No. PCT/CN2011/077702, filed on Jul. 27, 2011 at the State Intellectual Property Office of the People's Republic of China, the entire contents of which is incorporated herein by reference.

FIELD OF THE INVENTION

The present invention relates to novel [6,6] bicyclic pyrimidone compounds, processes for their preparation, intermediates useful in their preparation, pharmaceutical compositions containing them, and their use in therapy for the treatment of diseases or conditions mediated by Lp-PLA$_2$.

BACKGROUND OF THE INVENTION

Lipoprotein-associated phospholipase A$_2$ (Lp-PLA$_2$) previously known as platelet-activating factor acetylhydrolase (PAF-AH), is a phospholipase A2 enzyme involved in hydrolysis of lipoprotein lipids or phospholipids. Lp-PLA$_2$ travels with low-density lipoprotein (LDL) and rapidly cleaves oxidized phosphatidylcholine molecules derived from the oxidation of LDL. (See e.g., Zalewski A, et al., *Arterioscler. Thromb. Vasc. Biol.*, 25, 5, 923-31(2005)). Lp-PLA$_2$ hydrolyzes the sn-2 ester of the oxidized phosphatidylcholines to give lipid mediators, lysophosphatidylcholine (lysoPC) and oxidized nonesterified fatty acids (NEFAs). It has been observed that lysoPC and NEFAs elicit inflammatory responses. (See e.g., Zalewski A, et al. (2005)).

A number of Lp-PLA$_2$ inhibitors and/or uses thereof have been previously described. (See. for example, published patent application nos. WO96/13484, WO96/19451, WO97/02242, WO97/12963, WO97/21675, WO97/21676, WO97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, and WO08/048866.) Disclosed uses include treating disease that involves or is associated with endothelial dysfunction, disease that involves lipid oxidation in conjunction with Lp-PLA$_2$ activity (e.g., associated with the formation of lysophosphatidylcholine and oxidized free fatty acids), and disease that involves activated monocytes, macrophages or lymphocytes or which is associated with increased involvement of monocytes, macrophages or lymphocytes. Examples of diseases or conditions include atherosclerosis (e.g. peripheral vascular atherosclerosis and cerebrovascular atherosclerosis), diabetes, hypertension, angina pectoris, after ischaemia and reperfusion, rheumatoid arthritis, stroke, inflammatory conditions of the brain such as Alzheimer's Disease, various neuropsychiatric disorders such as schizophrenia, myocardial infarction, ischaemia, reperfusion injury, sepsis, acute and chronic inflammation, and psoriasis.

Lp-PLA$_2$ inhibitors and/or uses thereof are also reported, for example, in PCT Publication Nos. WO05/003118 (and its Canadian family member CA 2530816A1); WO06/063811; WO06/063813 and WO 2008/141176; JP 200188847; and US Published Patent Application Nos. US 2008/0279846 A1, US 2010/0239565 A1, and US 2008/0280829 A1.

Other researchers have studied the effects related to Lp-PLA$_2$ and inhibitors thereof. For example, research data has also indicated that LysoPC promotes atherosclerotic plaque development, which can ultimately lead to the formation of a necrotic core. (See e.g., Wilensky et al., *Current Opinion in Lipidology*, 20, 415-420 (2009)). In addition, the effect of Lp-PLA$_2$ inhibitors on atherosclerotic plaque composition was demonstrated in a diabetic and hypercholesterolemic porcine model of accelerated coronary atherosclerosis. (See e.g., Wilensky et al., *Nature Medicine*, 10, 1015-1016 (2008)). These research results provided further evidence that Lp-PLA$_2$ inhibitors may be used to treat atherosclerosis.

Additional research has found that high Lp-PLA$_2$ activity is associated with high risk of dementia, including Alzheimer's disease (AD) (See e.g., Van Oijen, et al. Annals of Neurology, 59, 139 (2006)). Higher level of oxidized LDL has also been observed in AD patients (See e.g., Kassner et al. *Current Alzheimer Research*, 5, 358-366 (2008); Dildar, et al., *Alzheimer Dis Assoc Disord*, 24, April-June (2010); Sinem, et al. *Current Alzheimer Research*, 7, 463-469 (2010)). Further, research data has shown that neuroinflammation is present in AD patients and multiple cytotoxic inflammatory cytokines are up-regulated in AD patients. (See e.g., Colangelo, et al., *Journal of Neuroscience Research*, 70, 462-473 (2002); Wyss-Coray, *Nature Medicine*, 12, September (2006)). Research has shown that LysoPC function is a pro-inflammatory factor inducing multiple cytotoxic inflammatory cytokine release (See Shi, et al. *Atherosclerosis*, 191, 54-62 (2007)). Therefore, this recent research has provided additional evidence that that the inhibitors of Lp-PLA$_2$ can be used to treat AD by inhibiting activity of Lp-PLA$_2$ and reducing lysoPC production.

In addition, the treatment of an Lp-PLA$_2$ inhibitor on a diabetic and hypercholesterolemia swine model demonstrated that the blood-brain-barrier leakage and the brain amyloid beta protein (Aβ) burden, the pathological hallmarks of Alzheimer's disease, were reduced. (See U.S. Patent Application Publication No. 2008/0279846). This publication describes several uses of Lp-PLA$_2$ inhibitors for treating diseases associated with blood-brain-barrier leakage, including, e.g., Alzheimer's disease and vascular dementia.

Further, neuroinflammation, including multiple cytotoxic cytokine release, is a common feature of all neurodegenerative diseases including multiple sclerosis, amyotrophic lateral sclerosis, Parkinson's disease, Alzheimer's disease, etc. (See e.g., Perry, *Acta Neuropathol*, 120, 277-286 (2010)). As discussed above, Lp-PLA$_2$ inhibitors can reduce inflammation, for example, reducing multiple cytokine release by suppressing lysoPC production. (See e.g., Shi, et al. *Atherosclerosis* 191, 54-62 (2007)). Thus, inhibiting Lp-PLA$_2$ is a potential therapeutic treatment for neurodegenerative diseases including multiple sclerosis, amyotrophic lateral sclerosis, Parkinson's disease, etc.

In addition to the inflammatory effect, LysoPC has been implicated in leukocyte activation, induction of apoptosis and mediation of endothelial dysfunction (See, e.g., Wilensky et al., *Current Opinion in Lipidology*, 20, 415-420 (2009)). Therefore, it is believed that Lp-PLA$_2$ inhibitors can be used to treat tissue damage associated with diabetes by reducing the production of lysoPC, which can cause a continuous cycle of vascular inflammation and increased reactive oxygen species (ROS) production. In light of the inflammatory roles of Lp-PLA$_2$ and the association between localized inflammatory processes and diabetic retinopathy, it is postulated that Lp-PLA$_2$ can be used to treat diabetic eye disease.

Glaucoma and age-related macular degeneration (AMD) are retina neurodegenerative diseases. Studies suggested that inflammation, including TNF-alpha signaling, may play an important role in the pathogenesis of glaucoma and AMD (See e.g., Buschini et al., *Progress in Neurobiology*, 95, 14-25 (2011); Tezel, *Progress in Brain Research*, vol. 173, ISSN0079-6123, Chapter 28). Thus, considering Lp-PLA$_2$ inhibitors' function of blocking inflammatory cytokine release (See e.g., Shi, et al. *Atherosclerosis*, 191, 54-62 (2007)), it is believed that Lp-PLA$_2$ inhibitors can provide a potential therapeutic application for both glaucoma and AMD.

In view of the number of pathological responses that are mediated by Lp-PLA$_2$, attempts have been made to prepare compounds that inhibit its activity. Though a number of such compounds have been disclosed in the art, there remains a continuing need for inhibitors of Lp-PLA$_2$ which can be used in the treatment of a variety of conditions.

SUMMARY OF THE INVENTION

In a first aspect, this invention relates to compounds of Formula (I) or pharmaceutically acceptable salts thereof,

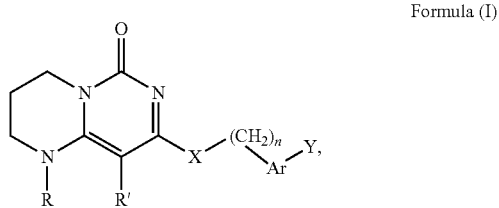

Formula (I)

wherein:
R is H or C$_1$-C$_6$alkyl,
R' is H, halo, or C$_1$-C$_6$alkyl,
X is —O—, —NH—, —N(C$_1$-C$_6$alkyl)-, —S— or —CH$_2$—,
n is 0, 1, 2 or 3, and when X is —CH$_2$—, n is 1 or 2,
Ar is phenyl or heteroaryl, either of which is unsubstituted or substituted with one or more groups selected from the group consisting of CN, halo, OH, —NH$_2$, —NHR$_1$, —NR$_1$R$_2$, C$_1$-C$_6$alkyl, C$_1$-C$_6$alkoxy, and C$_1$-C$_6$haloalkyl, and
Y is absent or —OAr', —NH—Ar', —N(C$_1$-C$_6$alkyl)-Ar', or —(CH$_2$)—Ar',
wherein Ar' is phenyl or heteroaryl, either of which is unsubstituted or substituted with one or more groups selected from the group consisting of CN, halo, OH, —NH$_2$, —NHR$_1$, —NR$_1$R$_2$, C$_1$-C$_6$alkyl, C$_1$-C$_6$alkoxy, and C$_1$-C$_6$haloalkyl, and
each occurrence of R$_1$ and R$_2$ are independently C$_1$-C$_6$alkyl.

This invention also relates to a pharmaceutical composition comprising compounds of this invention and one or more pharmaceutically acceptable excipients.

The invention also relates to methods of treating a disease associated with the activity of Lp-PLA$_2$, which comprises treating a subject in need thereof with a therapeutically effective amount of an inhibitor of Lp-PLA$_2$. The disease may be associated with the increased involvement of monocytes, macrophages or lymphocytes; with the formation of lysophosphatidylcholine and oxidized free fatty acids; with lipid oxidation in conjunction with Lp-PLA$_2$ activity; or with endothelial dysfunction.

This invention also provides methods of treating a disease by inhibiting Lp-PLA$_2$ activity. Exemplary diseases include, but are not limited to, neurodegeneration disease (e.g., Alzheimer's disease, vascular dementia), atherosclerosis, stroke, metabolic bone disorder (e.g., bone marrow abnormalities), dyslipidemia, Paget's diseases, type II diseases, metabolic syndrome, insulin resistance, and hyperparathyroidism, diabetic ocular disorder (e.g., macular edema, diabetic retinopathy, and posterior uveitis), macular edema, wound healing, rheumatoid arthritis, chronic obstructive pulmonary disease (COPD), psoriasis, and multiple sclerosis.

The methods comprise administering a safe and effective amount of a compound of this invention to a subject in need thereof. It is not intended that the present invention is limited to any particular stage of the disease (e.g. early or advanced).

This invention also provides methods of treating Alzheimer's disease. The methods comprise administering to a subject in need thereof a safe and effective amount of a compound of this invention.

This invention also provides methods of treating atherosclerosis. The methods comprise administering to a subject in need thereof a safe and effective amount of a compound of this invention.

This invention also provides methods of decreasing beta amyloid (also referred to as "Aβ") accumulation in the brain of a subject. The methods comprise administering to a subject in need thereof a safe and effective amount of a compound of the present invention. In certain embodiment, the beta amyloid is Abeta-42.

This invention also provides methods for treating eye diseases and disorders by administering a compound of this invention. In certain embodiment, this invention provides methods of treating macular edema, which comprises administering to the subject a safe and effective amount of a compound of this invention. In certain embodiment, the macular edema is associated with diabetic eye disease, for example, diabetic retinopathy. In one embodiment, the macular edema is associated with posterior uveitis.

This invention also provides a use of compounds of this invention in the manufacture of a medicament for treating diseases described herein.

This invention also provides compounds of this invention for use in the treatment described herein.

DETAILED DESCRIPTION OF THE INVENTION

As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology and virology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are incorporated by reference in their entirety. In case of a conflict in terminology, the present specification is controlling.

A. DEFINITIONS

As used herein, the term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

The term "neurodegeneration disease" as used herein refers to a varied assortment of central nervous system disorders characterized by gradual and progressive loss of neural tissue and/or neural tissue function. A neurodegeneration disease is a class of neurological disorder or disease where the neurological disease is characterized by a gradual and progressive loss of neural tissue, and/or altered neurological function, typically reduced neurological function as a result of a gradual and progressive loss of neural tissue. In some embodiments, the neurodegeneration diseases described herein are neurodegeneration diseases or disorders where there is an abnormal blood brain barrier, for example a permeable blood brain barrier. Examples of neurodegeneration diseases where there is a defective blood brain barrier include, but are not limited to, Alzheimer's disease, Huntington's disease, Parkinson's disease, vascular dementia and the like.

The term "vascular dementia" is also referred to as "multi-infarct dementia", which refers to a group of syndromes caused by different mechanisms, which all result in vascular lesions in the brain. The main subtypes of vascular dementia are, for example, vascular mild cognitive impairment, multi-infarct dementia, vascular dementia due to a strategic single infarct, (affecting the thalamus, the anterior cerebral artery, the parietal lobes or the cingulated gyms), vascular dementia due to hemorrhagic lesions, small vessel disease (including, e.g. vascular dementia due to lacunar lesions and Binswanger disease), and mixed Alzheimer's Disease with vascular dementia.

The phrase "blood-brain barrier" or "BBB" are used interchangeably herein, and are used to refer to the permeability barrier that exists in blood vessels as they travel through the brain tissue that severely restricts and closely regulates what is exchanged between the blood and the brain tissue. The blood brain barrier components include the endothelial cells that form the innermost lining of all blood vessels, the tight junctions between adjacent endothelial cells that are structural correlate of the BBB, the basement membrane of endothelial cells and the expanded foot process of nearby astrocytes which cover nearly all of the exposed outer surface of the blood vessel.

The phrase "metabolic bone disease" as used herein refers to a varied assortment of bone diseases and disorders characterized by gradual and progressive loss of bone tissue. Metabolic bone diseases described herein are metabolic bone diseases whereby there is a condition of diffusely decreased bone density and/or diminished bone strength. Such diseases are characterized by histological appearance. Exemplary metabolic bone diseases include, but are not limited to, osteoporosis which is characterized by decreased mineral and bone matrix, and osteomalacia which is characterized by decreased mineral but intact bone matrix.

The term "osteopenic diseases" or "osteopenia" are used interchangeably herein, and refer to conditions with decreased calcification and/or bone density, and is a descriptive term used to refer to all skeletal systems in which decreased calcification and/or bone density is observed. Osteopenia also refers to a reduced bone mass due to inadequate osteiod synthesis.

The term "osteoporosis" refers to conditions in which mineral and/or bone matrix are decreased and/or bone mass is reduced.

"Alkyl" refers to a monovalent, saturated hydrocarbon chain having a specified number of carbon atoms. For example, $C_1$-$C_6$ alkyl refers to an alkyl group having from 1 to 6 carbon atoms. In still other embodiments, alkyl groups contain 1 to 2, 3, 4, or 5 carbon atoms. Alkyl groups may be optionally substituted with one or more substituent as defined herein. Alkyl groups may be straight or branched. In some embodiments, branched alkyl groups may have one, two, or three branches. In one embodiment, alkyl is unsubstituted. Exemplary alkyl groups include, but are not limited to, methyl, methylethyl, ethyl, propyl (n-propyl and isopropyl), methylpropyl, butyl (n-butyl, isobutyl, and t-butyl), pentyl (n-pentyl, isopentyl, and neopentyl), and hexyl.

"Alkoxy" refers to the group —O-alkyl. In some embodiments, alkoxyl groups contain 1 to 2, 3, 4, or 5 carbon atoms. Exemplary alkoxy groups include, but are not limited to, methoxy, ethoxy and propoxy.

"Halogen" refers to fluorine (F), chlorine (Cl), bromine (Br), or iodine (I). "Halo" refers to the halogen radicals: fluoro (—F), chloro (—Cl), bromo (—Br), or iodo (—I).

"Haloalkyl" refers to an alkyl group, as defined above, having one or more halogen atoms selected from F, Cl, Br, or I, which are substituted on any or all of the carbon atoms of the alkyl group by replacing hydrogen atoms attached to the carbon atoms. Exemplary haloalkyl groups include, but are not limited to, chloromethyl, bromoethyl, trifluoromethyl, dichloromethyl.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituent as defined herein. Heteroaryl groups are monocyclic ring systems having from 5, 6 or 7 member atoms. In some embodiments, heteroaryl groups are monocyclic ring system having 6 member atoms. In other embodiments, heteroaryl group have one nitrogen atom as member atom. In one embodiment, heteroaryl is unsubstituted. Examples of heteroaryl include, but are not limited to, pyrrolyl, pyrazolyl, imidazolyl, oxazolyl, pyridinyl and pyrimidinyl.

"Optionally substituted" indicates that a group, such as alkyl, alkenyl, alkynyl, cycloalkyl, cycloalkenyl, heterocycloalkyl, phenyl or heteroaryl, may be unsubstituted, or the group may be substituted with one or more substituent as defined.

As used herein, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Exemplary substituents include, but are not limited to, halo, hydroxyl, amino, amide, —SH, cyano, nitro, thioalkyl, carboxylic acid, —NH—C(=NH)—NH$_2$, alkyl, alkenyl, alkynyl, alkoxyl, aryl, heteroaryl, cycloalkyl, heterocycloalkyl, in which alkyl, alkenyl, alkynyl, alkoxyl, aryl, heteroaryl, cycloalkyl, thioalkyl and heterocycloalkyl may be further substituted. Suitable substituents are defined herein for each substituted or optionally substituted group.

As used herein, "treat", "treating" or "treatment" in reference to a condition means: (1) to ameliorate the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, and/or (4) to slow the progression of the condition or one or more of the biological manifestations of the condition.

As used herein, "subject" means a mammalian subject (e.g., dog, cat, horse, cow, sheep, goat, monkey, etc.), and particularly human subjects including both male and female subjects, and including neonatal, infant, juvenile, adolescent, adult and geriatric subjects, and further including various races and ethnicities including, but not limited to, white, black, Asian, American Indian and Hispanic.

As used herein, "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, an "effective amount" means that the amount of a compound of this invention will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amount that is effective to enhance normal physiological function.

B. COMPOUNDS

This invention provides, in a first aspect, compounds of Formula I and pharmaceutically acceptable salts thereof:

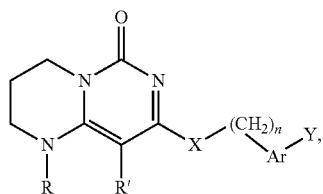

Formula (I)

wherein:
R is H or $C_1$-$C_6$alkyl,
R' is H, halo, or $C_1$-$C_6$alkyl,
X is —O—, —NH—, —N($C_1$-$C_6$alkyl)-, —S— or —CH$_2$—,
n is 0, 1, 2 or 3, and when X is —CH$_2$—, n is 1 or 2,
Ar is phenyl or heteroaryl, either of which is unsubstituted or substituted with one or more groups selected from the group consisting of CN, halo, OH, —NH$_2$, —NHR$_1$, —NR$_1$R$_2$, $C_1$-$C_6$alkyl, $C_1$-$C_6$alkoxy, and $C_1$-$C_6$haloalkyl, and
Y is absent or —O—Ar', —NH—Ar', —N($C_1$-$C_6$alkyl)-Ar', or —(CH$_2$)—Ar',
wherein Ar' is phenyl or heteroaryl, either of which is unsubstituted or substituted with one or more groups selected from the group consisting of CN, halo, OH, —NH$_2$, —NHR$_1$, —NR$_1$R$_2$, $C_1$-$C_6$alkyl, $C_1$-$C_6$alkoxy, and $C_1$-$C_6$haloalkyl, and
each occurrence of R$_1$ and R$_2$ are independently $C_1$-$C_6$ alkyl.

In one embodiment, the invention relates to compounds of Formula (I) wherein
R is H, CH$_3$, or iso-propyl,
R' is H,
X is —O—, —S—, —NH—, or —CH$_2$—, n is 1 or 2,
Ar is unsubstituted phenyl, or phenyl substituted with one or more groups selected from the group consisting of CN, F, CF$_3$, Cl, OCH$_3$ and CH$_3$, or Ar is pyridinyl or thiophenyl, either of which is unsubstituted or substituted with one or more F,
Y is absent or —O—Ar', wherein Ar' is unsubstituted phenyl, or phenyl substituted with one or more groups selected from the group consisting of CF$_3$, F, Cl, CN, and CH$_3$, or Ar' is pyridinyl or pyrimidinyl, either of which is unsubstituted or substituted with one or more groups selected from CF$_3$ or CH$_3$,
or pharmaceutically acceptable salts thereof.

In one embodiment, the invention relates to compounds of Formula (I) wherein
R is H, CH$_3$, or iso-propyl,
R' is H,
X is —O— or —CH$_2$—,
n is 1 or 2,
Ar is unsubstituted phenyl, or phenyl substituted with one or more groups selected from the group consisting of CN, F, CF$_3$, Cl, and CH$_3$, or Ar is pyridinyl or thiophenyl, either of which is unsubstituted or substituted with one or more F,
Y is absent or —O—Ar', wherein Ar' is unsubstituted phenyl, or phenyl substituted with one or more groups selected from the group consisting of CF$_3$, F, Cl, CN, and CH$_3$, or Ar' is pyridinyl or pyrimidinyl, either of which is unsubstituted or substituted with one or more groups selected from CF$_3$ or CH$_3$,
or pharmaceutically acceptable salts thereof.

In one embodiment, this invention relates to compounds of Formula (I), wherein R is H, CH$_3$, or iso-propyl or pharmaceutically acceptable salts thereof. In one embodiment, this invention relates to compounds of Formula (I), wherein R is $C_1$-$C_3$alkyl or pharmaceutically acceptable salts thereof. In yet a further embodiment, this invention relates to compounds of Formula (I), wherein R is CH$_3$ or pharmaceutically acceptable salts thereof. In yet a further embodiment, this invention relates to compounds of Formula (I), wherein R is iso-propyl or pharmaceutically acceptable salts thereof.

In another embodiment, this invention relates to compounds of Formula (I) and any of the above applicable embodiments, wherein R' is H or pharmaceutically acceptable salts thereof.

In one embodiment, this invention relates to compounds of Formula (I) and any of the above applicable embodiments, wherein X is —O—, —S—, —NH—, or —CH$_2$—, or pharmaceutically acceptable salts thereof. Further, in one embodiment, this invention also relates to compounds of Formula (I) and any of the above applicable embodiments, wherein X is —O— or pharmaceutically acceptable salts thereof. In yet a further embodiment, this invention also relates to compounds of Formula (I) and any of the above applicable embodiments, wherein X is —NH— or pharmaceutically acceptable salts thereof.

In other embodiments, this invention relates to compounds of Formula (I) and any of the above applicable embodiments, wherein n is 1 or 2, or pharmaceutically acceptable salts thereof. In a further embodiment, this invention also relates to compounds of Formula (I) and any of the above applicable embodiments, wherein n is 1, or pharmaceutically acceptable salts thereof.

In one embodiment, this invention relates to compounds of Formula (I) and any of the above applicable embodiments, wherein Ar is unsubstituted phenyl, or phenyl substituted with one or more groups selected from the group consisting of CN, F, CF$_3$, Cl, and CH$_3$, or Ar is pyridinyl or thiophenyl, either of which is unsubstituted or substituted with one or more F, or a pharmaceutically acceptable salt thereof. In a further embodiment, this invention also relates to compounds of Formula (I) and any of the above applicable embodiments, wherein Ar is unsubstituted phenyl or phenyl substituted with one or more groups independently selected from halo or cyano or pharmaceutically acceptable salts thereof. In yet a further embodiment, this invention also relates to compounds of Formula (I) and any of the above applicable embodiments, wherein Ar is phenyl, which is substituted with one or more groups independently selected from the group consisting of —F and —CN, or pharmaceutically acceptable salts thereof. In one embodiment, this invention also relates to compounds of Formula (I) and any of the above applicable embodiments, wherein Ar is phenyl substituted with one or more groups independently selected from halo or pharmaceutically acceptable salts thereof. In a further embodiment, this invention also relates to compounds of Formula (I) and any of the above applicable embodiments, wherein Ar is phenyl substituted with one or more F, or pharmaceutically acceptable salts thereof. In a further embodiment, this invention also relates to compounds of Formula (I) and any of the above applicable embodiments, wherein Ar is phenyl di-substituted with F, or pharmaceutically acceptable salts thereof. In a further embodiment, this invention also relates to compounds of Formula (I) and any of the above applicable embodiments, wherein Ar is phenyl tri-substituted with F, or pharmaceutically acceptable salts thereof.

In certain embodiment, this invention relates to compounds of Formula (I) and any of the above applicable embodiments, wherein Y is absent or —O—Ar', wherein Ar' is unsubstituted phenyl, or phenyl substituted with one or more groups independently selected from the group consisting of CF$_3$, F, Cl, CN, and CH$_3$, or Ar' is pyridinyl or pyrimidinyl, either of which is unsubstituted or substituted with one or more groups independently selected from the group consisting of CF$_3$ and CH$_3$. In a further embodiment, this invention also relates to compounds of Formula (I) and any of the above applicable embodiments, wherein Y is —O—Ar' and Ar' is phenyl, which is substituted with one or more groups independently selected from the group consisting of CF$_3$, F and Cl, or pharmaceutically acceptable salts thereof. In a further embodiment, this invention also relates to compounds of Formula (I) and any of the above applicable embodiments, wherein Y is —O—Ar' and Ar' is phenyl substituted with one or more CF$_3$, or pharmaceutically acceptable salts thereof. In yet a further embodiment, this invention also relates to compounds of Formula (I) and any of the above applicable embodiments, wherein Y is —O—Ar' and Ar' is phenyl substituted with one or more groups independently selected from halo, or pharmaceutically acceptable salts thereof. In a further embodiment, this invention also relates to compounds of Formula (I) and any of the above applicable embodiments, wherein Y is —O—Ar' and Ar' is phenyl di-substituted with groups independently selected from the group consisting of CF$_3$ and halo, or pharmaceutically acceptable salts thereof. In a further embodiment, this invention also relates to compounds of Formula (I) and any of the above applicable embodiments, wherein Y is —O—Ar' and Ar' is phenyl substituted with one or more groups independently selected from the group consisting of halo and CN, or pharmaceutically acceptable salts thereof.

In one embodiment, this invention relates to compounds of Formula (I) and any of the above applicable embodiments, wherein Y is —O—Ar' and Ar' is pyridinyl, which is substituted with one or more substituent independently selected from the group consisting of CF$_3$, F, CH$_3$ and Cl, or pharmaceutically acceptable salts thereof. In one embodiment, this invention also relates to compounds of Formula (I) and any of the above applicable embodiments, wherein Y is —O—Ar' and Ar' is pyridinyl, which is substituted with one or more CF$_3$, or pharmaceutically acceptable salts thereof. In one embodiment, this invention also relates to compounds of Formula (I) and any of the above applicable embodiments, wherein Y is —O—Ar' and Ar' is pyridinyl, which is substituted with one or more groups independently selected from halo, or pharmaceutically acceptable salts thereof. In a further embodiment, this invention also relates to compounds of Formula (I) and any of the above applicable embodiments, wherein Y is —O—Ar' and Ar' is unsubstituted pyridinyl, or pharmaceutically acceptable salts thereof.

In a further embodiment, this invention also relates to compounds of Formula (I) and any of the above applicable embodiments, wherein Y is absent or pharmaceutically acceptable salts thereof.

In certain embodiment, the compounds of Formula (I), or a pharmaceutically acceptable salt thereof, has the structure of Formula (IA),

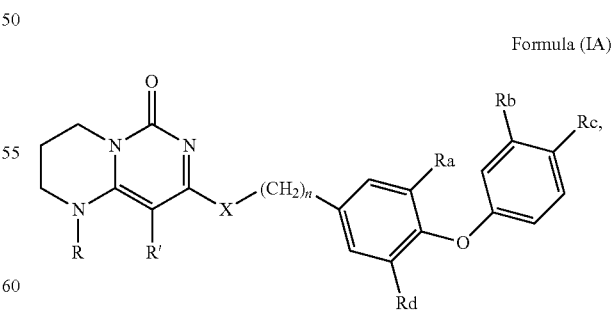

Formula (IA)

wherein R, R', X, and n are defined in Formula (I), Ra, Rb, Rc and Rd are independently selected from the group consisting of H, halo, CF$_3$ and CN.

In a further embodiment, the invention relates to compounds of Formula (IA) wherein R is H, $CH_3$, or iso-propyl,
R' is H,
X is —O—, —S—, —NH—, or —$CH_2$—,
n is 1 or 2,
Ra, Rb, Rc and Rd are independently selected from the group consisting of H, halo, $CF_3$ and CN,
or pharmaceutically acceptable salts thereof.

In yet a further embodiment, the invention relates to compounds of Formula (IA) wherein
R is $CH_3$,
R' is H,
X is —O—,
n is 1,
Ra, Rb, Rc and Rd are independently selected from the group consisting of hydrogen, halo, $CF_3$ and CN,
or pharmaceutically acceptable salts thereof.

In one embodiment, this invention relates to compounds of Formula (IA), wherein R is H or $C_1$-$C_3$ alkyl or pharmaceutically acceptable salts thereof. In yet a further embodiment, this invention relates to compounds of Formula (IA), wherein R is H, $CH_3$, or iso-propyl or pharmaceutically acceptable salts thereof. In yet a further embodiment, this invention relates to compounds of Formula (IA), wherein R is $CH_3$ or pharmaceutically acceptable salts thereof. In yet a further embodiment, this invention relates to compounds of Formula (IA), wherein R is iso-propyl or pharmaceutically acceptable salts thereof.

In certain embodiments, this invention relates to compounds of Formula (IA) and any of the above applicable embodiments, R' is hydrogen or pharmaceutically acceptable salts thereof.

In certain embodiments, this invention relates to compounds of Formula (IA) and any of the above applicable embodiments, wherein X is —O—, —S—, —NH—, or —$CH_2$—, or pharmaceutically acceptable salts thereof. Further, this invention also relates to compounds of Formula (IA) and any of the above applicable embodiments, wherein X is —O— or pharmaceutically acceptable salts thereof.

In certain embodiments, this invention relates to compounds of Formula (IA) and any of the above applicable embodiments, wherein n is 1 or 2, or pharmaceutically acceptable salts thereof. In a further embodiment, this invention also relates to compounds of Formula (IA) and any of the above applicable embodiments, wherein n is 1, or pharmaceutically acceptable salts thereof.

In certain embodiments, this invention relates to compounds of Formula (IA) and any of the above applicable embodiments, wherein Ra and Rd are independently selected from the group consisting of CN, F and H. In a further embodiment, this invention also relates to compounds of Formula (IA) and any of the above applicable embodiments, wherein Ra and Rd are independently selected from the group consistent of F and H.

In other embodiments, this invention relates to compounds of Formula (IA) and any of the above applicable embodiments, wherein Rb is selected from the group consisting of $CF_3$, F, H and Cl. In a further embodiment, this invention also relates to compounds of Formula (IA) and any of the above applicable embodiments, wherein Rb is $CF_3$ or F.

In certain embodiments, this invention relates to compounds of Formula (IA) and any of the above applicable embodiments, wherein Rc is selected from the group consisting of F, H and Cl. In yet a further embodiment, this invention also relates to compounds of Formula (IA) and any of the above applicable embodiments, Rc is H or F.

In certain embodiments, the compounds of Formula (I) has the structure of Formula (IB),

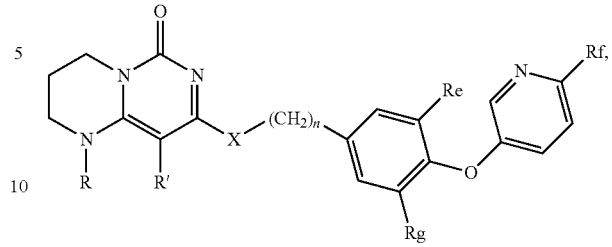

Formula (IB)

wherein R, R', X, and n are defined in Formula (I), and Re, Rf and Rg are independently selected from the group consisting of H, halo, CN and $CF_3$.

In a further embodiment, this invention relates to compounds of Formula (IB), wherein R, R', and n are defined in Formula (I), X is —O—, and Re, Rf and Rg are independently selected from the group consisting of H, halo, CN and $CF_3$.

In certain embodiments, this invention relates to compounds of Formula (IB) and any of the above applicable embodiments, wherein R is $C_1$-$C_3$ alkyl or pharmaceutically acceptable salts thereof. In a further embodiment, this invention also relates to compounds of Formula (IB) and any of the above applicable embodiments, wherein R is $CH_3$ or pharmaceutically acceptable salts thereof. In yet a further embodiment, this invention also relates to compounds of Formula (IB) and any of the above applicable embodiments, wherein R is iso-propyl or pharmaceutically acceptable salts thereof.

In other embodiments, this invention also relates to compounds of Formula (IB) and any of the above applicable embodiments, wherein R' is H or pharmaceutically acceptable salts thereof.

In other embodiments, this invention also relates to compounds of Formula (IB) and any of the above applicable embodiments, wherein n is 1 or pharmaceutically acceptable salts thereof.

In certain embodiment, this invention also relates to compounds of Formula (IB) and any of the above applicable embodiments, wherein Re and Rg are independently selected from the group consisting of F, H and CN, or pharmaceutically acceptable salts thereof.

In other embodiment, this invention also relates to compounds of Formula (IB) and any of the above applicable embodiments, wherein Rf is selected from the group consisting of $CF_3$, H and Cl, or pharmaceutically acceptable salts thereof.

In one embodiment, a compound according to Formula (I) or Formula (IB) has the structure of 8-((3,5-difluoro-4-((6-(trifluoromethyl)pyridin-3-yl)oxy)benzyl)oxy)-1-methyl-3,4-dihydro-1H-pyrimido[1,6-α]pyrimidin-6(2H)-one

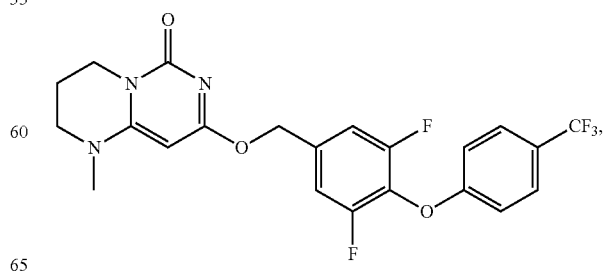

or a pharmaceutically acceptable salt thereof.

In certain embodiment, the compound of Formula (I) has the structure of Formula (IC)

Formula (IC)

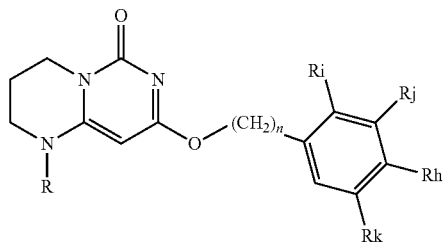

wherein
R is CH$_3$, or iso-propyl,
n is 1 or 2,
Ri is selected from the group consisting of F, Cl and H,
Rj is selected from the group consisting of H, F, Cl, CF$_3$, CN and OCH$_3$,
Rh is selected from the group consisting of H, F, Cl, CN, and CF$_3$, and
Rk is selected from the group consisting of H, F and CN, or pharmaceutically acceptable salts thereof.

In certain embodiments, this invention also relates to compounds of Formula (IC), wherein R is CH$_3$, or iso-propyl, n is 1, Rj, Rk and Rh are F, and Ri is H, or pharmaceutically acceptable salts thereof.

In yet a further embodiment, this invention relates to compounds of Formula (IC), wherein R is iso-propyl or pharmaceutically acceptable salts thereof.

In certain embodiments, this invention relates to compounds of Formula (IC), wherein R is CH$_3$ or pharmaceutically acceptable salts thereof. In yet a further embodiment, this invention also relates to compounds of Formula (IC), wherein R is iso-propyl or pharmaceutically acceptable salts thereof.

In other embodiments, this invention relates to compounds of Formula (IC) and any of the above applicable embodiments, wherein n is 1 or pharmaceutically acceptable salts thereof.

In certain embodiments, this invention relates to compounds of Formula (IC) and any of the above applicable embodiments, wherein Rj is selected from the group consisting of H, F, and CF$_3$, or pharmaceutically acceptable salts thereof. In a yet further embodiment, this invention also relates to compounds of Formula (IC) and any of the above applicable embodiments, wherein Rj is H or pharmaceutically acceptable salts thereof. In a further embodiment, this invention also relates to compounds of Formula (IC) and any of the above applicable embodiments, wherein Rj is F, or pharmaceutically acceptable salts thereof. In a further embodiment, this invention also relates to compounds of Formula (IC) and any of the above applicable embodiments, wherein Rj is CF$_3$ or pharmaceutically acceptable salts thereof.

In certain embodiment, this invention relates to compounds of Formula (IC) and any of the above applicable embodiments, wherein Rk is H or F or pharmaceutically acceptable salts thereof. In certain embodiment, this invention also relates to compounds of Formula (IC) and any of the above applicable embodiments, wherein Rk is H or pharmaceutically acceptable salts thereof. In certain embodiment, this invention also relates to compounds of Formula (IC) and any of the above applicable embodiments, wherein Rk is F or pharmaceutically acceptable salts thereof.

In certain embodiments, this invention relates to compounds of Formula (IC) and any of the above applicable embodiments, wherein Rh is selected from the group consisting of F, Cl, H and CF$_3$, or pharmaceutically acceptable salts thereof. In a further embodiment, this invention also relates to compounds of Formula (IC) and any of the above applicable embodiments, wherein Rh is F or H, or pharmaceutically acceptable salts thereof. In yet a further embodiment, this invention also relates to compounds of Formula (IC) and any of the above applicable embodiments, wherein Rh is H or pharmaceutically acceptable salts thereof.

In certain embodiments, this invention relates to compounds of Formula (IC) and any of the above applicable embodiments, wherein Ri is selected from the group consisting of F, Cl, and H, or pharmaceutically acceptable salts thereof. In a further embodiment, this invention also relates to compounds of Formula (IC) and any of the above applicable embodiments, wherein Ri is F or H, or pharmaceutically acceptable salts thereof. In yet a further embodiment, this invention also relates to compounds of Formula (IC) and any of the above applicable embodiments, wherein Ri is H or pharmaceutically acceptable salts thereof.

In one embodiment, a compound according to Formula (I) or Formula (IC) has the structure of

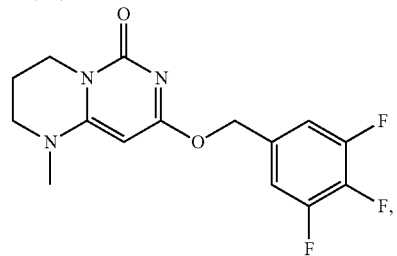 [SMILES: CN1CCCn2c1cc(OCc1cc(F)c(F)c(F)c1)nc2=O]

or a pharmaceutically acceptable salt thereof.

In one embodiment, a compound according to Formula (I) or Formula (IC) has the structure of

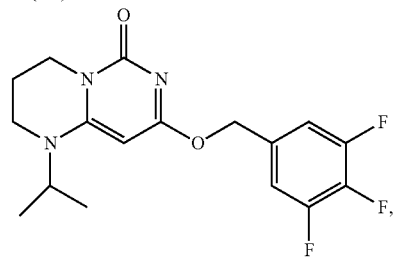

or a pharmaceutically acceptable salt thereof.

In one embodiment, a compound according to Formula (I) or Formula (IC) has the structure of

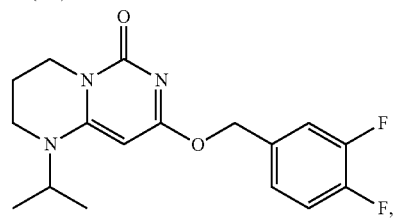

or a pharmaceutically acceptable salt thereof.

The compounds of Formula (I), Formula (IA), Formula (IB), Formula (IC) or pharmaceutically acceptable salts thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compounds of Formula (I), Formula (IA), Formula (IB), Formula (IC) or pharmaceutically acceptable salts thereof as mixtures with isomers thereof in which one or more chiral centers are inverted. Likewise, it is understood that the compounds of Formula (I), Formula (IA), Formula (IB), Formula (IC) or pharmaceutically acceptable salts thereof may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compounds of Formula (I), Formula (IA), Formula (IB), Formula (IC) or pharmaceutically acceptable salts thereof, as well as any wholly or partially equilibrated mixtures thereof. The present invention also includes the individual isomers of the compounds of Formula (I), Formula (IA), Formula (IB), Formula (IC) or pharmaceutically acceptable salts thereof as well as mixtures with isomers thereof in which one or more chiral centers are inverted. It is to be understood that the present invention includes all combinations and subsets of the particular groups defined hereinabove. The different isomeric forms may be separated or resolved one from the other by conventional methods, or any given isomer may be obtained by conventional synthetic methods or by stereospecific or asymmetric syntheses.

The invention also includes various deuterated forms of compounds of Formula (I), Formula (IA), Formula (IB), Formula (IC) or pharmaceutically acceptable salts thereof. Each available hydrogen atom attached to a carbon atom may be independently replaced with a deuterium atom. A person of ordinary skill in the art will know how to synthesize deuterated forms of compounds of Formula (I), Formula (IA), Formula (IB), Formula (IC) or pharmaceutically acceptable salts thereof. Commercially available deuterated starting materials may be employed in the preparation of deuterated forms of compounds of Formula (I), Formula (IA), Formula (IB), Formula (IC) or pharmaceutically acceptable salts thereof, or they may be synthesized using conventional techniques employing deuterated reagents (e.g. lithium aluminum deuteride).

In addition to the free base form of the compounds described herein, the salt form of the compounds is also within the scope of the present invention. The pharmaceutically-acceptable salts may be prepared in situ during the final isolation and purification of the compound, or by separately reacting the purified compound in its free acid or free base form with a suitable base or acid, respectively. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In certain embodiments, compounds of the present invention may contain an acidic functional group, which is acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, diethylamine, triethylamine, ethylenediamine, ethanolamine, diethanolamine, and cyclohexylamine.

In certain embodiments, compounds of the present invention may contain a basic group and are therefore capable of forming pharmaceutically-acceptable acid addition salts by treatment with a suitable acid. Suitable acids include pharmaceutically-acceptable inorganic acids and pharmaceutically-acceptable organic acids. These salts may be crystalline or amophorus. Exemplary pharmaceutically-acceptable acid addition salts include hydrochloride, hydrobromide, nitrate, methylnitrate, sulfate, bisulfate, sulfamate, phosphate acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. Some of these salts form solvates, some are crystalline.

The compounds described herein, their pharmaceutically acceptable salts, or solvates or hydrates of either, may exist in one or more polymorphic form. Therefore, in a further aspect, the invention provides a polymorph of a compound defined herein or their pharmaceutically acceptable salts, or a polymorph of a solvate or hydrate of a compound described herein or a pharmaceutically acceptable salt thereof.

C. SYNTHESIS OF COMPOUNDS

The process to be utilized in the preparation of the compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of the present invention are set forth below. All starting material and reagents described in the below general experimental schemes are commercially available.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

General Experimental Scheme 1

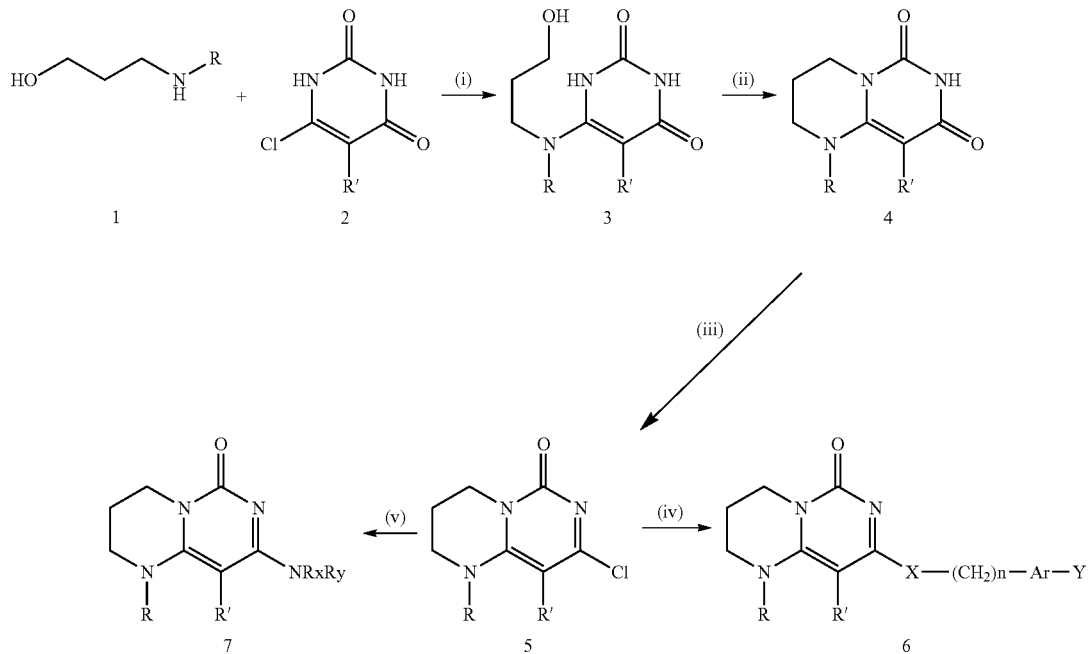

General Experimental Scheme 1 provides an exemplary synthesis for compounds 6 and 7. In scheme 1, $R_x$ is H or —($C_1$-$C_6$)alkyl, $R_y$ is —$(CH_2)_n$—Ar—Y, X is O or S, and R', R, Ar, Y and n are as defined in Formula (I). Step (i) may be carried out by reacting compound 1 with compound 2 using appropriate reagents such as KI in an appropriate solvent such as $H_2O$ under a suitable temperature such as 120° C. using microwave radiation to provide compound 3. Step (ii) may be an intra-molecular Mitsunobu reaction using appropriate reagents such as diisopropyl azodicarboxylate (DIAD) and $Ph_3P$ in a suitable solvent such as THF at a suitable temperature such as room temperature. Step (iii) may take place by reacting compound 4 with a suitable reagent such as $POCl_3$ under a suitable solvent such as $POCl_3$ at an appropriate temperature such as 90° C.

Step (iv) may be carried out by reacting compound 5 with Y—Ar—$(CH_2)_n$XH in the presence of a suitable base such as NaH in a suitable solvent such as dimethylformamide (DMF) at a suitable temperature such as 0° C. to provide compound 6, wherein R, R', Ar, Y and n are defined in Formula (I) and X is O or S.

Step (v) may be carried out by reacting compound 5 with $R_xR_y$NH in the presence of a suitable base such as triethylamine (TEA) in a suitable solvent such as dimethylformamide (DMF) at a suitable temperature 140° C. to provide compound 7.

General Experimental Scheme 2

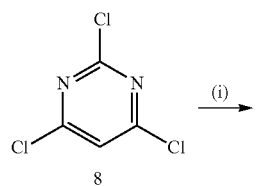

General Experimental Scheme 2 provides an alternative synthesis for compounds 11. In scheme 2, X is O, and Ar, Y and n are as defined in Formula (I). Step (i) may be carried out by reacting compound 8 with Y—Ar—$(CH_2)_n$XH using an appropriate base such as NaH in an appropriate solvent such as DMF under a suitable temperature such as room temperature to provide compound 9. Step (ii) may take place using appropriate reagents such as 3-bromopropan-1-amine and appropriate base such as DIPEA in a suitable solvent such as DMF at a suitable temperature such as 0° C. to afford compound 10. Step (iii) may be carried out by hydrolysis of compound 10 with a suitable base such as $K_2CO_3$ under a suitable solvent such as 1,4-dioxane and water at an appropriate temperature such as 50° C. to obtain compound 11.

General Experimental Scheme 3

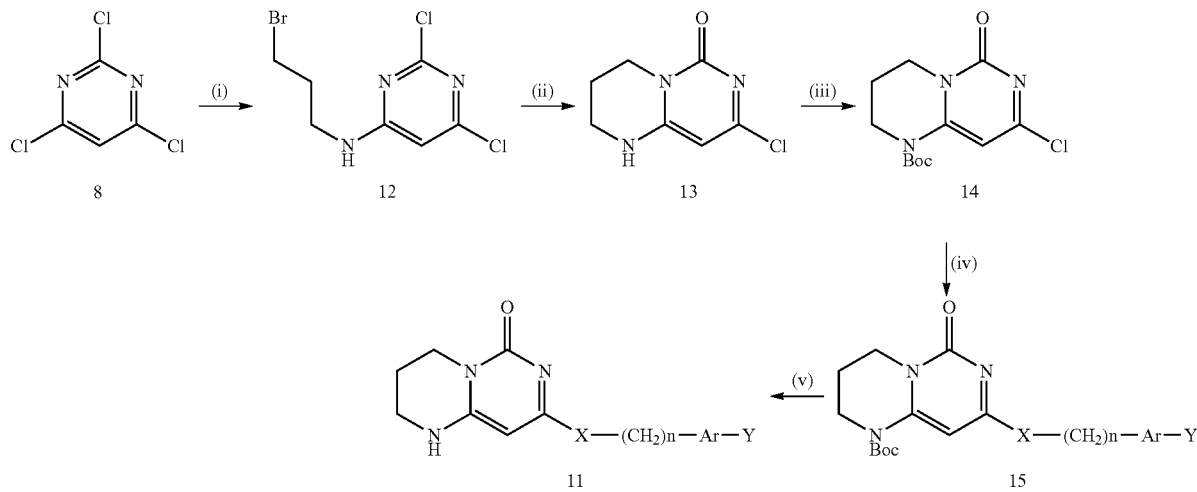

General Experimental Scheme 3 provides another alternative synthesis route for compounds 11. In Scheme 3, X is O, and Ar, Y and n are as defined in Formula (I). Step (i) may be carried out by reacting compound 8 with 3-bromopropan-1-amine using an appropriate base such as $Et_3N$ in an appropriate solvent such as $CH_3CN$ under a suitable temperature such as room temperature to provide compound 12. Step (ii) may take place using an appropriate base such as $K_2CO_3$ in a suitable solvent such as 1,4-dioxane at a suitable temperature such as 60° C. to afford compound 13. Step (iii) may be carried out by reacting compound 13 with $(Boc)_2O$ with a suitable catalyst such as DMAP under a suitable solvent such as THF at a suitable temperature such as room temperature to afford compound 14. Step (iv) may be carried out by reacting compound 14 with Y—Ar—$(CH_2)$—XH in the presence of a suitable base such as NaH in a suitable solvent such as THF at a suitable temperature such as 0° C. to provide compound 15. Step (v) may be carried out by reacting compound 15 with a suitable acid such as HCl in a suitable solvent such as 1,4-dioxane and at an appropriate temperature such as room temperature to obtain compound 11.

General Experimental Scheme 4

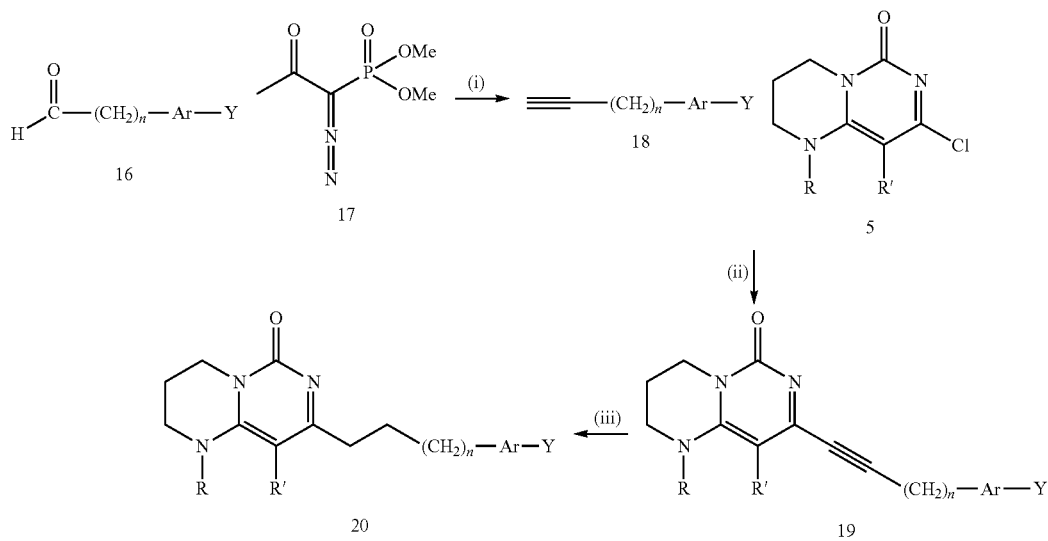

General Experimental Scheme 4 provides an exemplary synthesis for compound 20. In scheme 4, R, R', n, Ar and Y are as defined in Formula (I). Step (i) may be carried out by reacting compound 16 with compound 17 using appropriate reagents such as $K_2CO_3$ in an appropriate solvent such as MeOH at a suitable temperature such as room temperature to provide compound 18. Step (ii) may be a Sonagashira reaction of compound 18 and compound 5 using appropriate reagents such as $Pd_2(dba)_3$, CuI, TEA, and $(2\text{-fur})_3P$ in a suitable solvent such as toluene at a suitable temperature such as 50° C. Step (iii) may take place by hydrogenation of compound 19 with a suitable reagent such as Pd/C under $H_2$ atmosphere such as 1 bar in a suitable solvent such as MeOH at an appropriate temperature such as room temperature to afford compound 20.

All temperatures are reported in degrees Celsius. All other abbreviations are as described in the ACS Style Guide (American Chemical Society, Washington, D.C., 1986).
LCMS Conditions:
1) Acidic Conditions:
Mobile phase: water containing 0.05% TFA/0.05% acetonitrile
Column: Agilent SB-C18 4.6×30 mm-1.8 microns
Detection: MS and photodiode array detector (PDA)
2) Basic Conditions:
Mobile phase: water containing 10 mmol NH$_4$HCO$_3$/acetonitrile
Column: XBridge™ C18 4.6×50 mm-3.5 microns
Detection: MS and photodiode array detector (PDA)
Mass Directed Autoprep Purification (MDAP) Conditions:
1) Acidic Conditions:
Instrument: Waters instrument
Column: Sunfire Prep C18 column (5 um, 19×50 mm)
Mobile phase: water containing 0.05% TFA/acetonitrile.
2) Basic Conditions:
Instrument: Waters instrument
Column: Xbridge Prep C18 column (5 um, 19×50 mm)
Mobile phase: water containing 0.04% ammonia/acetonitrile.

ABBREVIATIONS AND RESOURCE SOURCES

The following abbreviations and resources are used herein below:
ISCO system—Teledyne ISCO (http://www.isco.com/html/seFlashChromatography.html)
r.t/rt/RT—room temperature;
ACN—acetonitrile;
AcCl—Acetic chloride
Aq.—aqueous
(BOC)$_2$O—di-tert-butyl dicarbonate
CV—Column volumes
DABCO—1,4-diazabicyclo[2.2.2]octane
DAST—diethylaminosulfur trifluoride
DBU—1,8-diazabicyclo[5.4.0]undec-7-ene
DCM—dichloromethane;
DIAD—diisopropyl azodiformate
DIPEA—N, N-diisopropylethylamine
DMA—N, N-dimethylacetamide;
DMAP—4-dimethylaminopyridine
DME—1,2-dimethoxyethane;
DMF—dimethylformamide;
DMSO—dimethyl sulfoxide
EA—ethyl acetate;
EDC—1-ethyl-3-(3-dimethylaminopropyl)carbodiimide hydrochloride
FC—flash chromatography
HATU—2-(1H-7-Azabenzotriazol-1-yl)-1,1,3,3-tetramethyl uronium hexafluorophosphate methanaminium
NBS—N-bromosuccinamide;
NIS—N-iodosuccinimide
NMP—N-methyl-2-pyrrolidone;
TEA—triethylamine;
TFA—trifluoro acetic acid
THF—tetrahydrofuran;
PE—petroleum ether;
DIBAL-H—diisobutylaluminum hydride;
9-BBN—9-borabicyclo[3,3,1]nonane;

EXAMPLES

The following synthetic processes and examples are provided to more specifically illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

D1

6-((3-hydroxypropyl)(methyl)amino)pyrimidine-2,4 (1H,3H)-dione

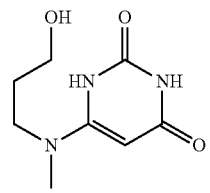

3-(Methylamino)propan-1-ol (588 mg, 6.6 mmol), 6-chloropyrimidine-2,4(1H,3H)-dione (440 mg, 3.0 mmol), KI (4.98 mg, 0.03 mmol) and water (6 mL) were added to a microwave reaction tube. The mixture was heated to 120° C. by microwave radiation (Biotage Initiator) and stirred for 2 h at 120° C. The reaction mixture was purified by Mass Directed Auto Prep to give 6-((3-hydroxypropyl)(methyl)amino)pyrimidine-2,4(1H,3H)-dione, trifluoroacetic acid salt (538 mg, 1.718 mmol, 57.3% yield) as a white solid.

LC-MS (ESI): m/z 200 [M+H]$^+$; 0.46 min (ret time).

D2

1-methyl-3,4-dihydro-1H-pyrimido[1,6-a]pyrimidine-6,8(2H,7H)-dione

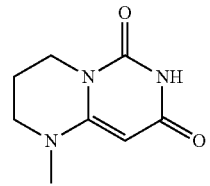

Ph$_3$P (854 mg, 3.26 mmol) was added to a suspension of 6-(3-hydroxypropyl)(methyl)amino)pyrimidine-2,4(1H, 3H)-dione, trifluoroacetic acid salt (340 mg, 1.085 mmol) in THF (140 mL) at room temperature, then DIAD (0.633 mL, 3.26 mmol) was added dropwise. The reaction mixture was stirred at room temperature for 3 h. The reaction mixture was concentrated in vacuo and the resulting residue was partitioned between diethyl ether and water. The aqueous phase was separated, washed with ethyl ether again, and then concentrated in vacuo to afford 1-methyl-3,4-dihydro-1H-pyrimido[1,6-a]pyrimidine-6,8(2H,7H)-dione, trifluoroacetic acid salt as an off-white solid (278 mg, 0.942 mmol, 87% yield).

LC-MS (ESI): m/z 182 [M+H]$^+$; 0.77 min (ret time).

D3

8-chloro-1-methyl-3,4-dihydro-1H-pyrimido[1,6-a]pyrimidin-6(2H)-one

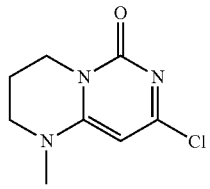

A suspension of 1-methyl-3,4-dihydro-1H-pyrimido[1,6-a]pyrimidine-6,8(2H,7H)-dione trifluoroacetic acid salt (0.253 g, 0.857 mmol) in POCl$_3$ (12 mL, 129 mmol) was stirred at 90° C. for 6 hr. After heating, the original suspension turned into a homogeneous solution. The mixture was concentrated in vacuo to remove POCl$_3$. Ice water was added to the resultant residue, and then solid NaOH was added dropwise to adjust pH to ~12. The solution was stirred at rt for 2 h. Aqueous HCl (1M) was added to adjust pH to ~7. The solution was subject to Mass Directed AutoPrep to give 8-chloro-1-methyl-3,4-dihydro-1H-pyrimido[1,6-a]pyrimidin-6(2H)-one, trifluoroacetic acid salt (260 mg, 0.829 mmol, 97% yield) as a white solid.

LC-MS (ESI): m/z 200 [M+H]$^+$; 0.52 min (ret time).

D4

5-Formyl-2-{[3-(trifluoromethyl)phenyl]oxy}benzonitrile

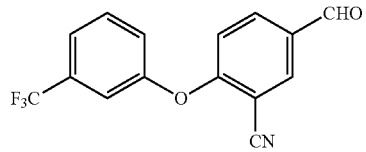 [SMILES: N#Cc1cc(C=O)ccc1Oc1cccc(C(F)(F)F)c1]

Potassium carbonate (1.85 g, 13.41 mmol) was added to a solution of 2-fluoro-5-formylbenzonitrile (2.0 g, 13.41 mmol) and 3-trifluoromethyl-phenol (1.63 mL, 13.41 mmol) in DMF (10 mL). The reaction mixture was stirred at 60° C. for 2 h with microwave radiation. The resultant mixture was filtered, and then concentrated. Purification via FC afforded the title compound as a white solid (3 g, 73% yield).

LC-MS (ESI): m/z 292[M+H]$^+$, 3.38 min (ret time).

D5

5-(Hydroxymethyl)-2-{[3-(trifluoromethyl)phenyl]oxy}benzonitrile

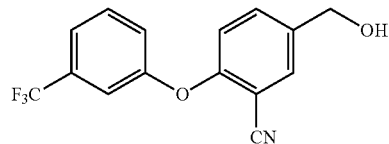 [SMILES: N#Cc1cc(CO)ccc1Oc1cccc(C(F)(F)F)c1]

NaBH$_4$ (0.39 g, 10.30 mmol) was added to a solution of 5-formyl-2-{[3-(trifluoromethyl)phenyl]oxy}benzonitrile (5 g, 17.17 mmol) in methanol (30 mL) at 0° C., and then stirred at rt for 30 min. The reaction mixture was quenched by acetone and concentrated. The residue was purified via ISCO (DCM:MeOH=20:1) to afford the title compound as a clear oil (5.5 g, 95% yield).

LC-MS (ESI): m/z 294[M+H]$^+$, 3.09 min (ret time).
$^1$H NMR (400 MHz, CDCl$_3$) δ: 7.72 (s, 1H), 7.5 (m, 3H), 7.32 (s, 1H), 7.25 (s, 1H), 6.92 (d, J=8.8 Hz, 1H), 4.72 (s, 2H).

D6

2-Hydroxy-5-iodobenzonitrile

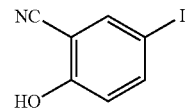

CF$_3$SO$_3$H (40 mL) was added dropwise to a solution of 2-hydroxy-benzonitrile (47.6 g, 0.400 mmol) in CH$_3$CN (500 mL) at 0° C., and then stirred at 0° C. for 20 min, then NIS (108 g, 0.48 mmol) was added. The reaction mixture was stirred at rt overnight, concentrated, then diluted with H$_2$O (300 mL) and extracted with EA (300 mL×3). The combined organic parts were dried over anhydrous Na$_2$SO$_4$, filtered, and concentrated. Purification via FC (PE/EtOAc=5/1) afforded the title compound as a white solid (80 g).

$^1$H NMR (400 MHz, CDCl$_3$) δ: 7.78 (s, 1H), 7.70 (d, J=8.4 Hz, 1H), 6.77 (d, J=8.8 Hz, 1H).

D7

5-Iodo-2-((5-(trifluoromethyl)pyridin-2-yl)oxy)benzonitrile

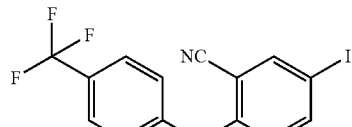

K$_2$CO$_3$ (91.0 g, 0.656 mol) was added to a solution of 2-hydroxy-5-iodo-benzonitrile (80.0 g, 0.328 mol) and 2-chloro-5-tri-fluoromethyl-pyridine (60.0 g, 0.328 mol) in DMF (500 ml) was added. The reaction mixture was refluxed overnight, filtered and concentrated. Purification via FC (PE/EtOAc=10/1) afforded the title product as a white solid (120 g).

$^1$H NMR (400 MHz, CDCl$_3$) δ: 8.38 (s, 1H), 8.01 (m, 2H), 7.95 (d, J=8.0 Hz, 1H), 7.22 (d, J=8.4 Hz, 1H), 8.08 (d, J=8.8 Hz, 1H), 7.68 (s, 1H).

D8

Methyl 3-cyano-4-((5-(trifluoromethyl)pyridin-2-yl)oxy)benzoate

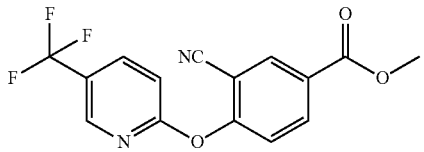 [SMILES: COC(=O)c1ccc(Oc2ccc(C(F)(F)F)cn2)c(C#N)c1]

Pd(dppf)Cl$_2$ (20 g) was added to a solution of 5-iodo-2-(5-trifluoromethyl-pyridin-2-yloxy)-benzonitrile (110 g, 0.29 mol) in methanol (1500 mL) and DMF (400 mL). The reaction mixture was stirred in an autoclave (10 L) at 100° C. under CO (1 MPa) for 72 hours. The methanol and DMF were removed in vacuo. Purification via FC (PE:EtOAc=20:1 to 10:1) afforded the title compound as a yellow oil (45 g, 48%).

$^1$H NMR (400 MHz, CDCl$_3$) δ: 8.39 (s, 1H), 8.29 (d, J=8.8 Hz, 1H), 8.01 (d, J=8.8 Hz, 1H), 7.40 (d, J=8.8 Hz, 1H), 7.27 (d, J=8.4 Hz, 1H), 3.94 (s, 3H).

D9

5-(Hydroxymethyl)-2-((5-(trifluoromethyl)pyridin-2-yl)oxy)benzonitrile

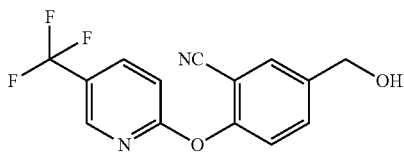 [SMILES: N#Cc1cc(CO)ccc1Oc1ccc(C(F)(F)F)cn1]

To a solution of 3-cyano-4-(5-trifluoromethyl-pyridin-2-yloxy)-benzoic acid methyl ester (23 g, 0.070 mol) in anhydrous THF (200 mL), was added LiAlH$_4$ (4.07 g, 0.11 mmol) portionwise at −78° C. The reaction mixture was warmed to −55° C. slowly and stirred for 20 mins, diluted with water (3 mL 0.16 mmol, slow addition), filtered and concentrated. Purification via FC (PE/EtOAc=10/1 to 5/1) afforded the title product as a colorless oil (12.5 g).

$^1$H NMR (400 MHz, CDCl$_3$) δ: 8.37 (s, 1H), 7.98 (d, J=8.8 Hz, 1H), 7.72 (s, 1H), 7.64 (d, J=8.4 Hz, 1H), 7.29 (d, J=8.8 Hz, 1H), 7.19 (d, J=8.4 Hz, 1H).

D10

3,5-difluoro-4-((6-(trifluoromethyl)-3-pyridinyl)oxy)benzaldehyde

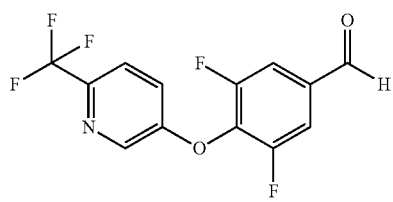 [SMILES: O=Cc1cc(F)c(Oc2ccc(C(F)(F)F)nc2)c(F)c1]

3,4,5-trifluorobenzaldehyde (1 g, 6.25 mmol), which is commercially available 6-(trifluoromethyl)-3-pyridinol (1.019 g, 6.25 mmol) and K$_2$CO$_3$ (1.727 g, 12.49 mmol) were added into a microwave vial. Then, N,N-dimethylformamide (DMF) (15 mL) was added. The microwave vial was sealed and heated in Biotage Initiator at 100° C. for 1 h. The mixture was extracted with by EtOAc. The organic extracts were dried over Na$_2$SO$_4$ and evaporated to give 1.78 g of the title product (94%).

LC-MS (ESI): m/z 304[M+H]$^+$, 3.31 min (ret time).

D11

(3,5-difluoro-4-((6-(trifluoromethyl)-3-pyridinyl)oxy)phenyl)methanol

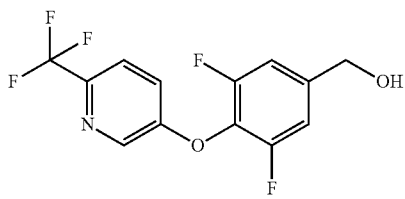 [SMILES: OCc1cc(F)c(Oc2ccc(C(F)(F)F)nc2)c(F)c1]

To a solution of 3,5-difluoro-4-((6-(trifluoromethyl)pyridin-3-yl)oxy)benzaldehyde (1.78 g, 5.87 mmol) in methanol (15 mL) was added NaBH$_4$ (0.222 g, 5.87 mmol). The mixture was stirred at room temp for 0.5 h. NH$_4$Cl solution was added to the reaction mixture, and the reaction mixture was extracted by DCM. The organic phase was then dried over Na$_2$SO$_4$ and evaporated to give the product (1.702 g, 95%).

LC-MS (ESI): m/z 306[M+H]$^+$, 3.02 min (ret time).

D12

3-fluoro-4-((6-(trifluoromethyl)-3-pyridinyl)oxy)benzaldehyde

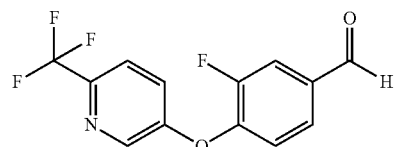

The title compound was prepared by a procedure similar to that described for D4 starting from 6-(trifluoromethyl)3-pyridinol and 3,4-difluorobenzaldehyde.

LC-MS (ESI): m/z 286[M+H]$^+$, 3.20 min (ret time).

D13

(3-fluoro-4-((6-(trifluoromethyl)-3-pyridinyl)oxy)phenyl)methanol

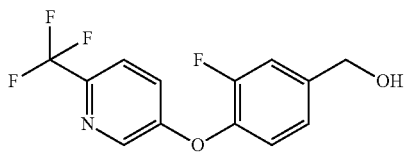 [SMILES: OCc1ccc(Oc2ccc(C(F)(F)F)nc2)c(F)c1]

The title compound was prepared by a procedure similar to that described for D5 starting from 3-fluoro-4-((6-(trifluoromethyl)-3-pyridinyl)oxy)benzaldehyde.

LC-MS (ESI): m/z 288[M+H]$^+$, 2.88 min (ret time).

D14

4-(3,4-fluorophenoxy)-3-fluoro-benzaldehyde

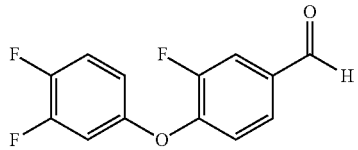 [SMILES: O=Cc1ccc(Oc2ccc(F)c(F)c2)c(F)c1]

The title compound was prepared by a procedure similar to that described for D4 starting from 3,4-difluorophenol and 3,4-difluorobenzaldehyde.

LC-MS (ESI): m/z 253[M+H]$^+$, 3.34 min (ret time).

D15

(4-(3,4-fluorophenoxy)-3-fluorophenyl)methanol

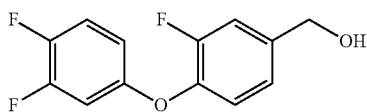 [SMILES: OCc1ccc(Oc2ccc(F)c(F)c2)c(F)c1]

The title compound was prepared by a procedure similar to that described for D5 starting from 4-(3,4-fluorophenoxy)-3-fluoro-benzaldehyde.

LC-MS (ESI): m/z 237[M−17]$^+$, 2.99 min (ret time).

D16

4-(4-Chloro-3-(trifluoromethyl)phenoxy)benzaldehyde

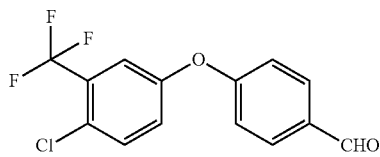 [SMILES: O=Cc1ccc(Oc2ccc(Cl)c(C(F)(F)F)c2)cc1]

The title compound was prepared by a procedure similar to that described for D4 starting from 4-chloro-3-trifluoromethyl-phenol and 4-fluoro-benzaldehyde.

LC-MS (ESI): m/z 301 [M+1]$^+$; 3.79 min (ret time).

D17

(4-(4-Chloro-3-(trifluoromethyl)phenoxy)phenyl)methanol

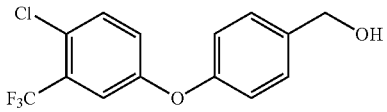

The title compound was prepared by a procedure similar to that described for D5 starting from 4-(4-Chloro-3-(trifluoromethyl)phenoxy)benzaldehyde.

LC-MS (ESI): m/z 285[M−17]$^+$, 3.48 min (ret time).

D18

4-(3,4-dichlorophenoxy)benzaldehyde

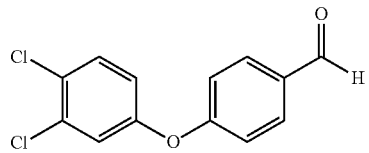 [SMILES: O=Cc1ccc(Oc2ccc(Cl)c(Cl)c2)cc1]

The title compound was prepared by a procedure similar to that described for D4 starting from 3,4-dichlorophenol and 4-fluoro-benzaldehyde.

LC-MS (ESI): m/z 268 [M+1]$^+$; 3.79 min (ret time).

D19

(4-(3,4-dichlorophenoxy)phenyl)methanol

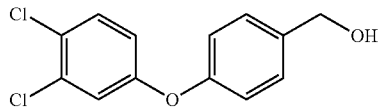 [SMILES: OCc1ccc(Oc2ccc(Cl)c(Cl)c2)cc1]

The title compound was prepared by a procedure similar to that described for D5 starting from 4-(3,4-dichlorophenoxy)benzaldehyde.

LC-MS (ESI): m/z 251[M−17]$^+$, 3.42 min (ret time).

D20

(E)-1-chloro-4-(4-(2-nitrovinyl)phenoxy)-2-(trifluoromethyl)benzene

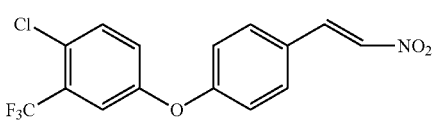 [SMILES: O=[N+]([O-])/C=C/c1ccc(Oc2ccc(Cl)c(C(F)(F)F)c2)cc1]

To a solution of 4-(4-Chloro-3-(trifluoromethyl)phenoxy)benzaldehyde (13 g, 43.2 mmol) and ammonium acetate (1.67 g, 21.62 mmol) in HOAc (40 mL), was added nitromethane (6.99 mL, 130 mmol). The reaction mixture was stirred at 120° C. for 5 h, and concentrated. The residue was dissolved in DCM (150 mL), washed with sat. aqueous NaHCO$_3$ (100 mL×2), brine and then, dried over anhydrous Na$_2$SO$_4$ and concentrated to afford the title compound as a brown solid (14.3 g, 63% yield).

LC-MS (ESI): No MS signal, 1.97 min (ret time).

D21

1-chloro-4-(4-(2-nitroethyl)phenoxy)-2-(trifluoromethyl)benzene

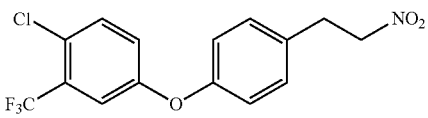 [SMILES: O=[N+]([O-])CCc1ccc(Oc2ccc(Cl)c(C(F)(F)F)c2)cc1]

To a suspension of (E)-1-chloro-4-(4-(2-nitrovinyl)phenoxy)-2-(trifluoromethyl)benzene (13 g, 43.2 mmol) and silica gel (120 g, 100-200 Mesh) in i-PrOH (155 mL) and CHCl$_3$ (465 mL), was added NaBH$_4$ (13.65 g, 361 mmol) portionwise. The reaction mixture was stirred overnight at rt, filtered, and washed with DCM (1 L). The organic phase was washed with sat. NaHCO$_3$ (200 mL), then brine, and dried over anhydrous Na$_2$SO$_4$ and concentrated to afford the title compound as a brown liquid (26 g, 50% yield).
LC-MS (ESI): No MS signal, 1.70 min (ret time).

D22

2-(4-(4-chloro-3-(trifluoromethyl)phenoxy)phenyl)ethanamine

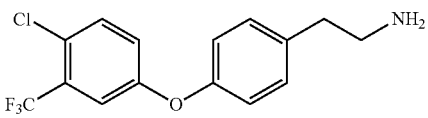 [SMILES: NCCc1ccc(Oc2ccc(Cl)c(C(F)(F)F)c2)cc1]

To a solution of 1-chloro-4-(4-(2-nitroethyl)phenoxy)-2-(trifluoromethyl)benzene (21 g, 60.7 mmol) and ammonium formate (30.6 g, 486 mmol) in methanol (250 mL) and water (250 mL), was added zinc powder (15.89 g, 243 mmol). The reaction mixture was stirred at 80° C. for 2 h, filtered through a glass grit and washed with methanol. The filtrate was concentrated and the residue was extracted with DCM (200 mL), and then washed with sat. NaHCO$_3$ (100 mL), brine, and dried over anhydrous Na$_2$SO$_4$ and concentrated. Purification via FC (DCM/CH$_3$OH=100/8) afforded the title compound (7.0 g) as a yellow oil.
LC-MS (ESI): m/z 316[M+H]$^+$, 1.15 min (ret time).

D23

3-fluoro-4-(4-fluoro-3-(trifluoromethyl)phenoxy)benzaldehyde

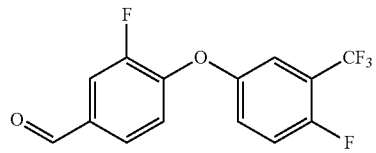 [SMILES: O=Cc1ccc(Oc2ccc(F)c(C(F)(F)F)c2)c(F)c1]

The title compound was prepared by a procedure similar to that described for D4 starting from 4-fluoro-3-(trifluoromethyl)phenol and 3,4-difluorobenzaldehyde.
LC-MS (ESI): m/z 303 [M+H]$^+$; 3.65 min (ret time).

D24

(3-fluoro-4-(4-fluoro-3-(trifluoromethyl)phenoxy)phenyl)methanol

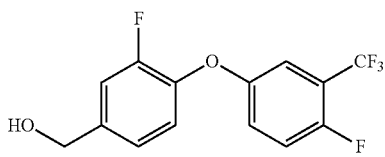 [SMILES: OCc1ccc(Oc2ccc(F)c(C(F)(F)F)c2)c(F)c1]

The title compound was prepared by a procedure similar to that described for D5 starting from 3-fluoro-4-(4-fluoro-3-(trifluoromethyl)phenoxy)benzaldehyde.
LC-MS (ESI): m/z 287[M−17]$^+$, 3.32 min (ret time).

D25

4-(3,4-difluorophenoxy)benzaldehyde

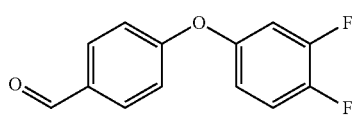 [SMILES: O=Cc1ccc(Oc2ccc(F)c(F)c2)cc1]

The title compound was prepared by a procedure similar to that described for D4 starting from 3,4-difluorophenol and 4-fluorobenzaldehyde.
LC-MS (ESI): m/z 235 [M+H]$^+$; 3.38 min (ret time).

D26

(4-(3,4-difluorophenoxy)phenyl)methanol

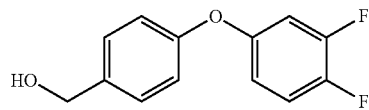 [SMILES: OCc1ccc(Oc2ccc(F)c(F)c2)cc1]

The title compound was prepared by a procedure similar to that described for D5 starting from 4-(3,4-difluorophenoxy)benzaldehyde.
LC-MS (ESI): m/z 219[M−17]$^+$, 3.02 min (ret time).

D27

4-(3-chloro-4-fluorophenoxy)-3-fluorobenzaldehyde

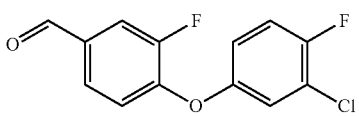 [SMILES: O=Cc1ccc(Oc2ccc(F)c(Cl)c2)c(F)c1]

The title compound was prepared by a procedure similar to that described for D4 starting from 3-chloro-4-fluorophenol and 3,4-difluorobenzaldehyde.
LC-MS (ESI): m/z 269 [M+1]$^+$; 3.60 min (ret time).

D28

(4-(3-chloro-4-fluorophenoxy)-3-fluorophenyl)methanol

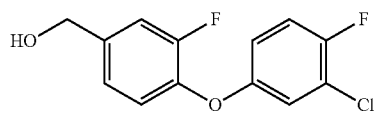 [SMILES: OCc1ccc(Oc2ccc(F)c(Cl)c2)c(F)c1]

The title compound was prepared by a procedure similar to that described for D5 starting from 4-(3-chloro-4-fluorophenoxy)-3-fluorobenzaldehyde.
LC-MS (ESI): m/z 271 [M+1]$^+$; 3.20 min (ret time).

D29

4-(3-chlorophenoxy)-3-fluorobenzaldehyde

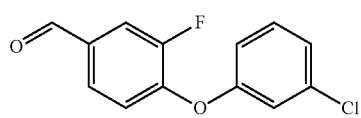 [SMILES: O=Cc1ccc(Oc2cccc(Cl)c2)c(F)c1]

The title compound was prepared by a procedure similar to that described for D4 starting from 3,4-difluorobenzaldehyde and 3-chlorophenol.
LC-MS (ESI): m/z 251 [M+1]$^+$; 3.58 min (ret time).

D30

(4-(3-chlorophenoxy)-3-fluorophenyl)methanol

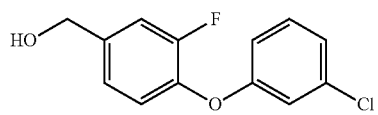 [SMILES: OCc1ccc(Oc2cccc(Cl)c2)c(F)c1]

The title compound was prepared by a procedure similar to that described for D5 starting from 4-(3-chlorophenoxy)-3-fluorobenzaldehyde.
LC-MS (ESI): m/z 253 [M+1]$^+$; 3.24 min (ret time).

D31

4-(3-chloro-4-fluorophenoxy)benzaldehyde

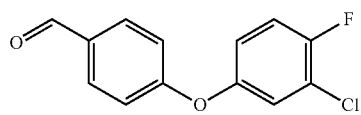 [SMILES: O=Cc1ccc(Oc2ccc(F)c(Cl)c2)cc1]

The title compound was prepared by a procedure similar to that described for D4 starting from 4-fluorobenzaldehyde and 3-chloro-4-fluorophenol.
LC-MS (ESI): m/z 251 [M+1]$^+$; 3.58 min (ret time).

D32

(4-(3-chloro-4-fluorophenoxy)phenyl)methanol

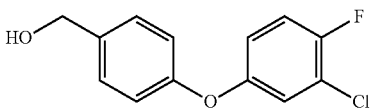 [SMILES: OCc1ccc(Oc2ccc(F)c(Cl)c2)cc1]

The title compound was prepared by a procedure similar to that described for D5 starting from 4-(3-chloro-4-fluorophenoxy)benzaldehyde.
LC-MS (ESI): m/z 253 [M+1]$^+$; 3.20 min (ret time).

D33

3-fluoro-4-(3-fluorophenoxy)benzaldehyde

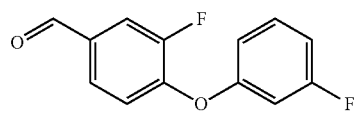 [SMILES: O=Cc1ccc(Oc2cccc(F)c2)c(F)c1]

The title compound was prepared by a procedure similar to that described for D4 starting from 3,4-difluorobenzaldehyde and 3-fluorophenol.
LC-MS (ESI): m/z 235 [M+1]$^+$; 3.37 min (ret time).

D34

(3-fluoro-4-(3-fluorophenoxy)phenyl)methanol

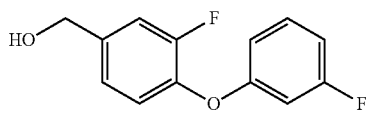 [SMILES: OCc1ccc(Oc2cccc(F)c2)c(F)c1]

The title compound was prepared by a procedure similar to that described for D5 starting from 3-fluoro-4-(3-fluorophenoxy)benzaldehyde.
LC-MS (ESI): m/z 219 [M+1]$^+$; 2.99 min (ret time).

D35

4-phenoxybenzaldehyde

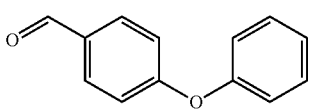 [SMILES: O=Cc1ccc(Oc2ccccc2)cc1]

The title compound was prepared by a procedure similar to that described for D4 starting from 4-fluorobenzaldehyde and phenol.
LC-MS (ESI): m/z 199 [M+1]$^+$; 3.05 min (ret time).

D36

(4-phenoxyphenyl)methanol

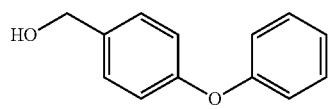 [SMILES: OCc1ccc(Oc2ccccc2)cc1]

The title compound was prepared by a procedure similar to that described for D5 starting from (4-phenoxyphenyl)methanol.
LC-MS (ESI): m/z 201 [M+1]$^+$; 2.82 min (ret time).

D37

3-fluoro-4-(3-(trifluoromethyl)phenoxy)benzaldehyde

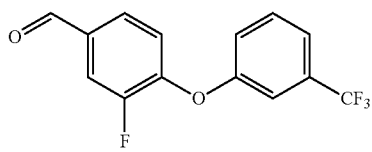 [SMILES: O=Cc1ccc(Oc2cccc(C(F)(F)F)c2)c(F)c1]

The title compound was prepared by a procedure similar to that described for D4 starting from 3,4-difluorobenzaldehyde and 3-(trifluoromethyl)phenol.
LC-MS (ESI): m/z 285 [M+1]$^+$; 3.64 min (ret time).

D38

(3-fluoro-4-(3-(trifluoromethyl)phenoxy)phenyl)methanol

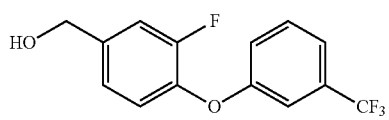

The title compound was prepared by a procedure similar to that described for D5 starting from 3-fluoro-4-(3-(trifluoromethyl)phenoxy)benzaldehyde.
LC-MS (ESI): m/z 287 [M+1]$^+$; 3.30 min (ret time).

D39

5-formyl-2-(4-(trifluoromethyl)phenoxy)benzonitrile

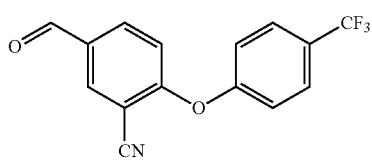 [SMILES: N#Cc1cc(C=O)ccc1Oc1ccc(C(F)(F)F)cc1]

The title compound was prepared by a procedure similar to that described for D4 starting from 2-fluoro-5-formylbenzonitrile and 4-(trifluoromethyl)phenol.
LC-MS (ESI): m/z 292 [M+1]$^+$; 3.41 min (ret time).

D40

5-(hydroxymethyl)-2-(4-(trifluoromethyl)phenoxy)benzonitrile

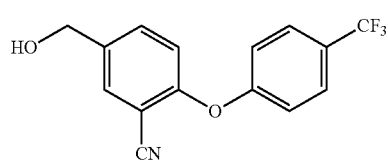 [SMILES: N#Cc1cc(CO)ccc1Oc1ccc(C(F)(F)F)cc1]

The title compound was prepared by a procedure similar to that described for D5 starting from 5-(hydroxymethyl)-2-(4-(trifluoromethyl)phenoxy)benzonitrile.
LC-MS (ESI): m/z 294 [M+1]$^+$; 3.13 min (ret time).

D41

2-(4-fluorophenoxy)-5-formylbenzonitrile

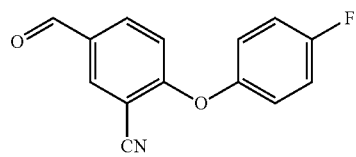 [SMILES: N#Cc1cc(C=O)ccc1Oc1ccc(F)cc1]

The title compound was prepared by a procedure similar to that described for D4 starting from 2-fluoro-5-formylbenzonitrile and 4-fluorophenol.
LC-MS (ESI): m/z 242 [M+1]$^+$; 3.12 min (ret time).

D42

2-(4-fluorophenoxy)-5-(hydroxymethyl)benzonitrile

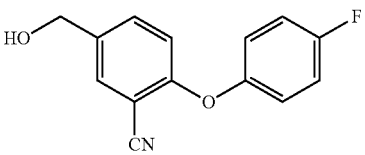 [SMILES: N#Cc1cc(CO)ccc1Oc1ccc(F)cc1]

The title compound was prepared by a procedure similar to that described for D5 starting from 2-(4-fluorophenoxy)-5-(hydroxymethyl)benzonitrile.
LC-MS (ESI): m/z 244 [M+1]$^+$; 2.80 min (ret time).

D43

3-fluoro-4-((6-(trifluoromethyl)pyridin-2-yl)oxy)
benzaldehyde

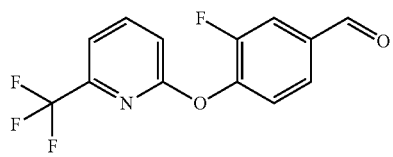 [SMILES: O=Cc1ccc(Oc2cccc(C(F)(F)F)n2)c(F)c1]

The title compound was prepared by a procedure similar to that described for D4 starting from 3-fluoro-4-hydroxybenzaldehyde and 2-chloro-6-(trifluoromethyl)pyridine.

LC-MS (ESI): m/z 286 [M+H]+; 3.34 min (ret time).

D44

(3-fluoro-4-((6-(trifluoromethyl)pyridin-2-yl)oxy)
phenyl)methanol

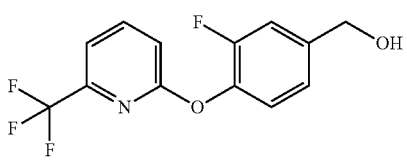 [SMILES: OCc1ccc(Oc2cccc(C(F)(F)F)n2)c(F)c1]

The title compound was prepared by a procedure similar to that described for D5 starting from 3-fluoro-4-((6-(trifluoromethyl)pyridin-2-yl)oxy)benzaldehyde.

LC-MS (ESI): m/z 288 [M+H]+; 2.98 min (ret time)

D45

3-fluoro-5-(hydroxymethyl)benzonitrile

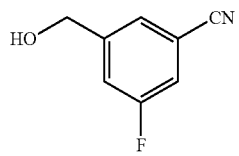 [SMILES: N#Cc1cc(F)cc(CO)c1]

The title compound was prepared by a procedure similar to that described for D5 starting from methyl 3-cyano-5-fluorobenzoate.

LC-MS (ESI): m/z 152 [M+1]+; 1.84 min (ret time).

D46

2-(3,4-difluorophenoxy)-5-formylbenzonitrile

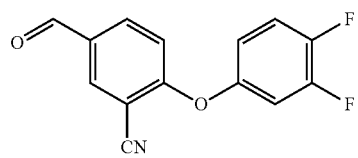 [SMILES: N#Cc1cc(C=O)ccc1Oc1ccc(F)c(F)c1]

The title compound was prepared by a procedure similar to that described for D4 starting from 2-fluoro-5-formylbenzonitrile and 3,4-difluorophenol.

LC-MS (ESI): m/z 260 [M+1]+; 3.15 min (ret time).

D47

2-(3,4-difluorophenoxy)-5-(hydroxymethyl)benzonitrile

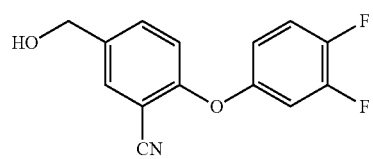 [SMILES: N#Cc1cc(CO)ccc1Oc1ccc(F)c(F)c1]

The title compound was prepared by a procedure similar to that described for D5 starting from 2-(3,4-difluorophenoxy)-5-formylbenzonitrile.

LC-MS (ESI): m/z 262 [M+1]+; 2.86 min (ret time).

D48

5-bromo-2-(3,4-difluorophenoxy)pyridine

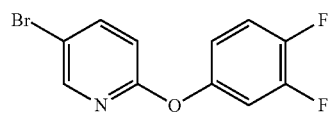 [SMILES: Fc1ccc(Oc2ccc(Br)cn2)cc1F]

To a solution of 5-bromo-2-fluoropyridine (19 g, 108 mmol) and 3,4-difluorophenol (14.05 g, 108 mmol) in dimethyl sulfoxide (DMSO) (150 mL) was added potassium carbonate (26.9 g, 194 mmol). The reaction mixture was stirred at 80° C. for 2 hr, then H₂O (200 ml) and EtOAc (200 ml) were added. The organic layer was separated, and then concentrated under reduced pressure. The crude product was purified by a silica gel chromatography eluting with Hex/EtOAc (10:1) to provide 5-bromo-2-(3,4-difluorophenoxy)pyridine (19 g, 55.4%).

LC-MS (ESI): m/z 286 [M+1]+; 1.25 min (ret time).

D49

2-(3,4-difluorophenoxy)-5-iodopyridine

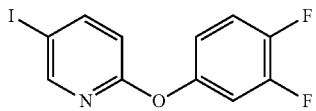 [SMILES: Fc1ccc(Oc2ccc(I)cn2)cc1F]

To a solution of 5-bromo-2-(3,4-difluorophenoxy)pyridine (19 g, 66.4 mmol) in tetrahydrofuran (THF) (200 mL) was added isopropylmagnesium chloride (66.4 mL, 66.4 mmol). The reaction mixture was stirred at 20° C. for 2 hr, and then $I_2$ (16.86 g, 66.4 mmol) was added, The reaction mixture was stirred at 20° C. for another 4 hr, then saturated aqueous $NH_4Cl$ solution (200 ml) and EtOAc (200 ml) were added, the organic layer was separated, and concentrated under reduced pressure. The crude product was purified by silica gel chromatography eluting with Hex/EtOAc (20:1). The collected fractions provided 2-(3,4-difluorophenoxy)-5-iodopyridine (22 g, 61.7%).

LC-MS (ESI): m/z 334 [M+H]$^+$; 1.25 min (ret time).

D50 diethyl 2-(6-(3,4-difluorophenoxy)pyridin-3-yl)malonate

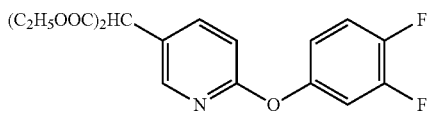

To a suspension of 2-(3,4-difluorophenoxy)-5-iodopyridine (22 g, 41.0 mmol), diethyl malonate (6.56 g, 41.0 mmol) and $Cs_2CO_3$ (13.34 g, 41.0 mmol) in 1,4-dioxane (200 mL) was added picolinic acid (5.04 g, 41.0 mmol) and copper(I) iodide (7.80 g, 41.0 mmol). The reaction mixture was stirred at 80° C. for 10 hr. and then concentrated under reduced pressure. The residue was extracted with $CH_2Cl_2$, and then the organic layer was separated and concentrated under reduced pressure to provide diethyl 2-(6-(3,4-difluorophenoxy)pyridin-3-yl)malonate (25 g, 85%).

LC-MS (ESI): m/z 366 [M+H]$^+$; 1.23 min (ret time).

D51

2-(6-(3,4-difluorophenoxy)pyridin-3-yl)acetic acid

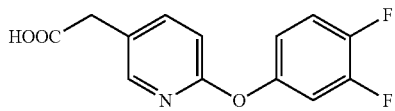 [SMILES: O=C(O)Cc1ccc(Oc2ccc(F)c(F)c2)nc1]

To a solution of diethyl 2-(6-(3,4-difluorophenoxy)pyridin-3-yl)malonate (25 g, 34.9 mmol) in ethanol (250 mL) was added potassium hydroxide (19.58 g, 349 mmol). The reaction mixture was stirred at 80° C. for 1 hr. and then the reaction mixture was concentrated under the reduced pressure. To the residue was added 10% HCl to adjust the solution to approximately pH 7. Then, the solution was extracted with EtOAc (300 mL), and the organic layer was separated, and dried over $Na_2SO_4$, and then concentrated under reduced pressure to give 2-(6-(3,4-difluorophenoxy)pyridin-3-yl)acetic acid (10 g, 98%).

LC-MS (ESI): m/z 266 [M+H]$^+$; 1.01 min (ret time).

D52 ethyl 2-(6-(3,4-difluorophenoxy)pyridin-3-yl)acetate

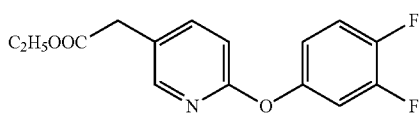

To a solution of 2-(6-(3,4-difluorophenoxy)pyridin-3-yl)acetic acid (10 g, 37.7 mmol) in ethanol (100 mL) was added sulfuric acid (20 ml, 375 mmol) in ethanol (100 mL). The reaction mixture was stirred at 80° C. for 3 hr. and then the reaction mixture was made alkali with $Na_2CO_3$, and then extracted with $CH_2Cl_2$. The organic layer was separated and dried over $Na_2SO_4$, and then concentrated under reduced pressure to provide ethyl 2-(6-(3,4-difluorophenoxy)pyridin-3-yl)acetate (10 g, 78%).

LC-MS (ESI): m/z 294 [M+H]$^+$; 1.17 min (ret time).

D53

2-(6-(3,4-difluorophenoxy)pyridin-3-yl)ethanol

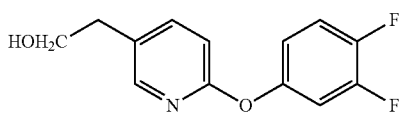 [SMILES: OCCc1ccc(Oc2ccc(F)c(F)c2)nc1]

The title compound was prepared by a procedure similar to that described for D5 starting from ethyl 2-(6-(3,4-difluorophenoxy)pyridin-3-yl)acetate.

LC-MS (ESI): m/z 252 [M+H]$^+$; 0.99 min (ret time).

D54

5-(((2,6-dichloropyrimidin-4-yl)oxy)methyl)-2-(3-(trifluoromethyl)phenoxy)benzonitrile

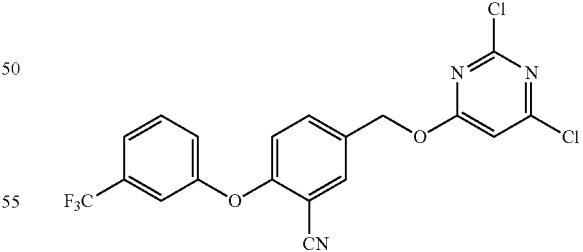

To a suspension of NaH (0.532 g, 13.30 mmol) in N, N-dimethylformamide (6 ml) was added 2,4,6-trichloropyrimidine (1.057 g, 5.76 mmol) at 0° C. The reaction mixture was stirred for 5 min at room temperature, and then dropwise was added to a solution of 5-(hydroxymethyl)-2-(3-(trifluoromethyl)phenoxy)benzonitrile (1.3 g, 4.43 mmol) in N, N-dimethylformamide (6 ml). The reaction mixture was stirred for another 1 h at room temperature. Then, the reaction mixture was quenched with water and the solution was purified with reverse phase column chromatography (120 g) using water/MeCN as eluent to afford 5-(((2,6-dichloropyrimidin-4-yl)oxy)methyl)-2-(3-(trifluoromethyl)phenoxy)benzonitrile (1.4 g, 3.18 mmol, 71.7% yield).

LC-MS (ESI): m/z 440 [M+1]$^+$; 4.11 min (ret time).

D55

5-(((6-((3-bromopropyl)amino)-2-chloropyrimidin-4-yl)oxy)methyl)-2-(3-(trifluoromethyl)phenoxy)benzonitrile

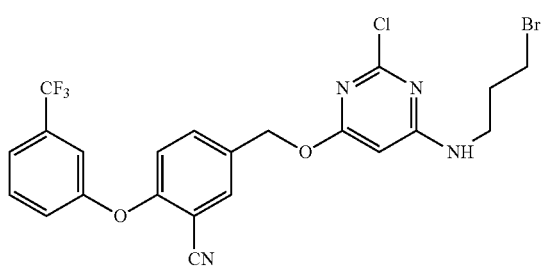 [SMILES: N#Cc1cc(COc2cc(NCCCBr)nc(Cl)n2)ccc1Oc1cccc(C(F)(F)F)c1]

To a solution of 5-(((2,6-dichloropyrimidin-4-yl)oxy)methyl)-2-(3-(trifluoromethyl)phenoxy)benzonitrile (600 mg, 1.363 mmol) and DIPEA (1.5 mL, 8.59 mmol) in N,N-dimethylformamide (3 ml) was added 3-bromopropan-1-amine hydrobromide (900 mg, 4.11 mmol) at 0° C. and the reaction mixture was stirred overnight at 0° C. The solution was purified with reverse phase column chromatography (120 g) using water (contained 0.3% TFA) and MeCN as eluent to afford 5-(((6-(3-bromopropyl)amino)-2-chloropyrimidin-4-yl)oxy)methyl)-2-(3-(trifluoromethyl)phenoxy)benzonitrile (350 mg, 0.646 mmol, 47.4% yield).

LC-MS (ESI): m/z 461 [M+1]$^+$; 3.00 min (ret time).

D56

5-(4-chloro-3-(trifluoromethyl)phenoxy)-2-nitropyridine

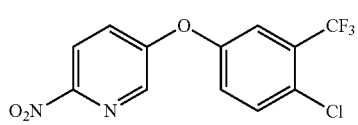 [SMILES: O=[N+]([O-])c1ccc(Oc2ccc(Cl)c(C(F)(F)F)c2)cn1]

To a solution of 5-bromo-2-nitropyridine (15 g, 73.9 mmol) and 4-chloro-3-(trifluoromethyl)phenol (14.52 g, 73.9 mmol) in acetonitrile (200 mL) was added potassium carbonate (18.38 g, 133 mmol) and the reaction mixture was stirred at 80° C. for 10 hr. Then, 200 mL of EtOAc and 200 mL of H$_2$O were added. The organic layer was separated and concentrated under reduced pressure. The crude product was purified by a silica gel column chromatography eluting and was eluted with Hex/EtOAc (5:1) to provide 5-(4-chloro-3-(trifluoromethyl)phenoxy)-2-nitropyridine (8 g, 32.8%), LC-MS (ESI): m/z 319 [M+1]$^+$; 1.23 min (ret time).

D57

5-(4-chloro-3-(trifluoromethyl)phenoxy)pyridin-2-amine

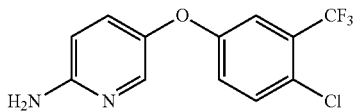

To a solution of 5-(4-chloro-3-(trifluoromethyl)phenoxy)-2-nitropyridine (8 g, 25.1 mmol) in ethanol (100 mL) was added tin (II) chloride dihydrate (56.7 g, 251 mmol). The reaction mixture was stirred at 80° C. for 2 hr. and poured into 500 mL of H$_2$O and adjusted to basic with 10% NaHCO$_3$. Then, the reaction mixture was extracted with 500 mL of EtOAc. The organic layer was separated, and then dried over Na$_2$SO$_4$, and concentrated under reduced pressure to give 5-(4-chloro-3-(trifluoromethyl)-phenoxy)pyridin-2-amine (6 g, 72.9%).

LC-MS (ESI): m/z 289 [M+1]$^+$; 0.98 min (ret time).

D58

5-(4-chloro-3-(trifluoromethyl)phenoxy)-2-iodopyridine

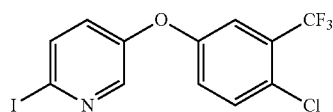 [SMILES: FC(F)(F)c1cc(Oc2ccc(I)nc2)ccc1Cl]

To a suspension of 5-(4-chloro-3-(trifluoromethyl)phenoxy)pyridin-2-amine (6 g, 20.79 mmol) in diiodomethane (50 g, 187 mmol) was added isoamyl nitrite (13.99 ml, 104 mmol). The reaction mixture was stirred at 80° C. for 2 hr. The crude product was purified by a silica gel column eluting with Hex/EtOAc (20:1) to provide the crude 5-(4-chloro-3-trifluoromethyl)phenoxy)-2-iodopyridine (6 g, 34.0%).

LC-MS (ESI): m/z 289 [M+1]$^+$; 1.32 min (ret time).

D59 diethyl 2-(5-(4-chloro-3-(trifluoromethyl)phenoxy)pyridin-2-yl)malonate

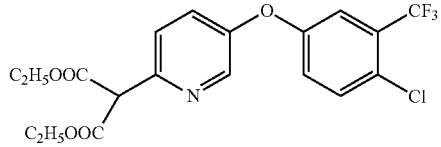

To a solution of 5-(4-chloro-3-(trifluoromethyl)phenoxy)-2-iodopyridine (6 g, 7.06 mmol), diethyl malonate (2.261 g, 14.12 mmol) and picolinic acid (0.261 g, 2.117 mmol) in 1,4-dioxane (60 mL) were added Cs$_2$CO$_3$ (6.90 g, 21.17 mmol) and copper(I) iodide (0.134 g, 0.706 mmol). The reaction mixture was stirred at 80° C. for 10 hr. and then concentrated under reduced pressure. The reaction mixture was then extracted with CH$_2$Cl$_2$. The organic layer was separated and concentrated under reduced pressure to provide the diethyl 2-(5-(4-chloro-3-(trifluoromethyl) phenoxy)pyridin-2-yl) malonate (6 g, 77%).

LC-MS (ESI): m/z 432 [M+1]$^+$; 1.48 min (ret time).

D60

2-(5-(4-chloro-3-(trifluoromethyl)phenoxy)pyridin-2-yl)acetic acid

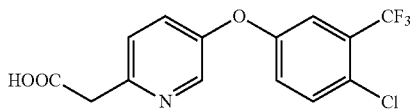 [SMILES: O=C(O)Cc1ccc(Oc2ccc(Cl)c(C(F)(F)F)c2)cn1]

To a solution of diethyl 2-(5-(4-chloro-3-(trifluoromethyl)phenoxy)pyridin-2-yl)malonate (6 g, 5.42 mmol) in ethanol (60 mL) was added potassium hydroxide (3.04 g, 54.2 mmol). The reaction mixture was stirred at 80° C. for 1 hr., and then concentrated under reduced pressure. The reaction mixture was adjusted to pH 7 with 10% aqueous HCl solution. The reaction mixture was extracted with 100 mL of EtOAc, and the organic layer was separated, dried over $Na_2SO_4$, and then concentrated under reduced pressure to provide 2-(5-(4-chloro-3-(trifluoromethyl)phenoxy)pyridin-2-yl)acetic acid (3 g, 100%).

LC-MS (ESI): m/z 332 $[M+1]^+$; 1.10 min (ret time).

D61 ethyl 2-(5-(4-chloro-3-(trifluoromethyl)phenoxy)pyridin-2-yl)acetate

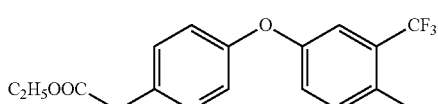

To a solution of 2-(5-(4-chloro-3-(trifluoromethyl)phenoxy)pyridin-2-yl)acetic acid (3 g, 5.61 mmol) in ethanol (30 mL) was added sulfuric acid (8 mL, 150 mmol) in ethanol (30 mL). The reaction mixture was stirred at 80° C. for 2 hr. Then 30 mL of 25% aqueous $NH_4OH$ solution and 50 mL $CH_2Cl_2$ were added to the reaction mixture. The organic layer was separated and dried over $Na_2SO_4$, and concentrated under reduced pressure to provide ethyl 2-(5-(4-chloro-3-(trifluoromethyl)phenoxy)pyridin-2-yl)acetate (2 g, 79%).

LC-MS (ESI): m/z 360 $[M+1]^+$; 1.24 min (ret time).

D62

2-(5-(4-chloro-3-(trifluoromethyl)phenoxy)pyridin-2-yl)ethanol

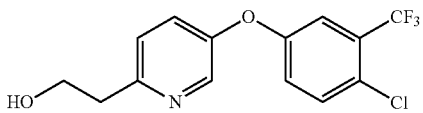 [SMILES: OCCc1ccc(Oc2ccc(Cl)c(C(F)(F)F)c2)cn1]

To a solution of ethyl 2-(5-(4-chloro-3-(trifluoromethyl)phenoxy)pyridin-2-yl)acetate (2 g, 4.45 mmol) in ethanol (20 mL) was added sodium borohydride (1.683 g, 44.5 mmol). The reaction mixture was stirred at 20° C. for 10 hr. To the reaction mixture was added 50 mL of $H_2O$ and 50 mL of $CH_2Cl_2$. The organic layer was separated and dried over $Na_2SO_4$ and concentrated under reduced pressure. The crude product was added to a prep HPLC column eluting with MeCN/TFA 0.1% to provide 2-(5-(4-chloro-3-(trifluoromethyl)phenoxy)pyridin-2-yl)ethanol (500 mg, 25.5%).

LC-MS (ESI): m/z 318 $[M+1]^+$; 1.00 min (ret time).

D63

4-{[4-chloro-3-(trifluoromethyl)phenyl]oxy}benzaldehyde

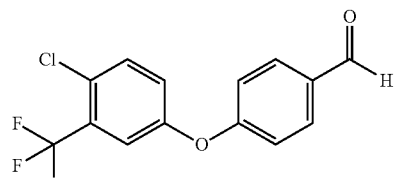

The title compound was prepared by a procedure similar to that described for D4 starting from 4-fluorobenzaldehyde and 4-chloro-3-(trifluoromethyl)phenol.

LC-MS (ESI): m/z 301 $[M+H]^+$; 3.76 min (ret time).

D64

4-chloro-3-(trifluoromethyl)phenyl 4-ethenylphenyl ether

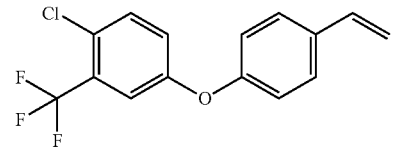 [SMILES: C=Cc1ccc(Oc2ccc(Cl)c(C(F)(F)F)c2)cc1]

To a suspension of methyl(triphenyl)phosphonium bromide (5.56 g, 15.57 mmol) in anhydrous tetrahydrofuran (THF) (50 mL), was added BuLi (9.5 ml, 15.20 mmol) dropwise at 0° C. After the reaction mixture had turned to clear solution it was stirred for 15 min at 0° C., then a solution of 4-{[4-chloro-3-(trifluoromethyl)phenyl]oxy}benzaldehyde (4.07 g, 13.54 mmol) in THF (10 mL) was added. The reaction mixture was warmed to rt and stirred for 1 h. The mixture was quenched with saturated $NH_4Cl$, and then concentrated. The residue was dissolved in ethyl acetate (100 mL) and washed with water, and brine. The mixture was dried over anhydrous sodium sulfate and concentrated. Purification via ISCO afforded the title compound (3.0 g).

LC-MS (ESI): m/z 299 $[M-H]+$; 5.07 min (ret time).

D65

2-(4-{[4-chloro-3-(trifluoromethyl)phenyl]oxy}phenyl)ethanol

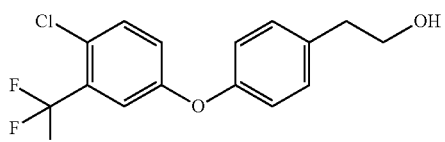

To a mixture of 1-chloro-4-[(4-ethenylphenyl)oxy]-2-(trifluoromethyl)benzene (3.8 g, 12.72 mmol) in anhydrous tetrahydrofuran (50 mL) was added 9-BBN (50.9 mL, 25.4 mmol) dropwise at 0° C. The reaction mixture was stirred at rt overnight, then sodium hydroxide (42.4 mL, 127 mmol) and H₂O₂ (2.60 mL, 25.4 mmol) were added at 0° C. The reaction mixture was stirred for 2 h at 50° C., and quenched with aq. Na₂SO₃ and then concentrated. Purification via mass-directed auto-preparation afforded the title compound (2.0 g).

LC-MS (ESI): m/z 317 [M+H]⁺; 3.56 min (ret time).

D66

5-Formyl-2-((6-methylpyridin-3-yl)oxy)benzonitrile

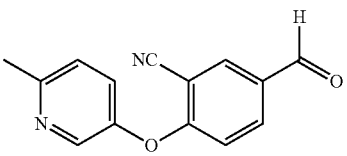 [SMILES: Cc1ccc(Oc2ccc(C=O)cc2C#N)cn1]

The title compound was prepared by a procedure similar to that described for D4 starting from 6-methyl-3-pyridinol and 2-fluoro-5-formylbenzonitrile.

LC-MS (ESI): m/z 239[M+H]⁺, 1.74 min (ret time).

D67

5-(Hydroxymethyl)-2-((6-methylpyridin-3-yl)oxy)benzonitrile

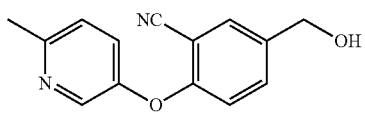 [SMILES: Cc1ccc(Oc2ccc(CO)cc2C#N)cn1]

The title compound was prepared by a procedure similar to that described for D5 starting from 5-Formyl-2-((6-methylpyridin-3-yl)oxy)benzonitrile.

LC-MS (ESI): m/z 241[M+H]⁺, 1.45 min (ret time).

D68

4-((6-(trifluoromethyl)pyridine-2-yl)oxy)benzaldehyde

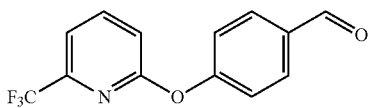

The title compound was prepared by a procedure similar to that described for D4 starting from 2-chloro-6-(trifluoromethyl)pyridine and 4-hydroxybenzaldehyde.

LC-MS (ESI): m/z 268 [M+H]⁺; 3.26 min (ret time)

D69

2-(trifluoromethyl)-6-(4-vinylphenoxy)pyridine

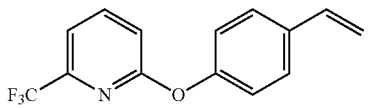

The title compound was prepared by a procedure similar to that described for D64 starting from 4-((6-(trifluoromethyl)pyridine-2-yl)oxy)benzaldehyde.

.LC-MS (ESI): m/z 266 [M+H]⁺; 3.79 min (ret time)

D70

2-(4-((6-(trifluoromethyl)pyridin-2-yl)oxy)phenyl)ethanol

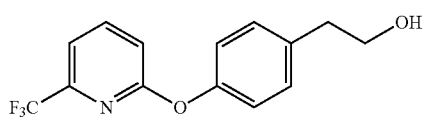 [SMILES: OCCc1ccc(Oc2cccc(C(F)(F)F)n2)cc1]

The title compound was prepared by a procedure similar to that described for D65 starting from 2-(trifluoromethyl)-6-(4-vinylphenoxy)pyridine.

D71

4-(3,5-difluorophenoxy)-3-fluorobenzaldehyde

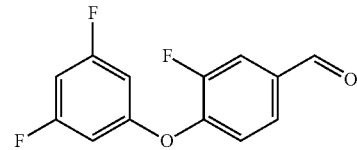 [SMILES: O=Cc1ccc(Oc2cc(F)cc(F)c2)c(F)c1]

The title compound was prepared by a procedure similar to that described for D4 starting from 3,4-difluorobenzaldehyde and 3,5-trifluorophenol.

LC-MS (ESI): m/z 253 [M+H]⁺; 2.66 min (ret time)

D72

(4-(3,5-difluorophenoxy)-3-fluorophenyl)methanol

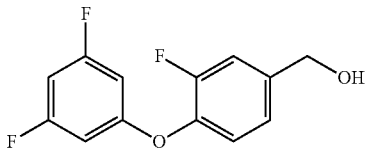 [SMILES: OCc1ccc(Oc2cc(F)cc(F)c2)c(F)c1]

The title compound was prepared by a procedure similar to that described for D5 starting from 4-(3,5-difluorophenoxy)-3-fluorobenzaldehyde.

LC-MS (ESI): m/z 237 [M+H]$^+$; 3.13 min (ret time)

D73

1-chloro-4-(4-ethynylphenoxy)-2-(trifluoromethyl) benzene

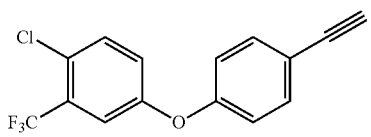 [SMILES: C#Cc1ccc(Oc2ccc(Cl)c(C(F)(F)F)c2)cc1]

To a solution of (4-chloro-3-(trifluoromethyl)phenoxy)benzaldehyde (1.82 g, 6.0 mmol) and dimethyl(1-diazo-2-oxopropyl)phosphonate (2.3 g, 12.1 mmol) in methanol (30 mL), was added potassium carbonate (4.18 g, 30.3 mmol), and stirred for 1 h at rt. The reaction mixture was concentrated and the residue was purified by FC (PE/EtOAc 20:1) to afford the title compound as a colorless oil.

LC-MS (ESI): m/z 297 [M+H]$^+$; 4.14 min (ret time).

D74

8-((4-(4-chloro-3-(trifluoromethyl)phenoxy)phenyl) ethynyl)-1-methyl-3,4-dihydro-1H-pyrimido[1,6-a] pyrimidin-6(2H)-one

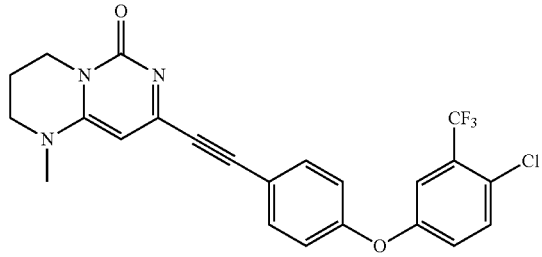 [SMILES: CN1CCCn2c1cc(C#Cc1ccc(Oc3ccc(Cl)c(C(F)(F)F)c3)cc1)nc2=O]

A suspension of bis(triphenylphosphine)palladium(II) chloride (70.3 mg, 0.1 mmol) and copper(I) iodide (19.1 mg, 0.1 mmol) in anhydrous THF (12 mL), was purged with Ar for 10 mins at rt. The suspension was treated with triethylamine (0.42 mL, 3.0 mmol), and 1-chloro-4-(4-ethynylphenoxy)-2-(trifluoromethyl)benzene (446 mg, 1.5 mmol) was added under an Ar atmosphere, which produced a dark amber color. After 5 mins, 8-chloro-1-methyl-3,4-dihydro-1H-pyrimido [1,6-a]pyrimidin-6(2H)-one (100 mg, 0.5 mmol) was added, and stirred for 2 h at 50° C. The reaction mixture was diluted with EtOAc, washed with water, and then concentrated. The residue was purified by MDAP to afford the title compound (30 mg) as a pale yellow solid.

LC-MS (ESI): m/z 460 [M+H]$^+$; 3.1 min (ret time).

D75

3-fluoro-4-(4-fluorophenoxy)benzaldehyde

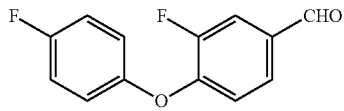 [SMILES: O=Cc1ccc(Oc2ccc(F)cc2)c(F)c1]

The title compound was prepared by a procedure similar to that described for D4 starting from 3,4-difluorobenzaldehyde and 4-fluorophenol.

LC-MS (ESI): m/z 235 [M+H]$^+$; 3.33 min (ret time)

D76

(3-fluoro-4-(4-fluorophenoxy)phenyl)methanol

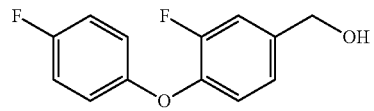 [SMILES: OCc1ccc(Oc2ccc(F)cc2)c(F)c1]

The title compound was prepared by a procedure similar to that described for D5 starting from 3-fluoro-4-(4-fluorophenoxy)benzaldehyde.

LC-MS (ESI): m/z 219 [M−17]$^+$; 2.95 min (ret time).

D77

5-(hydroxymethyl)-2-(3-pyridinyloxy)benzonitrile

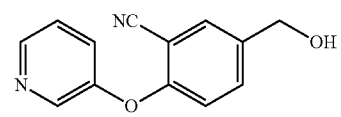 [SMILES: N#Cc1cc(CO)ccc1Oc1cccnc1]

The title compound was prepared by a procedure similar to that described for D5 starting from 5-formyl-2-(pyridine-3-yloxy)benzonitrile, which was prepared by reaction of pyridine-3-ol and 2-fluoro-5-formylbenzonitrile by the similar procedure to that described for D4.

LC-MS (ESI): m/z 227 [M+H]$^+$; 0.31 min (ret time)

D78

4-((3-(trifluoromethyl)oxy)phenyl)methanol

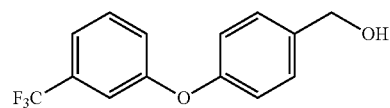 [SMILES: OCc1ccc(Oc2cccc(C(F)(F)F)c2)cc1]

The title compound was prepared by a procedure similar to that described for D5 starting from 4-(3-(trifluoromethyl) phenoxy)benzaldehyde, which was prepared by a reaction of 4-fluorobenzaldehyde and 3-(trifluoromethyl)phenol by a similar procedure to that described for D4.

LC-MS (ESI): m/z 251 [M−17]$^+$; 3.24 min (ret time)

D79

3,5-difluoro-4-(3-fluorophenoxy)benzaldehyde

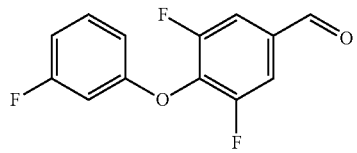 [SMILES: O=Cc1cc(F)c(Oc2cccc(F)c2)c(F)c1]

The title compound was prepared by a procedure similar to that described for D4 starting from 3,4,5-trifluorobenzaldehyde and 3-fluorophenol.

LC-MS (ESI): m/z 253 [M+H]$^+$; 3.44 min (ret time)

D80

(3,5-difluoro-4-(3-fluorophenoxy)phenyl)methanol

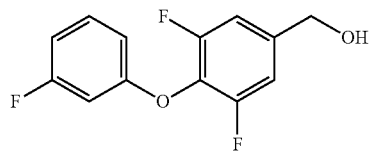 [SMILES: OCc1cc(F)c(Oc2cccc(F)c2)c(F)c1]

The title compound was prepared by a procedure similar to that described for D5 starting from 3,5-difluoro-4-(3-fluorophenoxy)benzaldehyde.

LC-MS (ESI): m/z 255 [M+H]$^+$; 3.02 min (ret time)

D81

4-(3,5-difluorophenoxy)-3,5-difluorobenzaldehyde

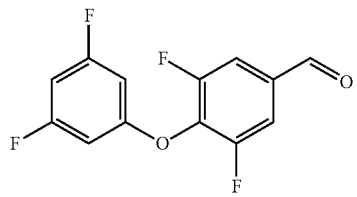 [SMILES: O=Cc1cc(F)c(Oc2cc(F)cc(F)c2)c(F)c1]

The title compound was prepared by a procedure similar to that described for D4 starting from 3,4,5-trifluorobenzaldehyde and 3,5-difluorophenol.

LC-MS (ESI): m/z 271 [M+H]$^+$; 3.54 min (ret time).

D82

(4-(3,5-difluorophenoxy)-3,5-difluorophenyl)methanol

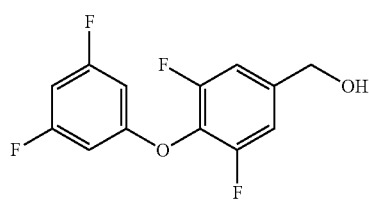 [SMILES: OCc1cc(F)c(Oc2cc(F)cc(F)c2)c(F)c1]

The title compound was prepared by a procedure similar to that described for D5 starting from 4-(3,5-difluorophenoxy)-3,5-difluorobenzaldehyde.

LC-MS (ESI): m/z 273 [M+H]$^+$; 3.28 min (ret time).

D83

2-(3-fluorophenoxy)-5-formylbenzonitrile

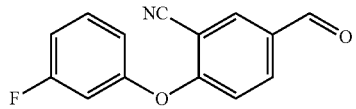 [SMILES: N#Cc1cc(C=O)ccc1Oc1cccc(F)c1]

The title compound was prepared by a procedure similar to that described for D4 starting from 2-fluoro-5-formylbenzonitrile and 2-fluorophenol.

LC-MS (ESI): m/z 242 [M+H]$^+$; 3.11 min (ret time).

D84

2-(3-fluorophenoxy)-5-(hydroxylmethyl)benzonitrile

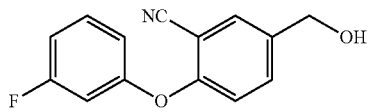 [SMILES: N#Cc1cc(CO)ccc1Oc1cccc(F)c1]

The title compound was prepared by a procedure similar to that described for D5 starting from 2-(3-fluorophenoxy)-5-formylbenzonitrile.

LC-MS (ESI): m/z 244 [M+H]$^+$; 2.79 min (ret time).

D85

3,5-difluoro-4-(3-(trifluoromethyl)phenoxy)benzaldehyde

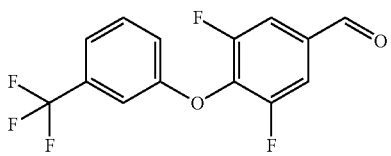 [SMILES: O=Cc1cc(F)c(Oc2cccc(C(F)(F)F)c2)c(F)c1]

The title compound was prepared by a procedure similar to that described for D4 starting from 3,4,5-trifluorobenzaldehyde and 3-(trifluoromethyl)phenol.

LC-MS (ESI): m/z 305 [M+H]$^+$; 3.36 min (ret time).

D86

(3,5-difluoro-4-(3-(trifluoromethyl)phenoxy)phenyl)methanol

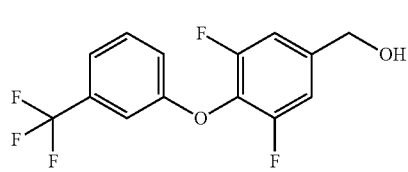

The title compound was prepared by a procedure similar to that described for D5 starting from 3,5-difluoro-4-(3-(trifluoromethyl)phenoxy)benzaldehyde.
LC-MS (ESI): m/z 305 [M+H]$^+$; 3.36 min (ret time).

D87

4-(4-chloro-3-fluorophenoxy)-3,5-difluorobenzaldehyde

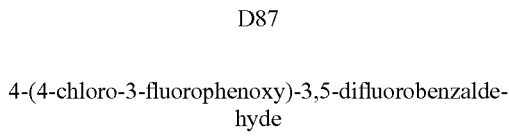

The title compound was prepared by a procedure similar to that described for D4 starting from 3,4,5-trifluorobenzaldehyde and 4-chloro-3-fluorophenol.
LC-MS (ESI): m/z 287 [M+H]$^+$; 3.64 min (ret time)

D88

(4-(4-chloro-3-fluorophenoxy)-3,5-difluorophenyl)methanol

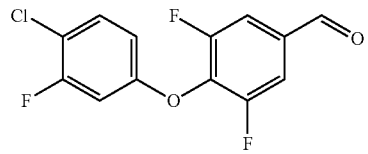 [SMILES: O=Cc1cc(F)c(Oc2ccc(F)c(Cl)c2)c(F)c1]

The title compound was prepared by a procedure similar to that described for D5 starting from 4-(4-chloro-3-fluorophenoxy)-3,5-difluorobenzaldehyde.
LC-MS (ESI): m/z 289 [M+H]$^+$; 3.35 min (ret time)

D89

4-(3-chloro-4-fluorophenoxy)-3,5-difluorobenzaldehyde

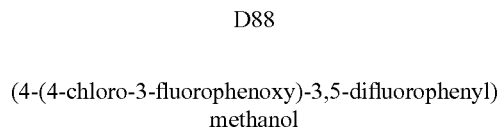

The title compound was prepared by a procedure similar to that described for D4 starting from 3,4,5-trifluorobenzaldehyde and 3-chloro-4-fluorophenol.
LC-MS (ESI): m/z 287 [M+H]$^+$; 3.62 min (ret time).

D90

(4-(3-chloro-4-fluorophenoxy)-3,5-difluorophenyl)methanol

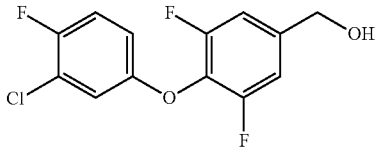 [SMILES: OCc1cc(F)c(Oc2ccc(F)c(Cl)c2)c(F)c1]

The title compound was prepared by a procedure similar to that described for D5 starting from 4-(3-chloro-4-fluorophenoxy)-3,5-difluorobenzaldehyde.
LC-MS (ESI): m/z 289 [M+H]$^+$; 3.29 min (ret time).

D91

2-(3-chloro-4-fluorophenoxy)-5-formylbenzonitrile

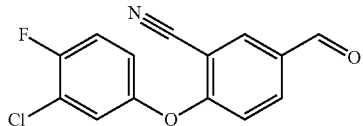

The title compound was prepared by a procedure similar to that described for D4 starting from 2-fluoro-5-formylbenzonitrile and 3-chloro-4-fluorophenol.
LC-MS (ESI): m/z 276 [M+H]$^+$; 3.31 min (ret time)

D92

2-(3-chloro-4-fluorophenoxy)-5-(hydroxymethyl)benzonitrile

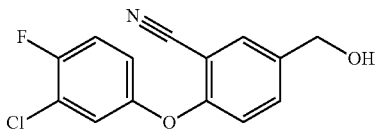

The title compound was prepared by a procedure similar to that described for D5 starting from 2-(3-chloro-4-fluorophenoxy)-5-formylbenzonitrile.
LC-MS (ESI): m/z 278 [M+H]$^+$; 3.02 min (ret time)

D93

3-(2-fluoro-4-formylphenoxy)benzonitrile

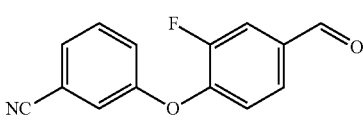 [SMILES: N#Cc1cccc(Oc2ccc(C=O)cc2F)c1]

The title compound was prepared by a procedure similar to that described for D4 starting from 3,4-difluorobenzaldehyde and 3-hydroxybenzonitrile.
LC-MS (ESI): m/z 242 [M+H]$^+$; 3.07 min (ret time)

D94

3-(2-fluoro-4-(hydroxymethyl)phenoxy)benzonitrile

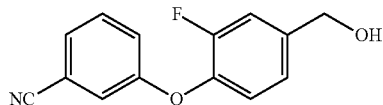 [SMILES: N#Cc1cccc(Oc2ccc(CO)cc2F)c1]

The title compound was prepared by a procedure similar to that described for D5 starting from 3-(2-fluoro-4-formylphenoxy)benzonitrile LC-MS (ESI): m/z 226 [M−17]$^+$; 2.74 min (ret time)

D95

5-formyl-2-(pyrimidin-5-yloxy)benzonitrile

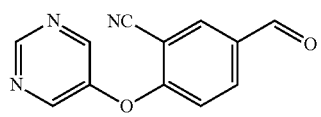 [SMILES: N#Cc1cc(C=O)ccc1Oc1cncnc1]

The title compound was prepared by a procedure similar to that described for D4 starting from 2-fluoro-5-formylbenzonitrile and pyrimidin-5-ol.

LC-MS (ESI): m/z 226 [M+H]$^+$; 1.87 min (ret time)

D96

5-(hydroxymethyl)-2-(pyrimidin-5-yloxy)benzonitrile

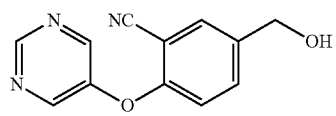 [SMILES: N#Cc1cc(CO)ccc1Oc1cncnc1]

The title compound was prepared by a procedure similar to that described for D5 starting from 5-formyl-2-(pyrimidin-5-yloxy)benzonitrile.

LC-MS (ESI): m/z 228 [M−17]$^+$; 1.38 min (ret time)

D97

3,5-difluoro-4-(3-fluorophenoxy)benzaldehyde

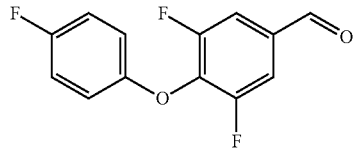 [SMILES: O=Cc1cc(F)c(Oc2ccc(F)cc2)c(F)c1]

The title compound was prepared by a procedure similar to that described for D4 starting from 3,4,5-trifluorobenzaldehyde and 3-fluorophenol.

LC-MS (ESI): m/z 253 [M+H]$^+$; 3.44 min (ret time)

D98

(3,5-difluoro-4-(3-fluorophenoxyl)phenyl)methanol

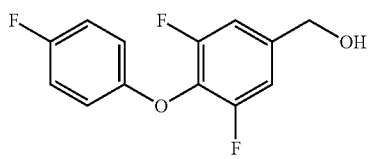 [SMILES: OCc1cc(F)c(Oc2ccc(F)cc2)c(F)c1]

The title compound was prepared by a procedure similar to that described for D5 starting from 3,5-difluoro-4-(3-fluorophenoxyl)benzaldehyde.

LC-MS (ESI): m/z 255 [M+H]$^+$; 3.02 min (ret time)

D99

3,5-difluoro-4-(3-fluoro-4-(trifluoromethyl)phenoxy)benzaldehyde

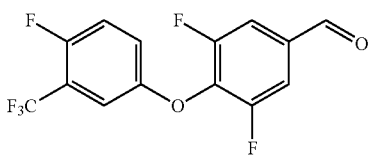 [SMILES: O=Cc1cc(F)c(Oc2ccc(F)c(C(F)(F)F)c2)c(F)c1]

The title compound was prepared by a procedure similar to that described for D4 starting from 3,4,5-trifluorobenzaldehyde and 3-fluoro-4-(trifluoromethyl)phenol.

LC-MS (ESI): m/z 321 [M+H]$^+$; 3.70 min (ret time)

D100

(3,5-difluoro-4-(3-fluoro-4-(trifluoromethyl)phenoxy)phenyl)methanol

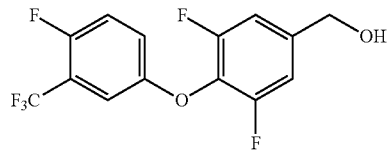 [SMILES: OCc1cc(F)c(Oc2ccc(F)c(C(F)(F)F)c2)c(F)c1]

The title compound was prepared by a procedure similar to that described for D5 starting from 3,5-difluoro-4-(3-fluoro-4-(trifluoromethyl)phenoxy)benzaldehyde.

LC-MS (ESI): m/z 323 [M+H]$^+$; 3.46 min (ret time)

D101

3,5-difluoro-4-(3-(trifluoromethyl)phenoxy)benzaldehyde

The title compound was prepared by a procedure similar to that described for D4 starting from 3,4,5-trifluorobenzaldehyde and 3-(trifluoromethyl)phenol.
LC-MS (ESI): m/z 305 [M+H]$^+$; 3.36 min (ret time).

D102

(3,5-difluoro-4-(3-(trifluoromethyl)phenoxy)phenyl)methanol

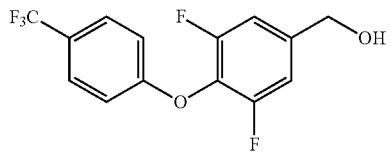 [SMILES: OCc1cc(F)c(Oc2ccc(C(F)(F)F)cc2)c(F)c1]

The title compound was prepared by a procedure similar to that described for D5 starting from 3,5-difluoro-4-(3-(trifluoromethyl)phenoxy)benzaldehyde.
LC-MS (ESI): m/z 305 [M+H]$^+$; 3.36 min (ret time).

D103

4-(3-chlorophenoxy)-3,5-difluorobenzaldehyde

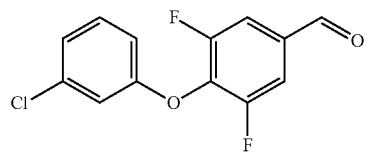 [SMILES: O=Cc1cc(F)c(Oc2cccc(Cl)c2)c(F)c1]

The title compound was prepared by a procedure similar to that described for D4 starting from 3,4,5-trifluorobenzaldehyde and 3-chlorophenol.
LC-MS (ESI): m/z 269 [M+H]$^+$; 3.63 min (ret time).

D104

(4-(3-chlorophenoxy)-3,5-difluorophenyl)methanol

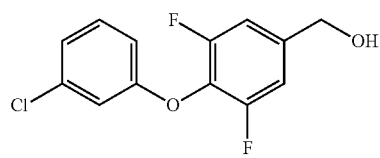 [SMILES: OCc1cc(F)c(Oc2cccc(Cl)c2)c(F)c1]

The title compound was prepared by a procedure similar to that described for D5 starting from 4-(3-chlorophenoxy)-3,5-difluorobenzaldehyde.
LC-MS (ESI): m/z 271 [M+H]$^+$; 3.28 min (ret time).

D105

4-(3,4-difluorophenoxy)-3,5-difluorobenzaldehyde

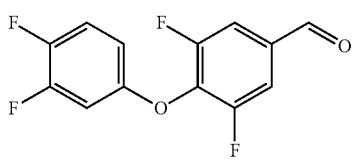 [SMILES: O=Cc1cc(F)c(Oc2ccc(F)c(F)c2)c(F)c1]

The title compound was prepared by a procedure similar to that described for D4 starting from 3,4,5-trifluorobenzaldehyde and 3,4-difluorophenol.
LC-MS (ESI): m/z 271 [M+H]$^+$; 3.47 min (ret time).

D106

(4-(3,4-difluorophenoxy)-3,5-difluorophenyl)methanol

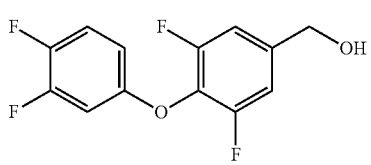 [SMILES: OCc1cc(F)c(Oc2ccc(F)c(F)c2)c(F)c1]

The title compound was prepared by a procedure similar to that described for D5 starting from (4-(3,4-difluorophenoxy)-3,5-difluorophenyl)methanol.
LC-MS (ESI): m/z 273 [M+H]$^+$; 3.15 min (ret time).

D107

4-((2-chloropyridin-4-yl)oxy)-3-fluorobenzaldehyde

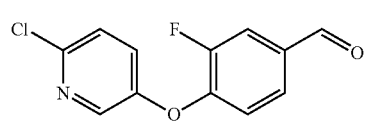 [SMILES: O=Cc1ccc(Oc2ccc(Cl)nc2)c(F)c1]

The title compound was prepared by a procedure similar to that described for D4 starting from 3,4-difluorobenzaldehyde and 2-chloropyridin-4-ol.
LC-MS (ESI): m/z 269 [M+H]$^+$; 3.02 min (ret time)

D108

(4-((2-chloropyridin-4-yl)oxy)-3-fluorophenyl)methanol

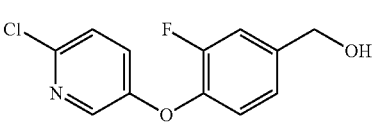 [SMILES: OCc1ccc(Oc2ccc(Cl)nc2)c(F)c1]

The title compound was prepared by a procedure similar to that described for D5 starting from 44-((2-chloropyridin-4-yl)oxy)-3-fluorobenzaldehyde LC-MS (ESI): m/z 271 [M+H]$^+$; 2.67 min (ret time)

D109

2-(4-chloro-3-fluorophenoxy)-5-formylbenzonitrile

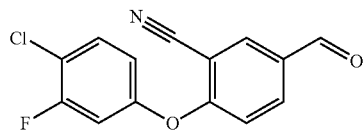 [SMILES: N#Cc1cc(C=O)ccc1Oc1ccc(Cl)c(F)c1]

The title compound was prepared by a procedure similar to that described for D4 starting from 2-fluoro-5-formylbenzonitrile and 4-chloro-3-fluorophenol.
LC-MS (ESI): m/z 276 [M+H]$^+$; 3.33 min (ret time)

D110

2-(4-chloro-3-fluorophenoxy)-5-(hydroxymethyl)benzonitrile

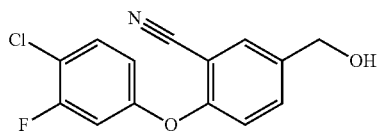 [SMILES: N#Cc1cc(CO)ccc1Oc1ccc(Cl)c(F)c1]

The title compound was prepared by a procedure similar to that described for D5 starting from 2-(3-chloro-4-fluorophenoxy)-5-formylbenzonitrile.
LC-MS (ESI): m/z 278 [M+H]$^+$; 3.02 min (ret time)

D111

4-(4-Chloro-3-trifluoromethyl-phenoxy)-3-fluoro-benzaldehyde

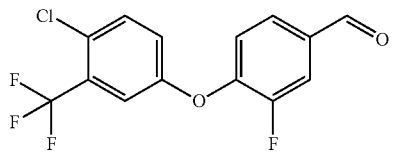 [SMILES: O=Cc1ccc(Oc2ccc(Cl)c(C(F)(F)F)c2)c(F)c1]

The title compound was prepared by a procedure similar to that described for D4 starting from 3,4-difluorobenzaldehyde and 4-chloro-3-trifluoromethyl-phenol.
LC-MS (ESI): m/z 319 [M+H]$^+$; 1.22 min (ret time)

D112

[4-(4-Chloro-3-trifluoromethyl-phenoxy)-3-fluoro-phenyl]-methanol

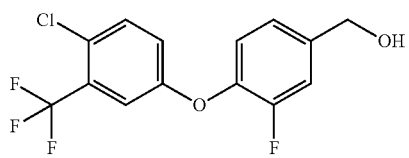 [SMILES: OCc1ccc(Oc2ccc(Cl)c(C(F)(F)F)c2)c(F)c1]

The title compound was prepared by a procedure similar to that described for D5 starting from 4-(4-chloro-3-trifluoromethyl-phenoxy)-3-fluoro-benzaldehyde.
LC-MS (ESI): m/z 303 [M+H]$^+$; 1.17 min (ret time)

D113

3-Fluoro-5-(2-fluoro-4-formyl-phenoxy)-benzonitrile

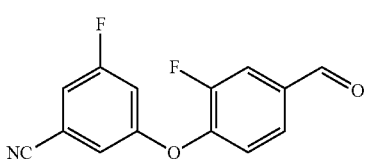 [SMILES: N#Cc1cc(F)cc(Oc2ccc(C=O)cc2F)c1]

The title compound was prepared by a procedure similar to that described for D4 starting from 3,4-difluorobenzaldehyde and 3-fluoro-5-hydroxybenzonitrile.
LC-MS (ESI): m/z 260 [M+H]$^+$; 1.07 min (ret time)

D114

3-fluoro-5-(2-fluoro-4-(hydroxymethyl)phenoxy)benzonitrile

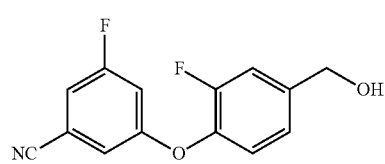 [SMILES: N#Cc1cc(F)cc(Oc2ccc(CO)cc2F)c1]

The title compound was prepared by a procedure similar to that described for D5 starting from 3-Fluoro-5-(2-fluoro-4-formyl-phenoxy)-benzonitrile.
LC-MS (ESI): m/z 244 [M+H]$^+$; 0.98 min (ret time)

D115

4-(4-fluoro-3-(trifluoromethyl)phenoxy)benzaldehyde

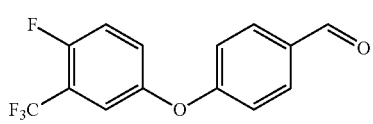 [SMILES: O=Cc1ccc(Oc2ccc(F)c(C(F)(F)F)c2)cc1]

The title compound was prepared by a procedure similar to that described for D4 starting from 4-fluorobenzaldehyde and 4-fluoro-3-(trifluoromethyl)phenol.
LC-MS (ESI): m/z 285 [M+H]$^+$; 3.61 min (ret time)

D116

(4-(4-fluoro-3-(trifluoromethyl)phenoxy)phenyl)methanol

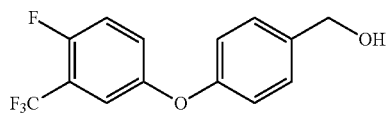 [SMILES: OCc1ccc(Oc2ccc(F)c(C(F)(F)F)c2)cc1]

The title compound was prepared by a procedure similar to that described for D5 starting from 4-(4-fluoro-3-(trifluoromethyl)phenoxy)benzaldehyde.
LC-MS (ESI): m/z 287 [M+H]$^+$; 3.28 min (ret time)

D117

3-fluoro-4-(3-(trifluoromethyl)phenoxy)benzaldehyde

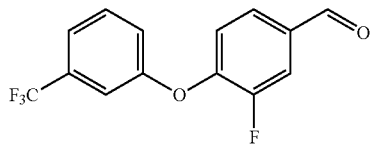

The title compound was prepared by a procedure similar to that described for D4 starting from 3,4-difluorobenzaldehyde and 3-(trifluoromethyl)phenol.

LC-MS (ESI): m/z 285 [M+H]$^+$; 3.47 min (ret time).

D118

(3-fluoro-4-(3-(trifluoromethyl)phenoxy)phenyl)methanol

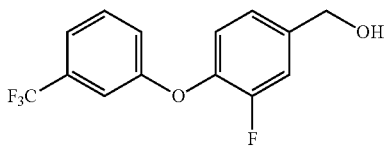

The title compound was prepared by a procedure similar to that described for D5 starting from 3-fluoro-4-(3-(trifluoromethyl)phenoxy)benzaldehyde.

LC-MS (ESI): m/z 287 [M+H]$^+$; 3.22 min (ret time).

D119

Preparation of 2-Fluoro-4-(2-hydroxy-ethyl)-phenol

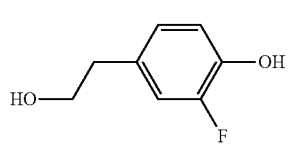 [SMILES: OCCc1ccc(O)c(F)c1]

To a solution of 2-(3-fluoro-4-hydroxyphenyl)acetic acid (9.8 g, 57.6 mmol) in THF (500 mL) was added dropwise 57.6 mL of borane (10M in Me$_2$S) at room temperature. The reaction mixture was stirred at room temperature for 12 hours. The reaction mixture was added to CH$_3$OH and was concentrated under reduced pressure. The residue was partitioned between EtOAc (800 mL) and water (100 mL). The organic layer was dried and concentrated to dryness to give the title product (8.5 g, 76%).

$^1$HNMR (DMSO, 400 MHz): δ ppm 2.59 (t, J=7.2 Hz, 2H), 3.53 (t, J=7.2 Hz, 2H), 4.60 (bs, 1H), 6.80-6.86 (m, 2H), 6.96-6.99 (m, 2H), 9.54 (s, 1H).

D120

2-[4-(4-Chloro-3-fluoro-phenoxy)-3-fluoro-phenyl]-ethanol

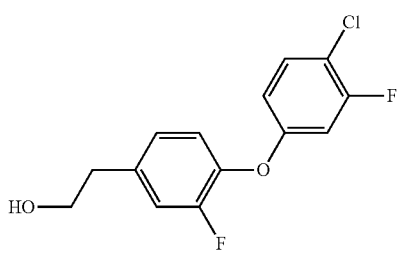 [SMILES: OCCc1ccc(Oc2ccc(Cl)c(F)c2)c(F)c1]

To a solution of 2-fluoro-4-(2-hydroxyethyl)phenol (22.41 mmol, 3.5 g) and (4-chloro-3-fluorophenyl)boronic acid (45 mmol, 7.82 g) in dry CH$_2$Cl$_2$ (150 mL) were added copper (II) acetate (4.5 mmol 0.81 g), pyridine (45 mmol, 3.55 g), and 4 Å molecular sieves in turn. The mixture was stirred at room temperature under N$_2$ for 72 hours. The reaction mixture was filtered and the filtrate was concentrated to give crude product. The crude product was purified by silica gel chromatography to provide the desired product (1.4 g, 20%).

LC-MS (ESI): m/z 285 [M+H]$^+$; 1.09 min (ret time)

D121

2-[4-(3-Chloro-4-fluoro-phenoxy)-phenyl]-ethanol

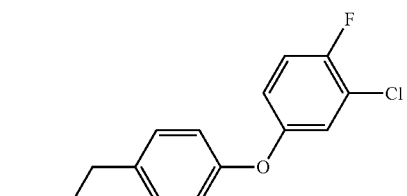

The title compound was prepared by a procedure similar to that described for D120 starting from 4-(2-hydroxyethyl)phenol and (3-chloro-4-fluorophenyl)boronic acid.

LC-MS (ESI): m/z 249 [M+H]$^+$; 1.08 min (ret time)

D122

4-(2-cyano-4-formylphenoxy)-2-fluorobenzonitrile

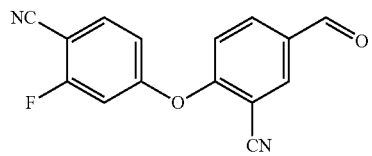 [SMILES: N#Cc1ccc(Oc2ccc(C=O)cc2C#N)cc1F]

The title compound was prepared by a procedure similar to that described for D4 starting from 2-fluoro-5-formylbenzonitrile and 2-fluoro-4-hydroxybenzonitrile.

LC-MS (ESI): m/z 267 [M+H]$^+$; 2.97 min (ret time)

D123

4-(2-cyano-4-(hydroxymethyl)phenoxy)-2-fluorobenzonitrile

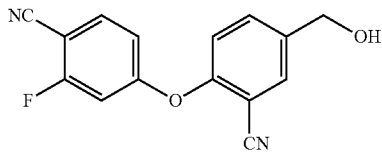 [SMILES: N#Cc1ccc(Oc2ccc(CO)cc2C#N)cc1F]

The title compound was prepared by a procedure similar to that described for D5 starting from 4-(2-cyano-4-formylphenoxy)-2-fluorobenzonitrile.

LC-MS (ESI): m/z 269 [M+H]$^+$; 2.65 min (ret time)

D124

2-[3-Fluoro-4-(3-trifluoromethyl-phenoxy)-phenyl]-ethanol

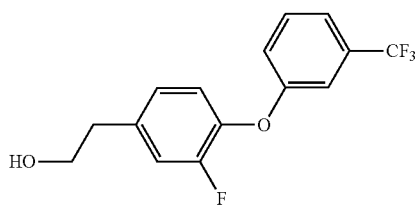 [SMILES: OCCc1ccc(Oc2cccc(C(F)(F)F)c2)c(F)c1]

The title compound was prepared by a procedure similar to that described for D120 starting from 2-fluoro-4-(2-hydroxyethyl)phenol and (3-(trifluoromethyl)phenyl)boronic acid.

LC-MS (ESI): m/z 301 [M+H]$^+$; 1.15 min (ret time)

D125

2-chloro-4-(2-cyano-4-formylphenoxy)benzonitrile

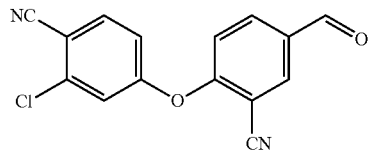 [SMILES: N#Cc1ccc(Oc2ccc(C=O)cc2C#N)cc1Cl]

The title compound was prepared by a procedure similar to that described for D4 starting from 2-fluoro-5-formylbenzonitrile and 2-chloro-4-hydroxybenzonitrile.

LC-MS (ESI): m/z 283 [M+H]$^+$; 3.07 min (ret time)

D126

2-chloro-4-(2-cyano-4-(hydroxymethyl)phenoxy)benzonitrile

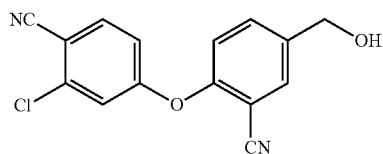 [SMILES: N#Cc1ccc(Oc2ccc(CO)cc2C#N)cc1Cl]

The title compound was prepared by a procedure similar to that described for D5 starting from 2-chloro-4-(2-cyano-4-formylphenoxy)benzonitrile.

LC-MS (ESI): m/z 285 [M+H]$^+$; 2.79 min (ret time)

D127

2-(4-chloro-3-(trifluoromethyl)phenoxy)-5-formylbenzonitrile

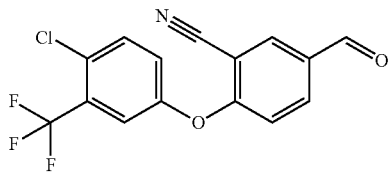 [SMILES: N#Cc1cc(C=O)ccc1Oc1ccc(Cl)c(C(F)(F)F)c1]

The title compound was prepared by a procedure similar to that described for D4 starting from 2-fluoro-5-formylbenzonitrile and 4-chloro-3-(trifluoromethyl)phenol.

LC-MS (ESI): m/z 326 [M+H]$^+$; 3.55 min (ret time)

D128

2-(4-chloro-3-(trifluoromethyl)phenoxy)-5-(hydroxymethyl)benzonitrile

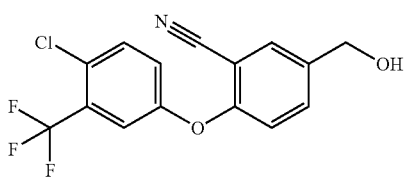 [SMILES: N#Cc1cc(CO)ccc1Oc1ccc(Cl)c(C(F)(F)F)c1]

The title compound was prepared by a procedure similar to that described for D5 starting from 2-(4-chloro-3-(trifluoromethyl)phenoxy)-5-formylbenzonitrile.

LC-MS (ESI): m/z 328 [M+H]$^+$; 3.27 min (ret time)

D129

4-(3-fluoro-4-methylphenoxy)benzaldehyde

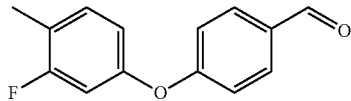

The title compound was prepared by a procedure similar to that described for D4 starting from 3-fluoro-4-methylphenol and 4-fluorobenzaldehyde LC-MS (ESI): m/z 231 [M+H]$^+$; 3.57 min (ret time)

D130

(4-(3-fluoro-4-methylphenoxy)phenyl)methanol

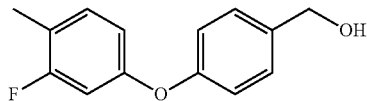 [SMILES: Cc1ccc(Oc2ccc(CO)cc2)cc1F]

The title compound was prepared by a procedure similar to that described for D5 starting from 4-(3-fluoro-4-methylphenoxy)benzaldehyde.

LC-MS (ESI): m/z 215 [M−17]$^+$; 3.16 min (ret time).

D131 ethyl 2-chloro-6-(3,4-difluorophenoxy)-5-fluoronicotinate

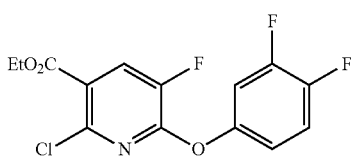 [SMILES: CCOC(=O)c1cc(F)c(Oc2ccc(F)c(F)c2)nc1Cl]

To a solution of ethyl 2,6-dichloro-5-fluoronicotinate (20 g, 84 mmol) and 3,4-difluorophenol (10.93 g, 84 mmol) in acetonitrile (200 mL) was added potassium carbonate (20.90 g, 151 mmol). The reaction mixture was stirred at 80° C. for 2 hr. and then concentrated under reduced pressure. The crude product was purified by silica gel chromatography eluting with Hex/EtOAc (10:1) to give ethyl 2-chloro-6-(3,4-difluorophenoxy)-5-fluoronicotinate (23.5 g, 80%).

LC-MS (ESI): m/z 332 [M+H]$^+$; 1.24 min (ret time)

D132 ethyl 6-(3,4-difluorophenoxy)-5-fluoronicotinate

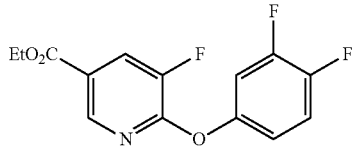 [SMILES: CCOC(=O)c1cnc(Oc2ccc(F)c(F)c2)c(F)c1]

To a solution of ammonium formate (28.5 g, 452 mmol) and ethyl 2-chloro-6-(3,4-difluorophenoxy)-5-fluoronicotinate (30 g, 90 mmol) in methanol (300 mL) was added Pd/C (3 g, 2.82 mmol). The reaction mixture was stirred at 65° C. for 10 hr. and then filtered. The filtrate was concentrated under reduced pressure to get ethyl 6-(3,4-difluoro phenoxy)-5-fluoronicotinate (20 g, 48.4%).

LC-MS (ESI): m/z 298 [M+H]$^+$; 1.22 min (ret time)

D133

(6-(3,4-difluorophenoxy)-5-fluoropyridin-3-yl)methanol

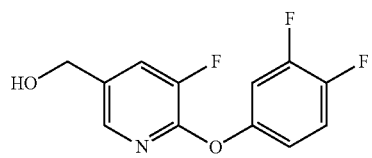

The title compound was prepared by a procedure similar to that described for D5 starting from ethyl 6-(3,4-difluorophenoxy)-5-fluoronicotinate.

LC-MS (ESI): m/z 256 [M+H]$^+$; 1.03 min (ret time)

D134

(6-(3,4-difluorophenoxy)-5-fluoropyridin-3-yl)methyl methanesulfonate

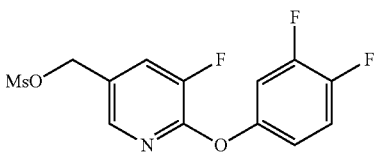 [SMILES: CS(=O)(=O)OCc1cnc(Oc2ccc(F)c(F)c2)c(F)c1]

To a solution of (6-(3,4-difluorophenoxy)-5-fluoropyridin-3-yl)methanol (8.4 g, 26.7 mmol) and triethylamine (6.89 mL, 49.4 mmol) in dichloromethane (DCM) (100 mL) was added methanesulfonyl chloride (4.8 g, 41.9 mmol). The reaction mixture was stirred at 20° C. for 2 hr. then 200 mL of H$_2$O was added. The organic layer was separated, dried over Na$_2$SO$_4$, and then concentrated under reduced pressure to give (6-(3,4-difluorophenoxy)-5-fluoro pyridin-3-yl)methyl methanesulfonate (8 g, 42.3%).

LC-MS (ESI): m/z 334 [M+H]$^+$; 1.13 min (ret time)

D135

2-(6-(3,4-difluorophenoxy)-5-fluoropyridin-3-yl)acetonitrile

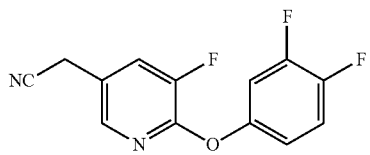 [SMILES: N#CCc1cnc(Oc2ccc(F)c(F)c2)c(F)c1]

To a solution of (6-(3,4-difluorophenoxy)-5-fluoropyridin-3-yl)methyl methanesulfonate (8 g, 11.28 mmol) and tetrabutylammonium fluoride (5.90 g, 22.56 mmol) in acetonitrile (100 mL) was added trimethylsilyl cyanide (3.02 mL, 22.56 mmol). The reaction mixture was stirred at 80° C. for 2 hr., and then concentrated under reduced pressure. The crude product was purified bysilica gel chromatography eluting with Hex/EtOAc (5:1) to give get 2-(6-(3,4-difluorophenoxy)-5-fluoropyridin-3-yl)acetonitrile (3 g, 89%).

LC-MS (ESI): m/z 265 [M+H]$^+$; 1.09 min (ret time)

D136 ethyl 2-(6-(3,4-difluorophenoxy)-5-fluoropyridin-3-yl)acetate

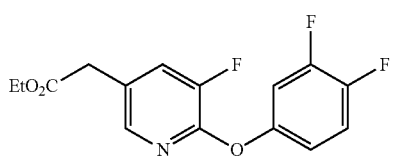 [SMILES: CCOC(=O)Cc1cnc(Oc2ccc(F)c(F)c2)c(F)c1]

To 2-(6-(3,4-difluorophenoxy)-5-fluoropyridin-3-yl)acetonitrile (3 g, 9.99 mmol) and EtOH (30 ml, 514 mmol) was added 18 M sulfuric acid (10 ml, 180 mmol). The reaction mixture was stirred at 80° C. for 2 hr., and then was concentrated under reduced pressure. To the residue was added 50 mL of concentrated ammonia solution and 100 mL of CH$_2$Cl$_2$. The organic layer was separated and dried over Na$_2$SO$_4$, and then concentrated under reduced pressure to give ethyl 2-(6-(3,4-difluorophenoxy)-5-fluoropyridin-3-yl)acetate (3.1 g, 67.8%).

LC-MS (ESI): m/z 312 [M+H]$^+$; 1.17 min (ret time)

D137

2-(6-(3,4-difluorophenoxy)-5-fluoropyridin-3-yl)ethanol

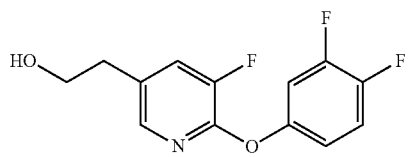 [SMILES: OCCc1cnc(Oc2ccc(F)c(F)c2)c(F)c1]

The title compound was prepared by a procedure similar to that described for D5 starting from ethyl 2-(6-(3,4-difluorophenoxy)-5-fluoropyridin-3-yl)acetate.

LC-MS (ESI): m/z 270 [M+H]$^+$; 1.02 min (ret time)

D138

4-(3,4-difluorophenoxy)benzaldehyde

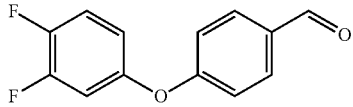 [SMILES: O=Cc1ccc(Oc2ccc(F)c(F)c2)cc1]

The title compound was prepared by a procedure similar to that described for D4 starting from 3,4-difluorophenol and 4-fluorobenzaldehyde.

LC-MS (ESI): m/z 235 [M+H]$^+$; 3.36 min (ret time)

D139

1,2-difluoro-4-(4-vinylphenoxy)benzene

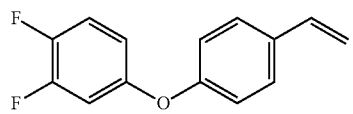 [SMILES: C=Cc1ccc(Oc2ccc(F)c(F)c2)cc1]

The title compound was prepared by a procedure similar to that described for D64 starting from 4-(3,4-difluorophenoxy)benzaldehyde.

LC-MS (ESI): m/z 233 [M+H]$^+$; 3.99 min (ret time)

D140

2-(4-(3,4-difluorophenoxy)phenyl)ethanol

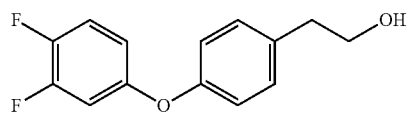 [SMILES: OCCc1ccc(Oc2ccc(F)c(F)c2)cc1]

The title compound was prepared by a procedure similar to that described for D65 starting from 1,2-difluoro-4-(4-vinylphenoxy)benzene.

LC-MS (ESI): m/z 234 [M−17]$^+$; 3.14 min (ret time).

D141

N-(3-bromopropyl)-2,6-dichloropyrimidin-4-amine

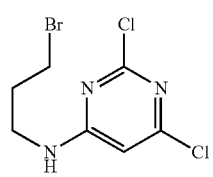 [SMILES: Clc1cc(NCCCBr)nc(Cl)n1]

A solution of 2,4,6-trichloropyrimidine (100 g, 545 mmol) in acetonitrile (2000 mL) was added triethylamine (166 g, 1636 mmol) at 0° C., The reaction mixture was stirred for 5 min at rt, then 3-bromopropan-1-amine hydrobromide (119 g, 545 mmol) was added portionwise. The reaction mixture was stirred for 1 h at rt, and filtered to provide a clear solution. Purification via FC afforded the title compound as a white solid (47 g, 30% yield).

LC-MS (ESI): m/z 286[M+H]$^+$, 1.13 min (ret time).

D142

8-chloro-3,4-dihydro-1H-pyrimido[1,6-a]pyrimidin-6(2H)-one

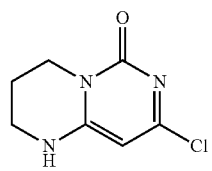 [SMILES: O=c1nc(Cl)cc2n1CCCN2]

A suspension of N-(3-bromopropyl)-2,6-dichloropyrimidin-4-amine (47 g, 165 mmol) and potassium carbonate (68.4 g, 495 mmol) in 1,4-dioxane (100 mL) and water (100 mL), was heated to 60° C. overnight. The mixture was evaporated to remove the dioxane solvent and the mixture was adjusted to pH ~6 with HCl (6M). The mixture was extracted with ethyl acetate to remove by product and aqueous phase was adjusted to pH ~7 with NaOH (2M), evaporated to afford the title compound (17 g, 55% yield).

D143 tert-butyl 8-chloro-6-oxo-2,3,4,6-tetrahydro-1H-pyrimido[1,6-a]pyrimidine-1-carboxylate

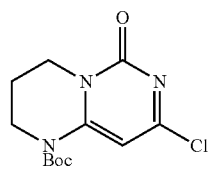 [SMILES: CC(C)(C)OC(=O)N1CCCn2c1cc(Cl)nc2=O]

To a solution of crude 8-chloro-3,4-dihydro-1H-pyrimido[1,6-a]pyrimidin-6(2H)-one (8.0 g, 43.1 mmol) in tetrahydrofuran (THF) (100 mL), were added (Boc)$_2$O (20.01 mL, 86 mmol), and DMAP (0.527 g, 4.31 mmol). The reaction mixture was stirred for 2 h at rt and partitioned between EA and water. The organic layer was washed with water, dried over (Na$_2$SO$_4$) and evaporated to afford the title compound (12 g, 97% yield).

LC-MS (ESI): m/z 286 [M+1]+; 0.98 (ret time).

EXAMPLES

E1

5-(((1-methyl-6-oxo-2,3,4,6-tetrahydro-1H-pyrimido[1,6-a]pyrimidin-8-yl)oxy)methyl)-2-(3-(trifluoromethyl)phenoxy)benzonitrile

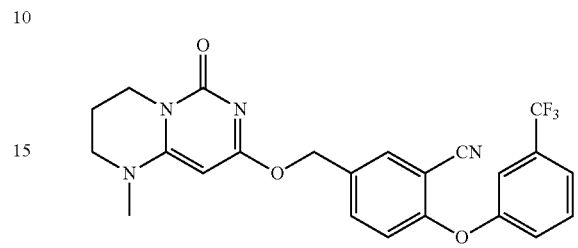

To a solution of 8-chloro-1-methyl-3,4-dihydro-1H-pyrimido[1,6-a]pyrimidin-6(2H)-one (31 mg, 0.153 mmol) and 5-(hydroxymethyl)-2-(3-(trifluoromethyl)phenoxy)benzonitrile (49.4 mg, 0.168 mmol) in N, N-dimethylformamide (DMF) (1.5 mL), was added NaH (18.36 mg, 0.459 mmol). The reaction mixture was stirred at rt for 30 min. Aqueous HCl solution was added to adjust pH to ~7. Purification by Mass Directed AutoPrep (MDAP) afforded the title compound as a white solid (35 mg, 50% yield).

LC-MS (ESI): m/z 457 [M+H]$^+$; 2.72 min (ret time).

E2

5-(((1-methyl-6-oxo-2,3,4,6-tetrahydro-1H-pyrimido[1,6-a]pyrimidin-8-yl)oxy)methyl)-2-((5-(trifluoromethyl)pyridin-2-yl)oxy)benzonitrile

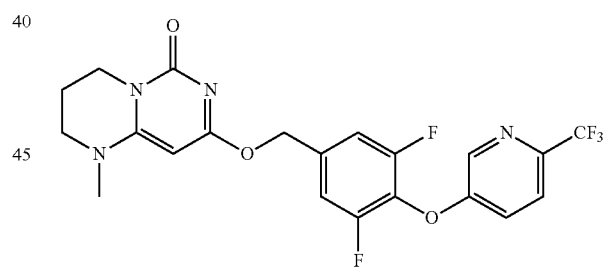

The title compound was prepared by a procedure similar to that described for E1 starting from 8-chloro-1-methyl-3,4-dihydro-1H-pyrimido[1,6-a]pyrimidin-6(2H)-one and 5-(hydroxymethyl)-2-5 ((5-(trifluoromethyl)pyridin-2-yl)oxy)benzonitrile. An exemplary process is shown as below: To a solution of 5-(hydroxymethyl)-2-((5-(trifluoromethyl)pyridin-2-yl)oxy)benzonitrile (0.108 mL, 0.601 mmol) in N,N-dimethylformamide (DMF) (5 mL) was added NaH (48.1 mg, 1.202 mmol) and stirred for 10 mins. Then 8-chloro-1-methyl-3,4-dihydro-1H-pyrimido[1,6-a]pyrimidin-6(2H)-one (80 mg, 0.401 mmol) was charged and stirred for 45 mins at rt. The resulting solution was 10 quenched by addition of 1 mL aq. NH$_4$Cl and the solution was filtered. The resulting solution was submitted for MDAP to afford the desired product as a white solid.

LC-MS (ESI): m/z 458 [M+H]$^+$; 2.55 min (ret time).

E3

8-((3,5-difluoro-4-((6-(trifluoromethyl)pyridin-3-yl)oxy)benzyl)oxy)-1-methyl-3,4-dihydro-1H-pyrimido[1,6-a]pyrimidin-6(2H)-one

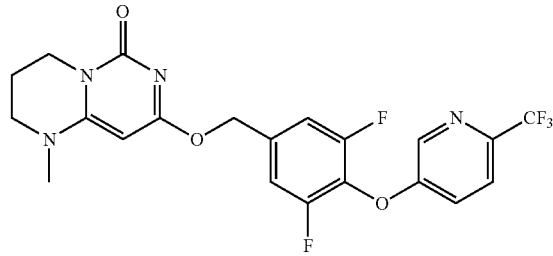 [SMILES: CN1CCCn2c1cc(OCc1cc(F)c(Oc3ccc(C(F)(F)F)nc3)c(F)c1)nc2=O]

The title compound was prepared by a procedure similar to that described for E1 starting from 8-chloro-1-methyl-3,4-dihydro-1H-pyrimido[1,6-a]pyrimidin-6(2H)-one and (3,5-difluoro-4-((6-(trifluoromethyl)pyridin-3-yl)oxy)phenyl)methanol. An exemplary process is shown below: To a solution of 8-chloro-1-methyl-3,4-dihydro-1H-pyrimido[1,6-c]pyrimidin-6(2H)-one, trifluoroacetic acid salt (43 mg, 0.137 mmol) and (3,5-difluoro-4-((6-(trifluoromethyl)pyridin-3-yl)oxy)phenyl)methanol (46.0 mg, 0.151 mmol) in N,N-dimethylformamide (DMF) (1.5 mL) were added NaH (16.45 mg, 0.411 mmol). The mixture was stirred at room temperature for 30 mins. Sufficient aqueous HCl solution (1 M) was added to adjust the solution to pH to ~7. The resulted mixture was purified by Mass Directed AutoPrep (basic mobile phase) to afford the title compound (18 mg, 0.038 mmol, 28.0% yield) as a white solid.

$^1$H NMR (400 MHz, CDCl$_3$) δ ppm 8.50 (d, J=2.7 Hz, 1H), 7.63 (d, J=8.7 Hz, 1H), 7.27-7.30 (m, 1H), 7.12 (d, J=8.2 Hz, 2H), 5.40 (s, 2H), 5.10 (s, 1H), 3.99 (t, J=5.9 Hz, 2H), 3.42 (t, J=6.0 Hz, 2H), 3.01 (s, 3H), 2.09 (m, J=6.0 Hz, 2H).

LC-MS (ESI): m/z 469 [M+H]$^+$; 2.65 min (ret time).

E4

8-((3-fluoro-4-((6-(trifluoromethyl)pyridin-3-yl)oxy)benzyl)oxy)-1-methyl-3,4-dihydro-1H-pyrimido[1,6-a]pyrimidin-6(2H)-one

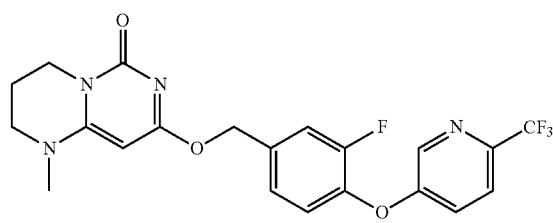 [SMILES: CN1CCCn2c1cc(OCc1ccc(Oc3ccc(C(F)(F)F)nc3)c(F)c1)nc2=O]

The title compound was prepared by a procedure similar to that described for E1 starting from 8-chloro-1-methyl-3,4-dihydro-1H-pyrimido[1,6-a]pyrimidin-6(2H)-one and (3-fluoro-4-((6-(trifluoromethyl)pyridin-3-yl)oxy)phenyl)methanol.

LC-MS (ESI): m/z 451 [M+H]$^+$; 2.53 min (ret time).

E5

8-((4-(3,4-difluorophenoxy)-3-fluorobenzyl)oxy)-1-methyl-3,4-dihydro-1H-pyrimido[1,6-a]pyrimidin-6(2H)-one

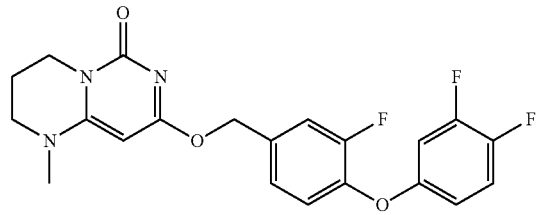 [SMILES: CN1CCCn2c1cc(OCc1ccc(Oc3ccc(F)c(F)c3)c(F)c1)nc2=O]

The title compound was prepared by a procedure similar to that described for E1 starting from 8-chloro-1-methyl-3,4-dihydro-1H-pyrimido[1,6-a]pyrimidin-6(2H)-one and (4-(3,4-difluorophenoxy)-3-fluorophenyl)methanol.

LC-MS (ESI): m/z 418 [M+H]$^+$; 2.68 min (ret time).

E6

8-((4-(4-chloro-3-(trifluoromethyl)phenoxy)benzyl)oxy)-1-methyl-3,4-dihydro-1H-pyrimido[1,6-a]pyrimidin-6(2H)-one

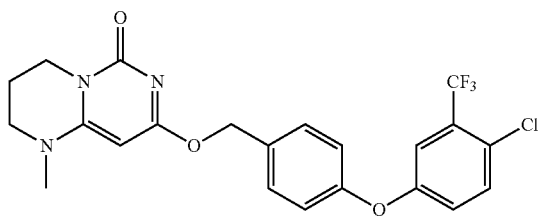 [SMILES: CN1CCCn2c1cc(OCc1ccc(Oc3ccc(Cl)c(C(F)(F)F)c3)cc1)nc2=O]

The title compound was prepared by a procedure similar to that described for E1 starting from 8-chloro-1-methyl-3,4-dihydro-1H-pyrimido[1,6-a]pyrimidin-6(2H)-one and (4-(4-chloro-3-(trifluoromethyl)phenoxy)phenyl)methanol.

LC-MS (ESI): m/z 466 [M+H]$^+$; 3.02 min (ret time).

E7

8-((4-(3,4-dichlorophenoxy)benzyl)oxy)-1-methyl-3,4-dihydro-1H-pyrimido[1,6-a]pyrimidin-6(2H)-one

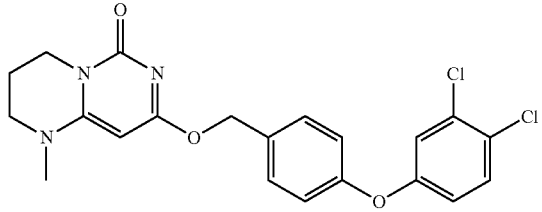 [SMILES: CN1CCCn2c1cc(OCc1ccc(Oc3ccc(Cl)c(Cl)c3)cc1)nc2=O]

The title compound was prepared by a procedure similar to that described for E1 starting from 8-chloro-1-methyl-3,4-dihydro-1H-pyrimido[1,6-a]pyrimidin-6(2H)-one and (4-(3,4-dichlorophenoxy)phenyl)methanol.

LC-MS (ESI): m/z 432 [M+H]⁺; 2.96 min (ret time).

E8

8-((4-fluorobenzyl)oxy)-1-methyl-3,4-dihydro-1H-pyrimido[1,6-a]pyrimidin-6(2H)-one

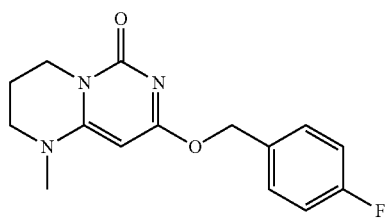 [SMILES: CN1CCCn2c1cc(OCc1ccc(F)cc1)nc2=O]

The title compound was prepared by a procedure similar to that described for E1 starting from 8-chloro-1-methyl-3,4-dihydro-1H-pyrimido[1,6-a]pyrimidin-6(2H)-one and (4-fluorophenyl)methanol.

LC-MS (ESI): m/z 290 [M+H]⁺; 1.87 min (ret time).

E9

8-((4-(4-chloro-3-(trifluoromethyl)phenoxy)phenethyl)amino)-1-methyl-3,4-dihydro-1H-pyrimido[1,6-a]pyrimidin-6(2H)-one, trifluoroacetic acid salt

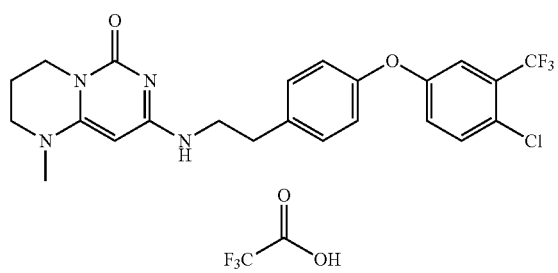

To a microwave reaction tube were added 8-chloro-1-methyl-3,4-dihydro-1H-pyrimido[1,6-a]pyrimidin-6(2H)-one (31 mg, 0.153 mmol), 2-(4-(4-chloro-3-(trifluoromethyl)phenoxy)phenyl)ethanamine (0.058 mL, 0.191 mmol), TEA (0.085 mL, 0.612 mmol) and N,N-dimethylformamide (DMF) (1.5 mL). The reaction mixture was heated at 140° C. for 3 h under microwave radiation. Then TFA was added to adjust pH to ~5. Purification via Mass Directed AutoPrep (MDAP) afforded the title compound as a white solid (6 mg, 6% yield).

LC-MS (ESI): m/z 479 [M+H]⁺; 3.17 min (ret time).

E10

8-((3,4-difluorobenzyl)oxy)-1-methyl-3,4-dihydro-1H-pyrimido[1,6-a]pyrimidin-6(2H)-one, trifluoroacetic acid salt

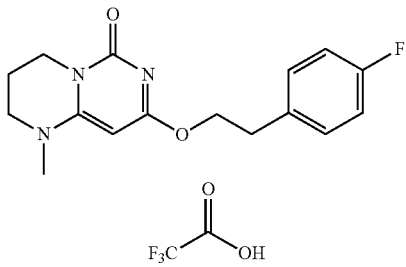

The title compound was prepared by a procedure similar to that described for E1 starting from 8-chloro-1-methyl-3,4-dihydro-1H-pyrimido[1,6-a]pyrimidin-6(2H)-one and (3,4-difluorophenyl)methanol. An exemplary process is shown below: To a solution (3,4-difluorophenyl)methanol (0.079 mL, 0.902 mmol) in N,N-dimethylformamide (DMF) (5 mL), was added NaH (36.1 mg, 0.902 mmol) and stirred for 10 mins. 8-Chloro-1-methyl-3,4-dihydro-1H-pyrimido[1,6-c]pyrimidin-6(2H)-one (60 mg, 0.301 mmol) was added and stirred for 45 mins at rt. 15 Then the resulting solution was quenched by addition of 1 mL aq. NH₄Cl, and then filtered. The resulting solution was purified by MDAP to afford the title compound as a white solid.

LC-MS (ESI): m/z 308 [M+H]⁺; 1.99 min (ret time).

E11

8-(4-fluorophenethoxy)-1-methyl-3,4-dihydro-1H-pyrimido[1,6-a]pyrimidin-6(2H)-one, trifluoroacetic acid salt To a solution of 2-(4-fluorophenyl)ethanol (0.077 mL, 0.902 mmol) in DMF (4 mL) was added potassium tert-butoxide (101 mg, 0.902 mmol). The reaction mixture was then stirred for 10 min at rt. 8-Chloro-1-methyl-3,4-dihydro-1H-pyrimido[1,6-a]pyrimidin-6(2H)-one (60 mg, 0.301 mmol) was charged and stirred for 1 h at rt. The resulting solution was quenched by addition of 1 mL aq. NH₄Cl, and then filtered. Purification via Mass Directed AutoPrep (MDAP) afforded the title compound as a pale yellow solid (42 mg, 33%).

LC-MS (ESI): m/z 308 [M+H]⁺; 2.04 min (ret time).

E12

8-((2,3-difluorobenzyl)oxy)-1-methyl-3,4-dihydro-1H-pyrimido[1,6-a]pyrimidin-6(2H)-one

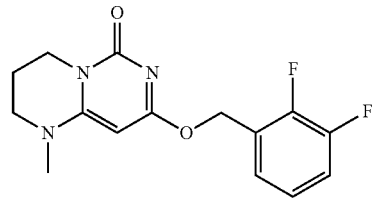 [SMILES: CN1CCCn2c1cc(OCc1cccc(F)c1F)nc2=O]

The title compound was prepared by a procedure similar to that described for E1 starting from 8-chloro-1-methyl-3,4-dihydro-1H-pyrimido[1,6-a]pyrimidin-6(2H)-one and (2,3-difluorophenyl)methanol.

LC-MS (ESI): m/z 308 [M+H]$^+$; 1.91 min (ret time).

E13

8-((3-fluoro-4-(4-fluoro-3-(trifluoromethyl)phenoxy)benzyl)oxy)-1-methyl-3,4-dihydro-1H-pyrimido[1,6-a]pyrimidin-6(2H)-one

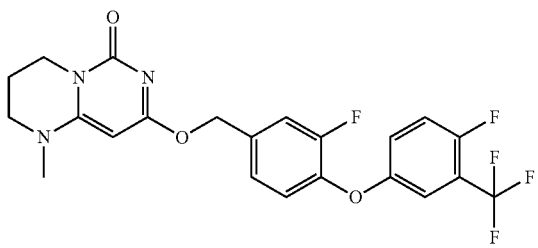 [SMILES: CN1CCCn2c1cc(OCc1ccc(Oc3ccc(F)c(C(F)(F)F)c3)c(F)c1)nc2=O]

The title compound was prepared by a procedure similar to that described for E1 starting from 8-chloro-1-methyl-3,4-dihydro-1H-pyrimido[1,6-a]pyrimidin-6(2H)-one and (3-fluoro-4-(4-fluoro-3-(trifluoromethyl)phenoxy)phenyl)methanol.

LC-MS (ESI): m/z 468 [M+H]$^+$; 2.86 min (ret time).

E14

8-((4-(3,4-difluorophenoxy)benzyl)oxy)-1-methyl-3,4-dihydro-1H-pyrimido[1,6-a]pyrimidin-6(2H)-one

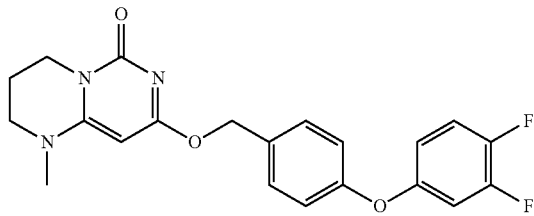 [SMILES: CN1CCCn2c1cc(OCc1ccc(Oc3ccc(F)c(F)c3)cc1)nc2=O]

The title compound was prepared by a procedure similar to that described for E1 starting from 8-chloro-1-methyl-3,4-dihydro-1H-pyrimido[1,6-a]pyrimidin-6(2H)-one and (4-(3,4-difluorophenoxy)phenyl)methanol.

LC-MS (ESI): m/z 400 [M+H]$^+$; 2.50 min (ret time).

E15

8-((4-(3-chloro-4-fluorophenoxy)-3-fluorobenzyl)oxy)-1-methyl-3,4-dihydro-1H-pyrimido[1,6-a]pyrimidin-6(2H)-one

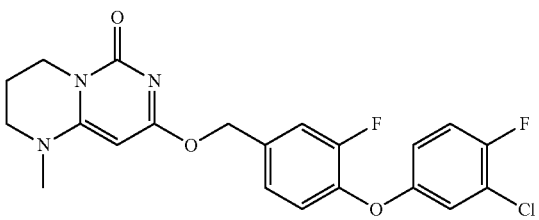 [SMILES: CN1CCCn2c1cc(OCc1ccc(Oc3ccc(F)c(Cl)c3)c(F)c1)nc2=O]

The title compound or its salt was prepared by a procedure similar to that described for E2 starting from (4-(3-chloro-4-fluorophenoxy)-3-fluorophenyl)methanol and 8-chloro-1-methyl-3,4-dihydro-1H-pyrimido[1,6-a]pyrimidin-6(2H)-one.

LC-MS (ESI): m/z 434 [M+1]$^+$; 2.72 min (ret time).

E16

8-((4-(3-chlorophenoxy)-3-fluorobenzyl)oxy)-1-methyl-3,4-dihydro-1H-pyrimido[1,6-a]pyrimidin-6(2H)-one

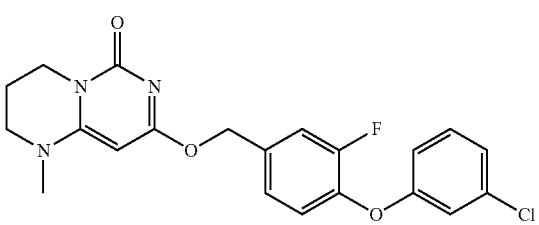 [SMILES: CN1CCCn2c1cc(OCc1ccc(Oc3cccc(Cl)c3)c(F)c1)nc2=O]

The title compound or its salt was prepared by a procedure similar to that described for E2 starting from (4-(3-chloro-4-fluorophenoxy)-3-fluorophenyl)methanol and 8-chloro-1-methyl-3,4-dihydro-1H-pyrimido[1,6-a]pyrimidin-6(2H)-one.

LC-MS (ESI): m/z 416 [M+1]$^+$; 2.73 min (ret time).

E17

8-((4-(3-chloro-4-fluorophenoxy)benzyl)oxy)-1-methyl-3,4-dihydro-1H-pyrimido[1,6-a]pyrimidin-6(2H)-one

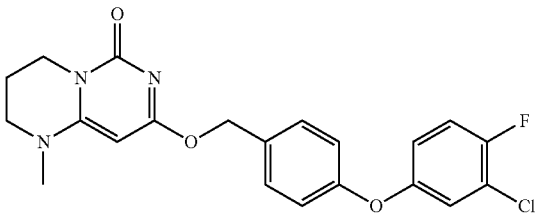 [SMILES: CN1CCCn2c1cc(OCc1ccc(Oc3ccc(F)c(Cl)c3)cc1)nc2=O]

The title compound or its salt was prepared by a procedure similar to that described for E2 starting from and (4-(3- chloro-4-fluorophenoxy)phenyl)methanol 8-chloro-1-methyl-3,4-dihydro-1H-pyrimido[1,6-a]pyrimidin-6(2H)-one.
LC-MS (ESI): m/z 416 [M+1]⁺; 2.69 min (ret time).

E18

8-((4-chloro-3-(trifluoromethyl)benzyl)oxy)-1-methyl-3,4-dihydro-1H-pyrimido[1,6-a]pyrimidin-6(2H)-one

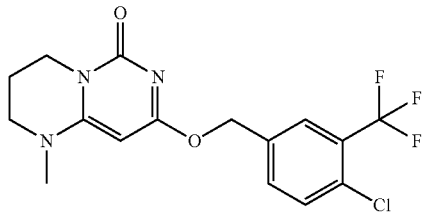 [SMILES: CN1CCCn2c1cc(OCc1ccc(Cl)c(C(F)(F)F)c1)nc2=O]

The title compound or its salt was prepared by a procedure similar to that described for E2 starting from (4-chloro-3-(trifluoromethyl)phenyl)methanol and 8-chloro-1-methyl-3,4-dihydro-1H-pyrimido[1,6-a]pyrimidin-6(2H)-one.
LC-MS (ESI): m/z 374 [M+1]⁺; 2.43 min (ret time).

E19

1-methyl-8-((3-(trifluoromethyl)benzyl)oxy)-3,4-dihydro-1H-pyrimido[1,6-a]pyrimidin-6(2H)-one

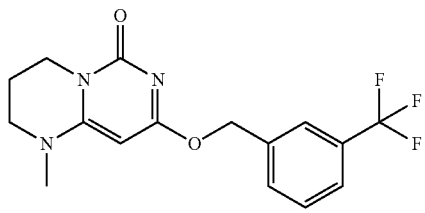 [SMILES: CN1CCCn2c1cc(OCc1cccc(C(F)(F)F)c1)nc2=O]

The title compound or its salt was prepared by a procedure similar to that described for E2 starting from (3-(trifluoromethyl)phenyl)methanol and 8-chloro-1-methyl-3,4-dihydro-1H-pyrimido[1,6-a]pyrimidin-6(2H)-one.
LC-MS (ESI): m/z 340 [M+1]⁺; 2.30 min (ret time).

E20

8-((2,4-difluorobenzyl)oxy)-1-methyl-3,4-dihydro-M-pyrimido[1,6-a]pyrimidin-6(2H)-one

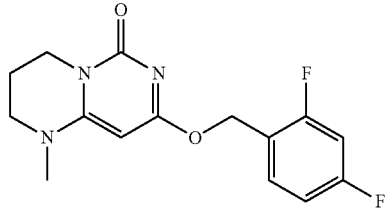 [SMILES: CN1CCCn2c1cc(OCc1ccc(F)cc1F)nc2=O]

The title compound or its salt was prepared by a procedure similar to that described for E2 starting from (2,4-difluorophenyl)methanol and 8-chloro-1-methyl-3,4-dihydro-1H-pyrimido[1,6-a]pyrimidin-6(2H)-one.
LC-MS (ESI): m/z 308 [M+1]⁺; 1.94 min (ret time).

E21

1-methyl-8-((3,4,5-trifluorobenzyl)oxy)-3,4-dihydro-1H-pyrimido[1,6-a]pyrimidin-6(2H)-one

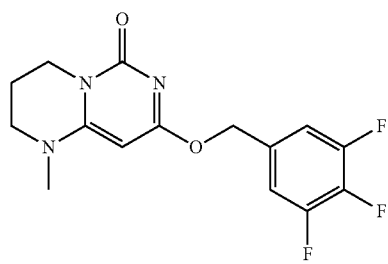

To a solution of NaH (38.3 mg, 0.956 mmol) in DMF (2 mL) was added (3,4,5-trifluorophenyl)methanol (65 mg, 0.401 mmol) at rt. The reaction mixture was stirred for 5 mins at rt, and then 8-chloro-1-methyl-3,4-dihydro-1H-pyrimido[1,6-a]pyrimidin-6(2H)-one trifluoroacetic acid salt (100 mg, 0.319 mmol) was added. The reaction mixture was stirred for another 1 h at rt, quenched with water and then filtered to give clear solution. The solution was purified by MDAP (0.3% TFA in water/MeCN) to afford the title compound as its TFA salt (16 mg, 0.036 mmol, 11.42%).
LC-MS (ESI): m/z 326 [M+1]⁺; 2.13 min (ret time).

E22

8-((3-fluoro-4-(trifluoromethyl)benzyl)oxy)-1-methyl-3,4-dihydro-1H-pyrimido[1,6-a]pyrimidin-6(2H)-one

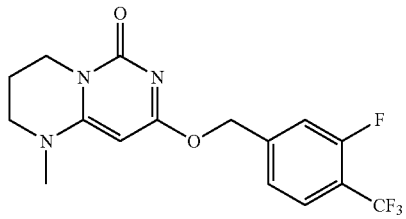 [SMILES: CN1CCCn2c1cc(OCc1ccc(C(F)(F)F)c(F)c1)nc2=O]

The title compound or its salt was prepared by a procedure similar to that described for E2 starting from (3-fluoro-4-(trifluoromethyl)phenyl)methanol and 8-chloro-1-methyl-3,4-dihydro-1H-pyrimido[1,6-a]pyrimidin-6(2H)-one.
LC-MS (ESI): m/z 358 [M+1]⁺; 2.37 min (ret time).

E23

1-methyl-8-((4-(trifluoromethyl)benzyl)oxy)-3,4-dihydro-1H-pyrimido[1,6-a]pyrimidin-6(2H)-one

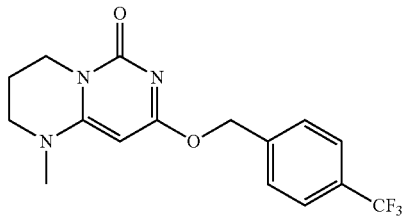 [SMILES: CN1CCCn2c1cc(OCc1ccc(C(F)(F)F)cc1)nc2=O]

The title compound or its salt was prepared by a procedure similar to that described for E2 starting from (4-(trifluoromethyl)phenyl)methanol and 8-chloro-1-methyl-3,4-dihydro-1H-pyrimido[1,6-a]pyrimidin-6(2H)-one.
LC-MS (ESI): m/z 340 [M+1]$^+$; 2.31 min (ret time).

E24

8-((4-fluoro-3-(trifluoromethyl)benzyl)oxy)-1-methyl-3,4-dihydro-1H-pyrimido[1,6-a]pyrimidin-6(2H)-one

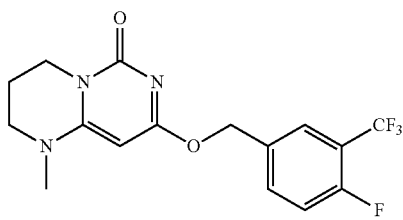 [SMILES: CN1CCCn2c1cc(OCc1ccc(F)c(C(F)(F)F)c1)nc2=O]

The title compound or its salt was prepared by a procedure similar to that described for E2 starting from (4-fluoro-3-(trifluoromethyl)phenyl)methanol and 8-chloro-1-methyl-3,4-dihydro-1H-pyrimido[1,6-a]pyrimidin-6(2H)-one.
LC-MS (ESI): m/z 358 [M+1]$^+$; 2.35 min (ret time).

E25

8-((3-fluoro-4-(3-fluorophenoxyl)benzyl)oxy)-1-methyl-3,4-dihydro-1H-pyrimido[1,6-a]pyrimidin-6(2H)-one

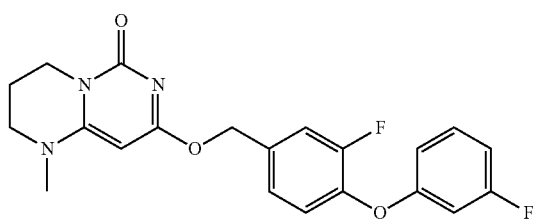 [SMILES: CN1CCCn2c1cc(OCc1ccc(Oc3cccc(F)c3)c(F)c1)nc2=O]

The title compound or its salt was prepared by a procedure similar to that described for E2 starting from (3-fluoro-4-(3-fluorophenoxy)phenyl)methanol and 8-chloro-1-methyl-3,4-dihydro-1H-pyrimido[1,6-a]pyrimidin-6(2H)-one.
LC-MS(ESI): m/z 400 [M+H]$^+$; 2.61 min (ret time)

E26

1-methyl-8-((4-phenoxybenzyl)oxy)-3,4-dihydro-1H-pyrimido[1,6-a]pyrimidin-6(2H)-one

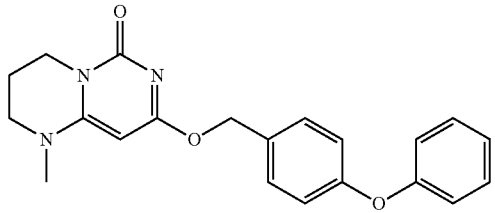 [SMILES: CN1CCCn2c1cc(OCc1ccc(Oc3ccccc3)cc1)nc2=O]

The title compound or its salt was prepared by a procedure similar to that described for E2 starting from (4-phenoxyphenyl)methanol and 8-chloro-1-methyl-3,4-dihydro-1H-pyrimido[1,6-a]pyrimidin-6(2H)-one.
LC-MS (ESI): m/z 364 [M+1]$^+$; 2.58 min (ret time).

E27

3-(((1-methyl-6-oxo-2,3,4,6-tetrahydro-1H-pyrimido[1,6-a]pyrimidin-8-yl)oxy)methyl)benzonitrile

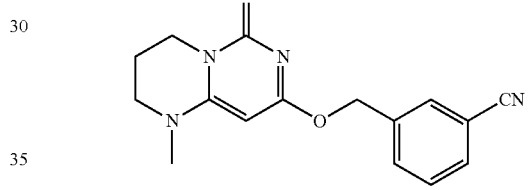

The title compound or its salt was prepared by a procedure similar to that described for E2 starting from 3-(hydroxymethyl)benzonitrile and 8-chloro-1-methyl-3,4-dihydro-1H-pyrimido[1,6-a]pyrimidin-6(2H)-one.
LC-MS (ESI): m/z 297 [M+1]$^+$; 1.76 min (ret time).

E28

8-((3-fluoro-4-(3-(trifluoromethyl)phenoxy)benzyl)oxy)-1-methyl-3,4-dihydro-1H-pyrimido[1,6-a]pyrimidin-6(2H)-one

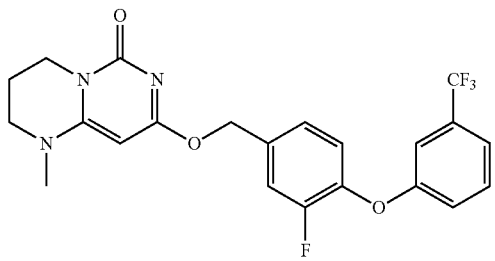 [SMILES: CN1CCCn2c1cc(OCc1ccc(Oc3cccc(C(F)(F)F)c3)c(F)c1)nc2=O]

The title compound or its salt was prepared by a procedure similar to that described for E2 starting from (3-fluoro-4-(3-(trifluoromethyl)phenoxy)phenyl)methanol and 8-chloro-1-methyl-3,4-dihydro-1H-pyrimido[1,6-a]pyrimidin-6(2H)-one.
LC-MS (ESI): m/z 450 [M+1]$^+$; 2.91 (ret time).

E29

5-(((1-methyl-6-oxo-2,3,4,6-tetrahydro-1H-pyrimido[1,6-a]pyrimidin-8-yl)oxy)methyl)-2-(4-(trifluoromethyl)phenoxy)benzonitrile

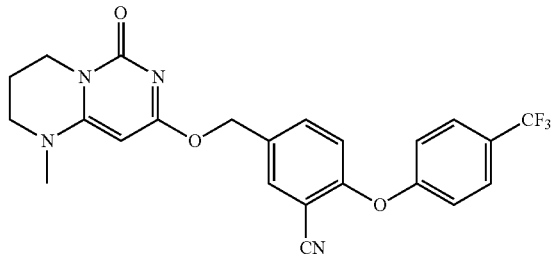 [SMILES: CN1CCCn2c1cc(OCc1ccc(Oc3ccc(C(F)(F)F)cc3)c(C#N)c1)nc2=O]

The title compound or its salt was prepared by a procedure similar to that described for E2 starting from 5-(hydroxymethyl)-2-(4-(trifluoromethyl)phenoxy)benzonitrile and 8-chloro-1-methyl-3,4-dihydro-1H-pyrimido[1,6-a]pyrimidin-6(2H)-one.

LC-MS (ESI): m/z 457 [M+1]$^+$; 2.82 (ret time).

E30

2-(4-fluorophenoxy)-5-(((1-methyl-6-oxo-2,3,4,6-tetrahydro-1H-pyrimido[1,6-a]pyrimidin-8-yl)oxy)methyl)benzonitrile

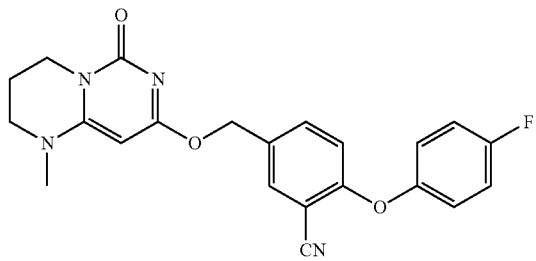 [SMILES: CN1CCCn2c1cc(OCc1ccc(Oc3ccc(F)cc3)c(C#N)c1)nc2=O]

The title compound or its salt was prepared by a procedure similar to that described for E2 starting from 2-(4-fluorophenoxy)-5-(hydroxymethyl)benzonitrile and 8-chloro-1-methyl-3,4-dihydro-1H-pyrimido[1,6-a]pyrimidin-6(2H)-one.

LC-MS (ESI): m/z 407 [M+1]$^+$; 2.52 (ret time).

E31

8-((3,5-difluorobenzyl)oxy)-1-methyl-3,4-dihydro-1H-pyrimido[1,6-a]pyrimidin-6(2H)-one

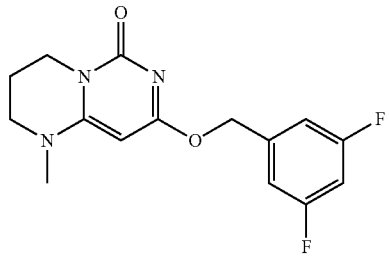 [SMILES: CN1CCCn2c1cc(OCc1cc(F)cc(F)c1)nc2=O]

The title compound or its salt was prepared by a procedure similar to that described for E2 starting from (3,5-difluorophenyl)methanol and 8-chloro-1-methyl-3,4-dihydro-1H-pyrimido[1,6-a]pyrimidin-6(2H)-one.

LC-MS (ESI): m/z 308 [M+1]$^+$; 1.97 (ret time).

E32

8-((3-fluoro-4-((6-(trifluoromethyl)pyridin-2-yl)oxy)benzyl)oxy)-1-methyl-3,4-dihydro-1H-pyrimido[1,6-a]pyrimidin-6(2H)-one

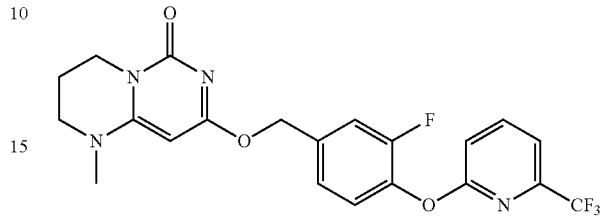

The title compound or its salt was prepared by a procedure similar to that described for E2 starting from (3-fluoro-4-((6-(trifluoromethyl)pyridine-2-yl)oxy)phenyl)methanol and 8-chloro-1-methyl-3,4-dihydro-1H-pyrimido[1,6-a]pyrimidin-6(2H)-one.

LC-MS(ESI): m/z 451 [M+H]$^+$; 2.65 min (ret time).

E33

3-fluoro-5-(((1-methyl-6-oxo-2,3,4,6-tetrahydro-1H-pyrimido[1,6-a]pyrimidin-8-yl)oxy)methyl)benzonitrile

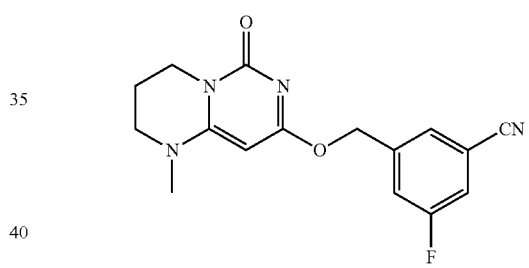

The title compound or its salt was prepared by a procedure similar to that described for E2 starting from 3-fluoro-5-(hydroxymethyl)benzonitrile and 8-chloro-1-methyl-3,4-dihydro-1H-pyrimido[1,6-a]pyrimidin-6(2H)-one.

LC-MS (ESI): m/z 315 [M+1]$^+$; 1.87 (ret time).

E34

2-(3,4-difluorophenoxy)-5-(((1-methyl-6-oxo-2,3,4,6-tetrahydro-1H-pyrimido[1,6-a]pyrimidin-8-yl)oxy)methyl)benzonitrile

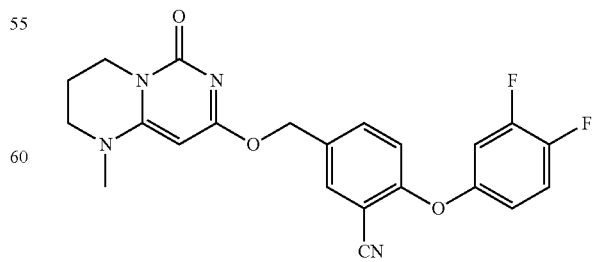

The title compound or its salt was prepared by a procedure similar to that described for E2 starting from 2-(3,4-difluororophenoxy)-5-(hydroxymethyl)benzonitrile and 8-chloro-1-methyl-3,4-dihydro-1H-pyrimido[1,6-a]pyrimidin-6(2H)-one.

LC-MS (ESI): m/z 425 [M+1]⁺; 2.59 (ret time).

E35

1-methyl-8-((2,4,5-trifluorobenzyl)oxy)-3,4-dihydro-1H-pyrimido[1,6-a]pyrimidin-6(2H)-one

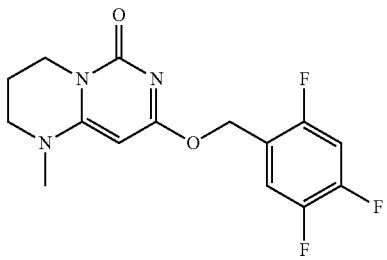 [SMILES: CN1CCCn2c1cc(OCc1cc(F)c(F)cc1F)nc2=O]

The title compound or its salt was prepared by a procedure similar to that described for E2 starting from (2,4,5-trifluorophenyl)methanol and 8-chloro-1-methyl-3,4-dihydro-1H-pyrimido[1,6-a]pyrimidin-6(2H)-one.

LC-MS (ESI): m/z 326 [M+1]⁺; 2.02 (ret time).

E36

8-[2-(4-Methoxy-phenyl)-ethoxy]-1-methyl-1,2,3,4-tetrahydro-pyrimido[1,6-a]pyrimidin-6-one

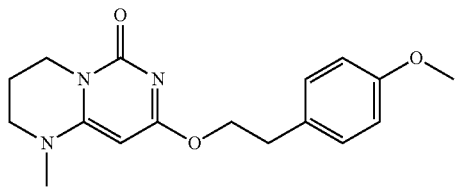 [SMILES: COc1ccc(CCOc2cc3n(c(=O)n2)CCCN3C)cc1]

To a solution of 2-(4-methoxyphenyl)ethanol (183 mg, 1.202 mmol) and 8-chloro-1-methyl-3,4-dihydro-1H-pyrimido[1,6-a]pyrimidin-6(2H)-one (200 mg, 1.002 mmol) in dimethyl sulfoxide (DMSO) (5 mL) stirred at room temp was added NaH (100 mg, 2.505 mmol) portionwise. The reaction mixture was stirred at room temp for 2 hr. The reaction was quenched with water and purified by prep-HPLC to give the title product as a white solid (150 mg).

LC-MS (ESI): m/z 316 [M+H]⁺; 0.72 min (ret time).

E37

8-((3-fluorobenzyl)oxy)-1-methyl-3,4-dihydro-1H-pyrimido[1,6-a]pyrimidin-6(2H)-one

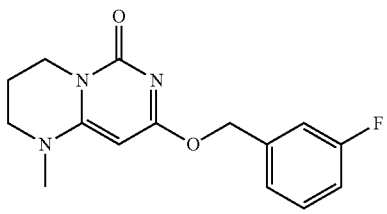 [SMILES: CN1CCCn2c1cc(OCc1cccc(F)c1)nc2=O]

The title compound or its salt was prepared by a procedure similar to that described for E2 starting from (3-fluorophenyl)methanol and 8-chloro-1-methyl-3,4-dihydro-1H-pyrimido[1,6-a]pyrimidin-6(2H)-one.

LC-MS (ESI): m/z 290 [M+1]⁺; 1.89 (ret time).

E38

8-((3-fluoro-4-((6-(trifluoromethyl)pyridin-3-yl)oxy)benzyl)oxy)-1-isopropyl-3,4-dihydro-1H-pyrimido[1,6-a]pyrimidin-6(2H)-one

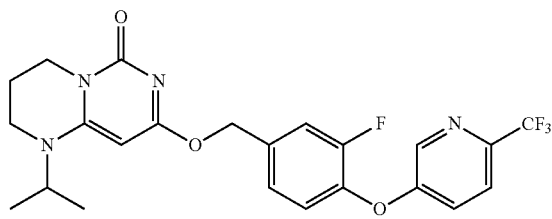 [SMILES: CC(C)N1CCCn2c1cc(OCc1ccc(Oc3ccc(C(F)(F)F)nc3)c(F)c1)nc2=O]

To a solution of (3-fluoro-4-((6-(trifluoromethyl)pyridin-3-yl)oxy)phenyl)methanol (126 mg, 0.439 mmol) and 8-chloro-1-isopropyl-3,4-dihydro-1H-pyrimido[1,6-a]pyrimidin-6(2H)-one (20 mg, 0.088 mmol) in N,N-dimethylformamide (DMF) (8 mL), was added NaH (35.1 mg, 0.878 mmol) 25 and stirred for 1 h at rt. The reaction mixture was quenched by addition of sat. aq. NH₄Cl solution and was filtered. The solution was purified by MDAP to afford the desired product as a white solid.

LC-MS(ESI): m/z 479 [M+H]⁺; 2.84 min (ret time)

E39

1-Methyl-8-[2-(4-trifluoromethyl-phenyl)-ethoxy]-1,2,3,4-tetrahydro-pyrimido[1,6-a]pyrimidin-6-one

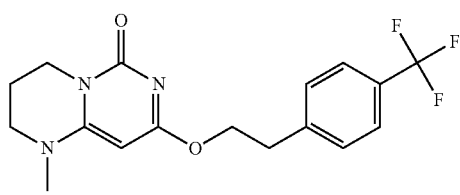 [SMILES: CN1CCCn2c1cc(OCCc1ccc(C(F)(F)F)cc1)nc2=O]

The title compound or its salt was prepared by a procedure similar to that described for E11 starting from 2-(4-(trifluoromethyl)phenyl)ethanol and 8-chloro-1-methyl-3,4-dihydro-1H-pyrimido[1,6-a]pyrimidin-6(2H)-one.

LC-MS (ESI): m/z 354 [M+H]⁺; 0.94 min (ret time).

E40

8-((3,4-difluorobenzyl)oxy)-1-isopropyl-3,4-dihydro-1H-pyrimido[1,6-a]pyrimidin-6(2H)-one

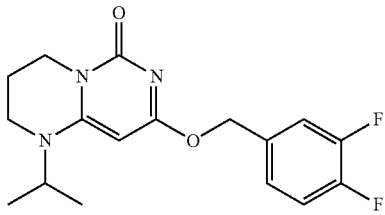 [SMILES: CC(C)N1CCCn2c1cc(OCc1ccc(F)c(F)c1)nc2=O]

To a solution of (3,4-difluorophenyl)methanol (111 mg, 0.769 mmol) and 8-chloro-1-isopropyl-3,4-dihydro-1H-pyrimido[1,6-a]pyrimidin-6(2H)-one (50 mg, 0.220 mmol) in N,N-dimethylformamide (DMF) (8 mL) was added NaH (26.3 mg, 0.659 mmol) and stirred for 1 h at rt. The reaction mixture was quenched by addition of sat. aq. NH$_4$Cl solution and was filtered. The solution was purified by MDAP to afford TFA salt of the title product as a white solid (20 mg, 20.3%). 20

LC-MS (ESI): m/z 336 [M+H]$^+$; 2.25 min (ret time).

E41

8-((4-chlorobenzyl)oxy)-1-isopropyl-3,4-dihydro-1H-pyrimido[1,6-a]pyrimidin-6(2H)-one

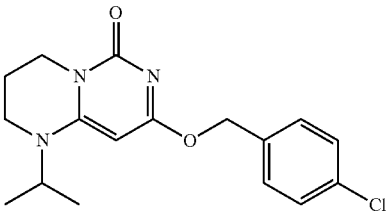 [SMILES: CC(C)N1CCCn2c1cc(OCc1ccc(Cl)cc1)nc2=O]

The title compound or its salt was prepared by a procedure similar to that described for E2 starting from (4-chlorophenyl)methanol and 8-chloro-1-isopropyl-3,4-dihydro-1H-pyrimido[1,6-a]pyrimidin-6(2H)-one.

LC-MS (ESI): m/z 334 [M+H]$^+$; 2.42 min (ret time).

E42 isopropyl-8-((3,4,5-trifluorobenzyl)oxy)-3,4-dihydro-1H-pyrimido[1,6-a]pyrimidin-6(2H)-one

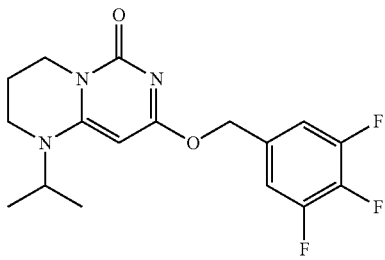 [SMILES: CC(C)N1CCCn2c1cc(OCc1cc(F)c(F)c(F)c1)nc2=O]

To a solution of (3,4,5-trifluorophenyl)methanol (214 mg, 1.318 mmol) and 8-chloro-1-isopropyl-3,4-dihydro-1H-pyrimido[1,6-a]pyrimidin-6(2H)-one (50 mg, 0.220 mmol) in N,N dimethylformamide (DMF) (8 mL), was added NaH (52.7 mg, 1.318 mmol) and stirred for 1 h at rt. The reaction mixture was quenched by addition of sat. NH$_4$Cl and then filtered. The solution was purified by MDAP to afford the TFA salt of the title compound (5 mg, 4.8%).

LC-MS(ESI): m/z 354 [M+H]$^+$; 2.45 min (ret time).

E43

8-[2-(3,4-Dichloro-phenyl)-ethoxy]-1-methyl-1,2,3,4-tetrahydro-pyrimido[1,6-a]pyrimidin-6-one

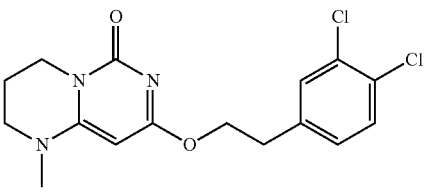 [SMILES: CN1CCCn2c1cc(OCCc1ccc(Cl)c(Cl)c1)nc2=O]

The title compound or its salt was prepared by a procedure similar to that described for E11 starting from 2-(3,4-dichlorophenyl)ethanol and 8-chloro-1-methyl-3,4-dihydro-1H-pyrimido[1,6-a]pyrimidin-6(2H)-one.

LC-MS (ESI): m/z 354 [M+H]+; 1.052 min (ret time).

E44

1-Methyl-8-[2-(3,4,5-trifluoro-phenyl)-ethoxy]-1,2,3,4-tetrahydro-pyrimido[1,6-a]pyrimidin-6-one

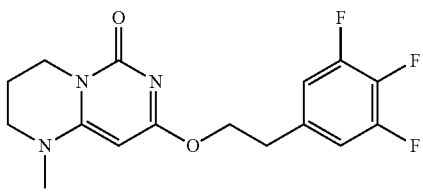 [SMILES: CN1CCCn2c1cc(OCCc1cc(F)c(F)c(F)c1)nc2=O]

The title compound or its salt was prepared by a procedure similar to that described for E11 starting from 2-(3,4,5-trifluorophenyl)ethanol and 8-chloro-1-methyl-3,4-dihydro-1H-pyrimido[1,6-a]pyrimidin-6(2H)-one.

LC-MS (ESI): m/z 340 [M+H]+; 0.908 min (ret time).

E45

8-[2-(2,3-Difluoro-phenyl)-ethoxy]-1-methyl-1,2,3,4-tetrahydro-pyrimido[1,6-a]pyrimidin-6-one

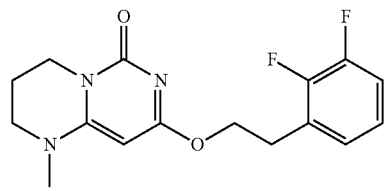 [SMILES: CN1CCCn2c1cc(OCCc1cccc(F)c1F)nc2=O]

The title compound or its salt was prepared by a procedure similar to that described for E11 starting from 2-(2,3-difluorophenyl)ethanol and 8-chloro-1-methyl-3,4-dihydro-1H-pyrimido[1,6-a]pyrimidin-6(2H)-one.

LC-MS (ESI): m/z 322 [M+H]$^+$; 0.632 min (ret time).

E46

8-[2-(2,4-Difluoro-phenyl)-ethoxy]-1-methyl-1,2,3,4-tetrahydro-pyrimido[1,6-a]pyrimidin-6-one

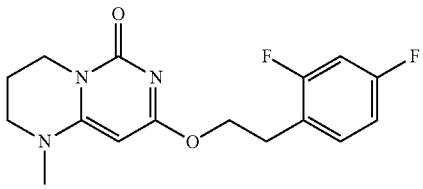 [SMILES: CN1CCCn2c1cc(OCCc1ccc(F)cc1F)nc2=O]

The title compound or its salt was prepared by a procedure similar to that described for E11 starting from 2-(2,4-difluorophenyl)ethanol and 8-chloro-1-methyl-3,4-dihydro-1H-pyrimido[1,6-a]pyrimidin-6(2H)-one.

LC-MS (ESI): m/z 322 [M+H]$^+$; 1.06 min (ret time).

E47

8-(3-fluoro-4-methylphenethoxy)-1-methyl-3,4-dihydro-1H-pyrimido[1,6-a]pyrimidin-6(2H)-one

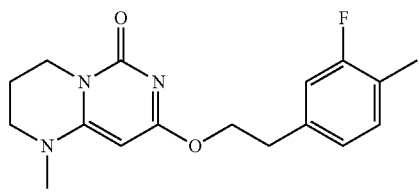 [SMILES: Cc1ccc(CCOc2cc3n(c(=O)n2)CCCN3C)cc1F]

The title compound or its salt was prepared by a procedure similar to that described for E11 starting from of 2-(3-fluoro-4-methylphenyl)ethanol and 8-chloro-1-methyl-3,4-dihydro-1H-pyrimido[1,6-a]pyrimidin-6(2H)-one.

LC-MS (ESI): m/z 318 [M+H]+; 0.79 min (ret time).

E48

3-[2-(1-Methyl-6-oxo-1,3,4,6-tetrahydro-2H-pyrimido[1,6-a]pyrimidin-8-yloxy)-ethyl]-benzonitrile

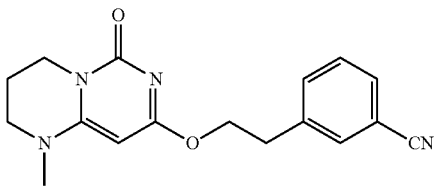 [SMILES: CN1CCCn2c1cc(OCCc1cccc(C#N)c1)nc2=O]

The title compound or its salt was prepared by a procedure similar to that described for E11 starting from of 3-(2-hydroxyethyl)benzonitrile and 8-chloro-1-methyl-3,4-dihydro-1H-pyrimido[1,6-a]pyrimidin-6(2H)-one.

LC-MS (ESI): m/z 340 [M+H]+; 0.908 min (ret time).

E49

8-[2-(4-Chloro-phenyl)-ethoxy]-1-methyl-1,2,3,4-tetrahydro-pyrimido[1,6-a]pyrimidin-6-one

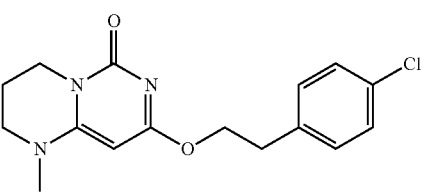 [SMILES: CN1CCCn2c1cc(OCCc1ccc(Cl)cc1)nc2=O]

The title compound or its salt was prepared by a procedure similar to that described for E11 starting from of 2-(4-chlorophenyl)ethanol and 8-chloro-1-methyl-3,4-dihydro-1H-pyrimido[1,6-a]pyrimidin-6(2H)-one.

LC-MS (ESI): m/z 311 [M+H]+; 0.401 min (ret time).

E50

8-((3-fluoro-4-(trifluoromethyl)benzyl)oxy)-1-isopropyl-3,4-dihydro-1H-pyrimido[1,6-a]pyrimidin-6(2H)-one

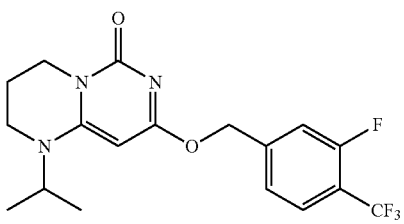 [SMILES: CC(C)N1CCCn2c1cc(OCc1ccc(C(F)(F)F)c(F)c1)nc2=O]

The title compound or its salt was prepared by a procedure similar to that described for E2 starting from (3-fluoro-4-(trifluoromethyl)phenyl)methanol and 8-chloro-1-isopropyl-3,4-dihydro-1H-pyrimido[1,6-a]pyrimidin-6(2H)-one.

LC-MS (ESI): m/z 386 [M+H]$^+$; 2.63 min (ret time).

E51

8-(2-(6-(3,4-difluorophenoxy)pyridin-3-yl)ethoxy)-1-methyl-3,4-dihydro-1H-pyrimido[1,6-a]pyrimidin-6(2H)-one

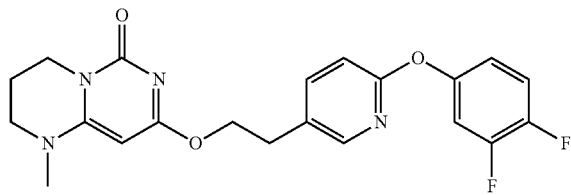 [SMILES: CN1CCCn2c1cc(OCCc1ccc(Oc3ccc(F)c(F)c3)nc1)nc2=O]

The title compound or its salt was prepared by a procedure similar to that described for E2 starting from 2-(6-(3,4-difluorophenoxy)pyridin-3-yl)ethanol and 8-chloro-1-methyl-3,4-dihydro-1H-pyrimido[1,6-a]pyrimidin-6(2H)-one.

LC-MS (ESI): m/z 415 [M+1]$^+$; 2.43 (ret time).

E52

4-[2-(1-Methyl-6-oxo-1,3,4,6-tetrahydro-2H-pyrimido[1,6-a]pyrimidin-8-yloxy)-ethyl]-benzonitrile

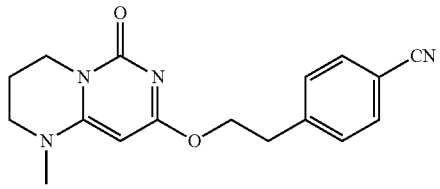 [SMILES: CN1CCCn2c1cc(OCCc1ccc(C#N)cc1)nc2=O]

The title compound or its salt was prepared by a procedure similar to that described for E11 starting from of 4-(2-hydroxyethyl)benzonitrile and 8-chloro-1-methyl-3,4-dihydro-1H-pyrimido[1,6-a]pyrimidin-6(2H)-one.
LC-MS (ESI): m/z 311 [M+H]+; 0.867 min (ret time).

E53

5-(((6-oxo-2,3,4,6-tetrahydro-1H-pyrimido[1,6-a]pyrimidin-8-yl)oxy)methyl)-2-(3-(trifluoromethyl)phenoxy)benzonitrile

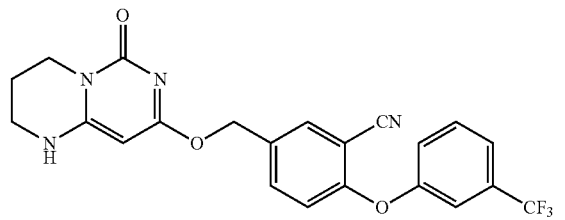 [SMILES: N#Cc1cc(COc2cc3n(c(=O)n2)CCCN3)ccc1Oc1cccc(C(F)(F)F)c1]

To a solution of 5-(((6-((3-bromopropyl)amino)-2-chloropyrimidin-4-yl)oxy)methyl)-2-(3-(trifluoromethyl)phenoxy)benzonitrile (350 mg, 0.646 mmol) in water (5 mL) and 1,4-dioxane (5.00 mL) was added $K_2CO_3$ (179 mg, 1.292 mmol) at room temperature. The reaction mixture was heated to 50° C. for 2 hrs. The solution was purified by reverse phase column chromatography (120 g) using water (contained 0.3% TFA) and MeCN as eluent to afford 5-(((6-oxo-2,3,4,6-tetrahydro-1H-pyrimido[1,6-a]pyrimidin-8-yl)oxy)methyl)-2-(3-(trifluoromethyl)phenoxy)benzonitrile, trifluoroacetic acid salt (11 mg, 0.020 mmol, 3.06% yield).
LC-MS (ESI): m/z 443 [M+1]+; 2.69 (ret time).

E54

8-(2-(5-(3-chloro-4-(trifluoromethyl)phenoxy)pyridin-2-yl)ethoxy)-1-methyl-3,4-dihydro-1H-pyrimido[1,6-a]pyrimidin-6(2H)-one

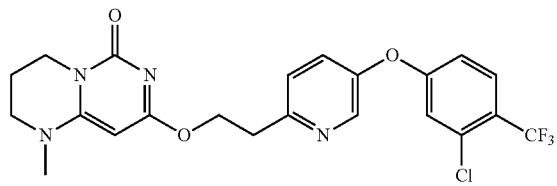 [SMILES: CN1CCCn2c1cc(OCCc1ccc(Oc3ccc(C(F)(F)F)c(Cl)c3)cn1)nc2=O]

The title compound or its salt was prepared by a procedure similar to that described for E2 starting from 2-(5-(4-chloro-3-(trifluoromethyl)phenoxy)pyridin-2-yl)ethanol and 8-chloro-1-methyl-3,4-dihydro-1H-pyrimido[1,6-a]pyrimidin-6(2H)-one.
LC-MS (ESI): m/z 481 [M+1]+; 2.74 (ret time).

E55

8-(4-(4-chloro-3-(trifluoromethyl)phenoxy)phenethoxy)-1-methyl-3,4-dihydro-1H-pyrimido[1,6-a]pyrimidin-6(2H)-one

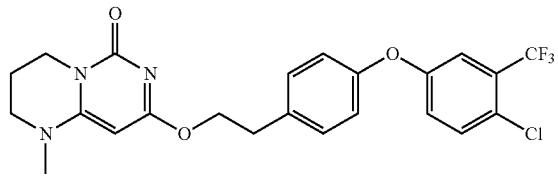 [SMILES: CN1CCCn2c1cc(OCCc1ccc(Oc3ccc(Cl)c(C(F)(F)F)c3)cc1)nc2=O]

The title compound or its salt was prepared by a procedure similar to that described for E2 starting from 2-(4-(4-chloro-3-(trifluoromethyl)phenoxy)phenyl)ethanol and 8-chloro-1-methyl-3,4-dihydro-1H-pyrimido[1,6-a]pyrimidin-6(2H)-one.
LC-MS (ESI): m/z 480 [M+H]+; 3.08 min (ret time)

E56

5-(((1-methyl-6-oxo-2,3,4,6-tetrahydro-1H-pyrimido[1,6-a]pyrimidin-8-yl)oxy)methyl)-2-((6-methylpyridin-3-yl)oxy)benzonitrile

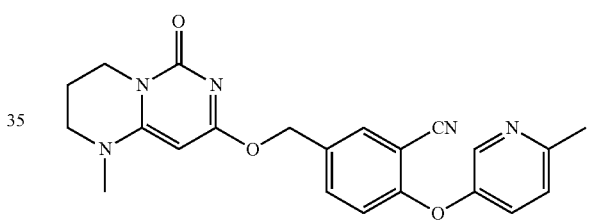

The title compound or its salt was prepared by a procedure similar to that described for E2 starting from 5-(hydroxymethyl)-2-((6-methylpyridin-3-yl)oxy)benzonitrile and 8-chloro-1-methyl-3,4-dihydro-1H-pyrimido[1,6-a]pyrimidin-6(2H)-one.
LC-MS (ESI): m/z 404 [M+H]+; 1.68 min (ret time)

E57 methyl-8-(4-(((6-(trifluoromethyl)pyridin-2-yl)oxy)phenethoxy)-3,4-dihydro-1H-pyrimid[1,6-a]pyrimidin-6(2H)-one

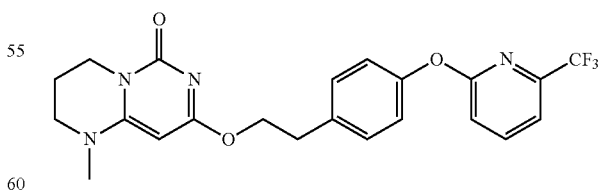

The title compound or its salt was prepared by a procedure similar to that described for E2 starting from 2-(4-((6-(trifluoromethyl)pyridin-2-yl)oxy)phenyl)ethanol and 8-chloro-1-methyl-3,4-dihydro-1H-pyrimido[1,6-a]pyrimidin-6(2H)-one.
LC-MS (ESI): m/z 447 [M+H]+; 2.68 min (ret time)

E58

8-((4-(3,5-difluorophenoxy)-3-fluorobenzyl)oxy)-1-methyl-3,4-dihydro-1H-pyrimido[1,6-a]pyrimidin-6(2H)-one

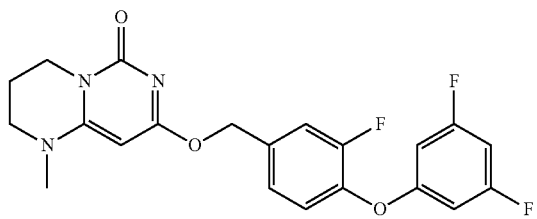

The title compound or its salt was prepared by a procedure similar to that described for E2 starting from (4-(3,5-difluorophenoxy)-3-fluorophenyl)methanol and 8-chloro-1-methyl-3,4-dihydro-1H-pyrimido[1,6-a]pyrimidin-6(2H)-one.
LC-MS (ESI): m/z 418 [M+H]$^+$; 2.74 min (ret time)

E59

8-(3,4-Difluoro-benzylamino)-1-methyl-1,2,3,4-tetrahydro-pyrimido[1,6-a]pyrimidin-6-one

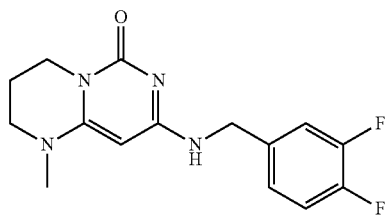 [SMILES: CN1CCCn2c1cc(NCc1ccc(F)c(F)c1)nc2=O]

To a solution of 8-chloro-1-methyl-3,4-dihydro-1H-pyrimido[1,6-a]pyrimidin-6(2H)-one (100 mg, 0.501 mmol) and (3,4-difluorophenyl)methanamine (86 mg, 0.601 mmol) in dimethyl sulfoxide (DMSO) (2 mL) stirred in air at rt was added K$_2$CO$_3$ (208 mg, 1.503 mmol). The reaction mixture was stirred at 100° C. for 16 hr. The solution was filtered and the filtrate was purified by pre-HPLC to give the TFA salt of the title product as white solid (100 mg).
LC-MS (ESI): m/z 307 [M+H]+; 0.94 min (ret time).

E60

1-methyl-8-(phenethylthio)-3,4-dihydro-1H-pyrimido[1,6-a]pyrimidin-6(2H)-one

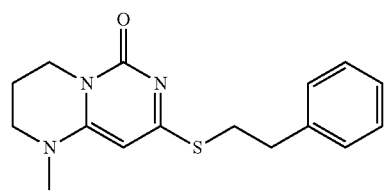 [SMILES: CN1CCCn2c1cc(SCCc1ccccc1)nc2=O]

To a solution of 8-chloro-1-methyl-3,4-dihydro-1H-pyrimido[1,6-a]pyrimidin-6(2H)-one (100 mg, 0.501 mmol) and 2-phenylethanethiol (83 mg, 0.601 mmol) in dimethyl sulfoxide (DMSO) (3 mL) was added K$_2$CO$_3$ (208 mg, 1.503 mmol). The reaction mixture was stirred at 100° C. for 16 hr. The crude product was purified by Prep-HPLC to afford 70 mg title product.
LC-MS(ESI): m/z: 302 (M+H)+; 0.91 min(ret time)

E61

8-(4-Fluoro-benzylamino)-1-methyl-1,2,3,4-tetrahydro-pyrimido[1,6-a]pyrimidin-6-one

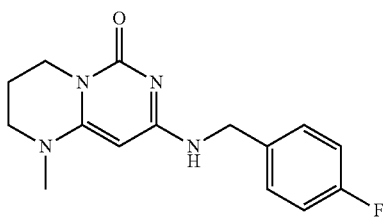

The title compound or its salt was prepared by a procedure similar to that described for E59 starting from (4-fluorophenyl)methanamine and 8-chloro-1-methyl-3,4-dihydro-1H-pyrimido[1,6-a]pyrimidin-6(2H)-one.
LC-MS (ESI): m/z 289 [M+H]+; 0.92 min (ret time).

E62

1-methyl-8-((2-methylbenzyl)thio)-3,4-dihydro-1H-pyrimido[1,6-a]pyrimidin-6(2H)-one

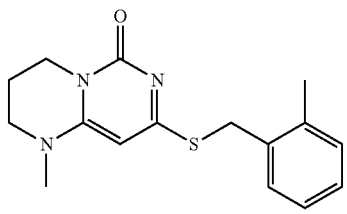 [SMILES: Cc1ccccc1CSc1cc2n(c(=O)n1)CCCN2C]

To a suspension of 8-chloro-1-methyl-3,4-dihydro-1H-pyrimido[1,6-a]pyrimidin-6(2H)-one (200 mg, 1.002 mmol) and o-tolylmethanethiol (166 mg, 1.202 mmol) in tetrahydrofuran (THF) (5 mL) stirred in air at room temperature was added potassium tert-butoxide (112 mg, 1.002 mmol) in one charge. The reaction mixture was stirred at rt for 3 hr. The resulting mixture was concentrated and purified by prep-HPLC to give 50 mg 1-methyl-8-((2-methylbenzyl)thio)-3,4-dihydro-1H-pyrimido[1,6-a]pyrimidin-6(2H)-one (50 mg, 0.158 mmol, 15.73% yield).
LC-MS (ESI): m/z 302 [M+H]+; 1.22 min (ret time).

E63

8-((2-chlorobenzyl)thio)-1-methyl-3,4-dihydro-1H-pyrimido[1,6-a]pyrimidin-6(2H)-one

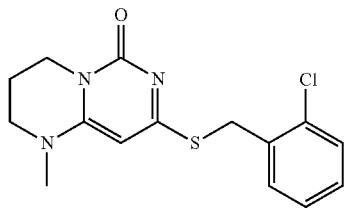 [SMILES: CN1CCCn2c1cc(SCc1ccccc1Cl)nc2=O]

The title compound or it salt was prepared by a procedure similar to that described for E62 starting from (2-chlorophenyl)methanethiol and 8-chloro-1-methyl-3,4-dihydro-1H-pyrimido[1,6-a]pyrimidin-6(2H)-one.

LC-MS (ESI): m/z 322 [M+H]+; 1.23 min (ret time).

E64

8-((2,4-difluorobenzyl)amino)-1-methyl-3,4-dihydro-1H-pyrimido[1,6-a]pyrimidin-6(2H)-one

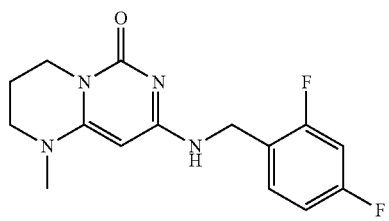

The title compound or its salt was prepared by a procedure similar to that described for E59 starting from (2,4-difluorophenyl)methanamine and 8-chloro-1-methyl-3,4-dihydro-1H-pyrimido[1,6-a]pyrimidin-6(2H)-one.

LC-MS (DAD): m/z 307.1 [M+H]$^+$; 0.935 min (ret time)

E65

8-((3,5-difluorobenzyl)amino)-1-methyl-3,4-dihydro-1H-pyrimido[1,6-a]pyrimidin-6(2H)-one

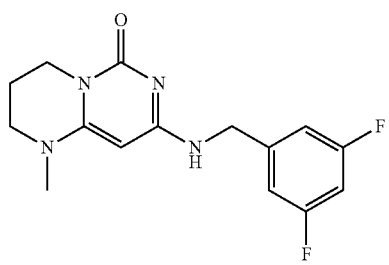 [SMILES: CN1CCCn2c1cc(NCc1cc(F)cc(F)c1)nc2=O]

The title compound or its salt was prepared by a procedure similar to that described for E59 starting from (3,5-difluorophenyl)methanamine and 8-chloro-1-methyl-3,4-dihydro-1H-pyrimido[1,6-a]pyrimidin-6(2H)-one.

LC-MS (DAD): m/z 307.1 [M+H]$^+$; 0.933 min (ret time)

E66

8-(4-Fluoro-benzylsulfanyl)-1-methyl-1,2,3,4-tetrahydro-pyrimido[1,6-a]pyrimidin-6-one

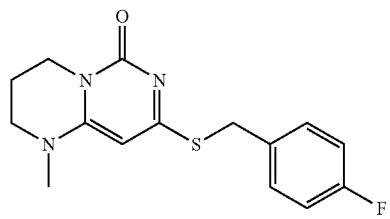

The title compound or its salt was prepared by a procedure similar to that described for E62 starting from (4-fluorophenyl)methanethiol and 8-chloro-1-methyl-3,4-dihydro-1H-pyrimido[1,6-a]pyrimidin-6(2H)-one.

LC-MS (ESI): m/z 306 [M+H]+; 1.51 min (ret time).

E67

8-(4-Chloro-benzylsulfanyl)-1-methyl-1,2,3,4-tetrahydro-pyrimido[1,6-a]pyrimidin-6-one

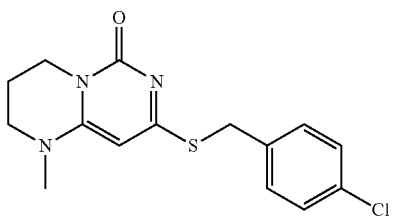 [SMILES: CN1CCCn2c1cc(SCc1ccc(Cl)cc1)nc2=O]

The title compound or its salt was prepared by a procedure similar to that described for E62 starting from (4-chlorophenyl)methanethiol and 8-chloro-1-methyl-3,4-dihydro-1H-pyrimido[1,6-a]pyrimidin-6(2H)-one.

LC-MS (ESI): m/z 322 [M+H]$^+$; 0.69 min (ret time).

E68

8-(4-Chloro-3-fluoro-benzylamino)-1-methyl-1,2,3,4-tetrahydro-pyrimido[1,6-a]pyrimidin-6-one

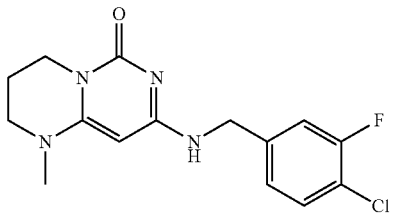 [SMILES: CN1CCCn2c1cc(NCc1ccc(Cl)c(F)c1)nc2=O]

The title compound or its salt was prepared by a procedure similar to that described for E59 starting from (4-chloro-3-fluorophenyl)methanamine and 8-chloro-1-methyl-3,4-dihydro-1H-pyrimido[1,6-a]pyrimidin-6(2H)-one.

LC-MS (ESI): m/z 323 [M+H]$^+$; 0.78 min (ret time).

E69

8-(3-Fluoro-benzylamino)-1-methyl-1,2,3,4-tetrahydro-pyrimido[1,6-a]pyrimidin-6-one

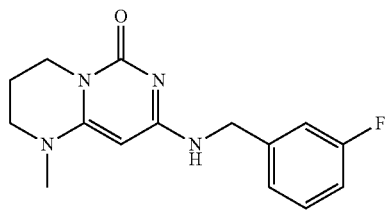 [SMILES: CN1CCCn2c1cc(NCc1cccc(F)c1)nc2=O]

The title compound or its salt was prepared by a procedure similar to that described for E59 starting from (3-fluorophenyl)methanamine and 8-chloro-1-methyl-3,4-dihydro-1H-pyrimido[1,6-a]pyrimidin-6(2H)-one.
LC-MS (ESI): m/z 289 [M+H]+; 0.918 min (ret time).

E70

1-Methyl-8-(thiophen-2-ylmethylsulfanyl)-1,2,3,4-tetrahydro-pyrimido[1,6-a]pyrimidin-6-one

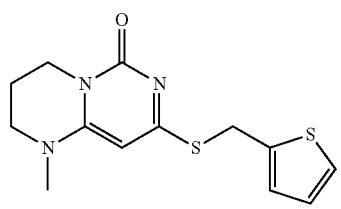 [SMILES: CN1CCCn2c1cc(SCc1cccs1)nc2=O]

The title compound or its salt was prepared by a procedure similar to that described for E62 starting from thiophen-2-ylmethanethiol and 8-chloro-1-methyl-3,4-dihydro-1H-pyrimido[1,6-a]pyrimidin-6(2H)-one.
LC-MS (ESI): m/z 294 [M+H]+; 0.86 min (ret time).

E71

8-(2,3-Difluoro-benzylamino)-1-methyl-1,2,3,4-tetrahydro-pyrimido[1,6-a]pyrimidin-6-one

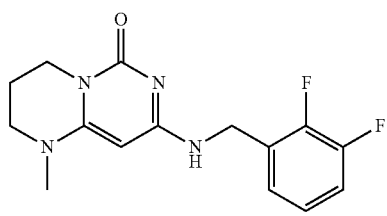 [SMILES: CN1CCCn2c1cc(NCc1cccc(F)c1F)nc2=O]

The title compound or its salt was prepared by a procedure similar to that described for E59 starting from (2,3-difluorophenyl)methanamine and 8-chloro-1-methyl-3,4-dihydro-1H-pyrimido[1,6-a]pyrimidin-6(2H)-one.
LC-MS (ESI): m/z 307 [M+H]+; 0.60 min (ret time).

E72

1-Methyl-8-(3,4,5-trifluoro-benzylamino)-1,2,3,4-tetrahydro-pyrimido[1,6-a]pyrimidin-6-one

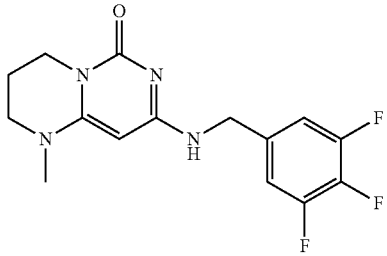 [SMILES: CN1CCCn2c1cc(NCc1cc(F)c(F)c(F)c1)nc2=O]

The title compound or its salt was prepared by a procedure similar to that described for E59 starting from (3,4,5-trifluorophenyl)methanamine and 8-chloro-1-methyl-3,4-dihydro-1H-pyrimido[1,6-a]pyrimidin-6(2H)-one.
LC-MS (ESI): m/z 325 [M+H]+; 0.73 min (ret time).

E73

1-methyl-8-(4-(3-(trifluoromethyl)phenoxy)phenethyl)-3,4-dihydro-1H-pyrimido[1,6-a]pyrimidin-6(2H)-one

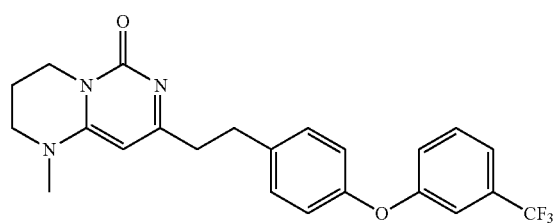 [SMILES: CN1CCCn2c1cc(CCc1ccc(Oc3cccc(C(F)(F)F)c3)cc1)nc2=O]

To a solution of 8-((4-(4-chloro-3-(trifluoromethyl)phenoxy)phenyl)ethynyl)-1-methyl-3,4-dihydro-1H-pyrimido[1,6-a]pyrimidin-6(2H)-one (20 mg, 0.043 mmol) in methanol (15 mL) was added palladium on carbon (6 mg, 0.107 mmol). The reaction mixture was purged with Ar for 10 mins at rt. The suspension was treated with a hydrogen gas balloon. After 1 h, the reaction mixture 5 was filtered and concentrated. The residue was purified by MDAP to afford the TFA salt of the title compound as a pale yellow oil (13 mg, 22.3%).
LC-MS (ESI): m/z 430 [M+H]+; 2.91 min (ret time)

E74

8-((3-fluoro-4-(4-fluorophenoxy)benzyl)oxy)-1-methyl-3,4-dihydro-1H-pyrimido[1,6-a]pyrimidin-6(2H)-one

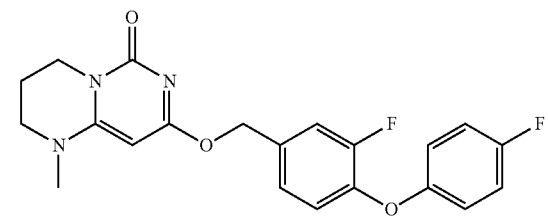 [SMILES: CN1CCCn2c1cc(OCc1ccc(Oc3ccc(F)cc3)c(F)c1)nc2=O]

The title compound or its salt was prepared by a procedure similar to that described for E2 starting from (3-fluoro-4-(4- fluorophenoxyl)phenyl)methanol and 8-chloro-1-methyl-3,
4-dihydro-1H-pyrimido[1,6-a]pyrimidin-6(2H)-one.
LC-MS (ESI): m/z 400 [M+H]⁺; 2.50 min (ret time)

E75

8-((3,5-difluoro-4-((6-(trifluoromethyl)pyridin-3-yl)
oxy)benzyl)oxy)-3,4-dihydro-1H-pyrimido[1,6-a]
pyrimidin-6(2H)-one

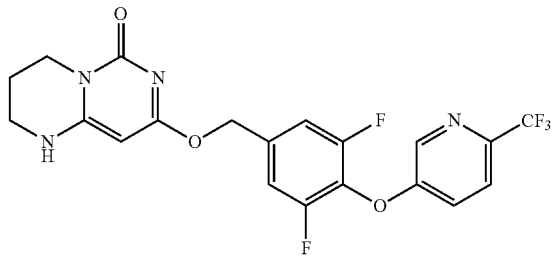 [SMILES: O=c1nc(OCc2cc(F)c(Oc3ccc(C(F)(F)F)nc3)c(F)c2)cc2n1CCCN2]

The title compound or its salt was prepared by using (3,5-difluoro-4-((6-(trifluoromethyl)pyridin-3-yl)oxy)phenyl)methanol and 2,4,6-trichloropyrimidine as starting materials in D54, followed by hydrolysis described in D55 and then cyclization described for E53.
LC-MS (ESI): m/z 455 [M+1]⁺; 2.60 (ret time).

E76

5-(((1-methyl-6-oxo-2,3,4,6-tetrahydro-1H-pyrimido
[1,6-a]pyrimidin-8-yl)oxy)methyl)-2-(pyridin-3-yloxy)benzonitrile

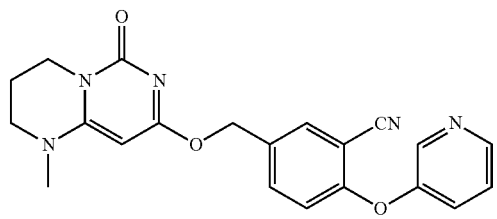 [SMILES: CN1CCCn2c1cc(OCc1ccc(Oc3cccnc3)c(C#N)c1)nc2=O]

The title compound or its salt was prepared by a procedure similar to that described for E2 starting from 5-(hydroxymethyl)-2-(pyridin-3-yloxy)benzonitrile and 8-chloro-1-methyl-3,4-dihydro-1H-pyrimido[1,6-a]pyrimidin-6(2H)-one.
LC-MS (ESI): m/z 390 [M+H]⁺; 1.70 min (ret time)

E77

1-methyl-8-((4-(3-(trifluoromethyl)phenoxy)benzyl)
oxy)-3,4-dihydro-1H-pyrimido[1,6-a]pyrimidin-6
(2H)-one

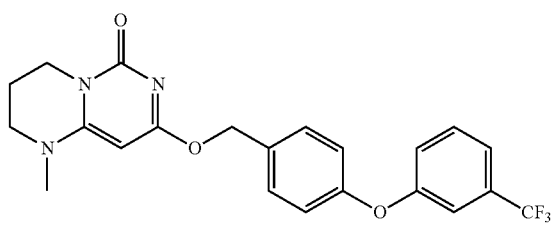

The title compound or its salt was prepared by a procedure similar to that described for E2 starting from (4-(3-(trifluoromethyl)phenoxy)phenyl)methanol and 8-chloro-1-methyl-3,4-dihydro-1H-pyrimido[1,6-a]pyrimidin-6(2H)-one.
LC-MS (ESI): m/z 432 [M+H]⁺; 2.81 min (ret time)

E78

8-((3,5-difluoro-4-(3-fluorophenoxy)benzyl)oxy)-1-methyl-3,4-dihydro-1H-pyrimido[1,6-a]pyrimidin-6
(2H)-one

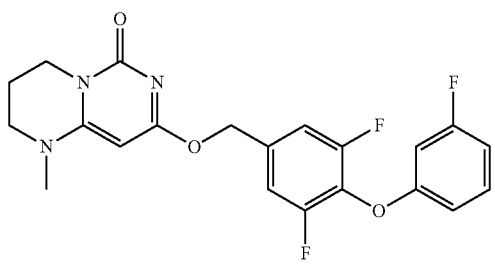 [SMILES: CN1CCCn2c1cc(OCc1cc(F)c(Oc3cccc(F)c3)c(F)c1)nc2=O]

The title compound or its salt was prepared by a procedure similar to that described for E2 starting from (3,5-difluoro-4-(3-fluorophenoxy)phenyl)methanol and 8-chloro-1-methyl-3,4-dihydro-1H-pyrimido[1,6-a]pyrimidin-6(2H)-one.
LC-MS (ESI): m/z 418 [M+1]⁺; 2.65 (ret time).

E79

8-((4-(3,5-difluorophenoxy)-3,5-difluorobenzyl)
oxy)-1-methyl-3,4-dihydro-1H-pyrimido[1,6-a]pyrimidin-6(2H)-one

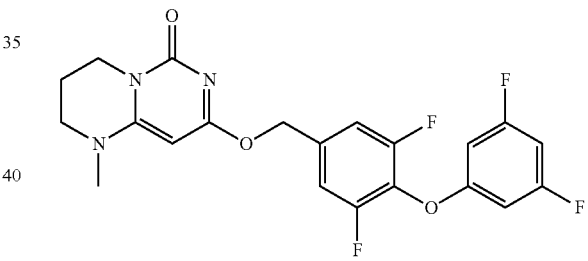

The title compound or its salt was prepared by a procedure similar to that described for E2 starting from (4-(3,5-difluorophenoxy)-3,5-difluorophenyl)methanol and 8-chloro-1-methyl-3,4-dihydro-1H-pyrimido[1,6-a]pyrimidin-6(2H)-one.
LC-MS (ESI): m/z 436 [M+1]⁺; 2.73 (ret time).

E80

2-(3-fluorophenoxy)-5-(((1-methyl-6-oxo-2,3,4,6-tetrahydro-1H-pyrimido[1,6-a]pyrimidin-8-yl)oxy)
methyl)benzonitrile

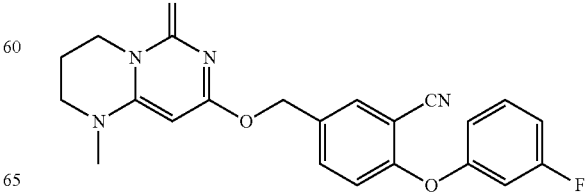

The title compound or its salt was prepared by a procedure similar to that described for E2 starting from 2-(3-fluorophenoxy)-5-(hydroxymethyl)benzonitrile and 8-chloro-1-methyl-3,4-dihydro-1H-pyrimido[1,6-a]pyrimidin-6(2H)-one.

LC-MS (ESI): m/z 407 [M+H]⁺; 2.46 min (ret time)

E81

8-((3,5-difluoro-4-(3-(trifluoromethyl)phenoxy)benzyl)oxy)-1-methyl-3,4-dihydro-1H-pyrimido[1,6-a]pyrimidin-6(2H)-one

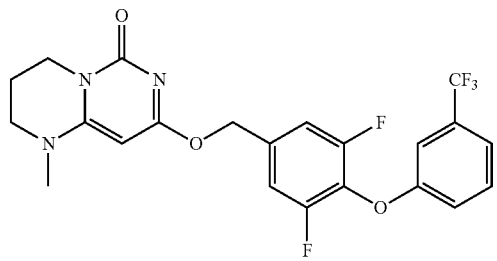 [SMILES: CN1CCCn2c1cc(OCc1cc(F)c(Oc3cccc(C(F)(F)F)c3)c(F)c1)nc2=O]

The title compound or its salt was prepared by a procedure similar to that described for E2 starting from (3,5-difluoro-4-(3-(trifluoromethyl)phenoxy)phenyl)methanol and 8-chloro-1-methyl-3,4-dihydro-1H-pyrimido[1,6-a]pyrimidin-6(2H)-one.

LC-MS (ESI): m/z 468 [M+1]⁺; 2.95 (ret time).

E82

8-((4-(4-chloro-3-fluorophenoxy)-3,5-difluorobenzyl)oxy)-1-methyl-3,4-dihydro-1H-pyrimido[1,6-a]pyrimidin-6(2H)-one

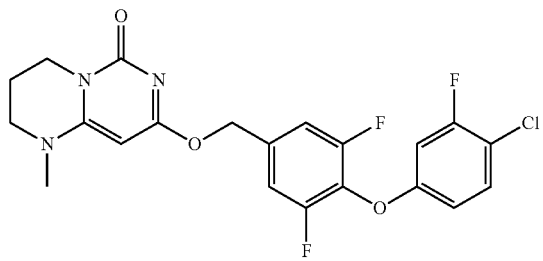 [SMILES: CN1CCCn2c1cc(OCc1cc(F)c(Oc3ccc(Cl)c(F)c3)c(F)c1)nc2=O]

The title compound or its salt was prepared by a procedure similar to that described for E2 starting from (4-(4-chloro-3-fluorophenoxy)-3,5-difluorophenyl)methanol and 8-chloro-1-methyl-3,4-dihydro-1H-pyrimido[1,6-a]pyrimidin-6(2H)-one.

LC-MS (ESI): m/z 452 [M+1]⁺; 2.92 (ret time).

E83

8-((4-(3-chloro-4-fluorophenoxy)-3,5-difluorobenzyl)oxy)-1-methyl-3,4-dihydro-1H-pyrimido[1,6-a]pyrimidin-6(2H)-one

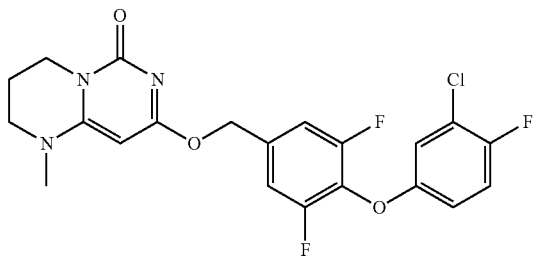 [SMILES: CN1CCCn2c1cc(OCc1cc(F)c(Oc3ccc(F)c(Cl)c3)c(F)c1)nc2=O]

The title compound or its salt was prepared by a procedure similar to that described for E2 starting from (4-(3-chloro-4-fluorophenoxy)-3,5-difluorophenyl)methanol and 8-chloro-1-methyl-3,4-dihydro-1H-pyrimido[1,6-a]pyrimidin-6(2H)-one.

LC-MS (ESI): m/z 452 [M+1]⁺; 2.88 (ret time).

E84

2-(3-chloro-4-fluorophenoxy)-5-(((1-methyl-6-oxo-2,3,4,6-tetrahydro-1H-pyrimido[1,6-a]pyrimidin-8-yl)oxy)methyl)benzonitrile

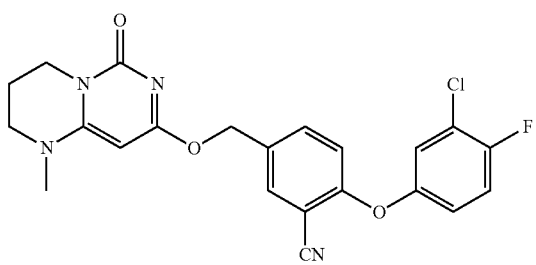

The title compound or its salt was prepared by a procedure similar to that described for E2 starting from 2-(3-chloro-4-fluorophenoxy)-5-(hydroxymethyl)benzonitrile and 8-chloro-1-methyl-3,4-dihydro-1H-pyrimido[1,6-a]pyrimidin-6(2H)-one.

LC-MS (ESI): m/z 441 [M+1]⁺; 2.69 (ret time).

E85

3-(2-fluoro-4-(((1-methyl-6-oxo-2,3,4,6-tetrahydro-1H-pyrimido[1,6-a]pyrimidin-8-yl)oxy)methyl)phenoxy)benzonitrile

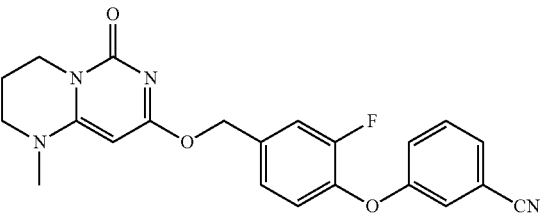 [SMILES: CN1CCCn2c1cc(OCc1ccc(Oc3cccc(C#N)c3)c(F)c1)nc2=O]

The title compound or its salt was prepared by a procedure similar to that described for E2 starting from 3-(2-fluoro-4-

(hydroxymethyl)phenoxy)benzonitrile and 8-chloro-1-methyl-3,4-dihydro-1H-pyrimido[1,6-a]pyrimidin-6(2H)-one.
LC-MS (ESI): m/z 407 [M+H]$^+$; 2.37 min (ret time)

E86

5-(((1-methyl-6-oxo-2,3,4,6-tetrahydro-1H-pyrimido[1,6-a]pyrimidin-8-yl)oxy)methyl)-2-(pyrimidin-5-yloxy)benzonitrile

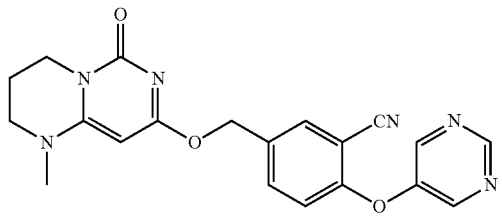 [SMILES: CN1CCCn2c1cc(OCc1ccc(Oc3cncnc3)c(C#N)c1)nc2=O]

The title compound or its salt was prepared by a procedure similar to that described for E2 starting from 5-(hydroxymethyl)-2-(pyrimidin-5-yloxy)benzonitrile and 8-chloro-1-methyl-3,4-dihydro-1H-pyrimido[1,6-a]pyrimidin-6(2H)-one.
LC-MS (ESI): m/z 391 [M+H]$^+$; 1.77 min (ret time).

E87

8-((3,5-difluoro-4-(4-fluorophenoxyl)benzyl)oxy)-1-methyl-3,4-dihydro-1H-pyrimido[1,6-a]pyrimidin-6(2H)-one

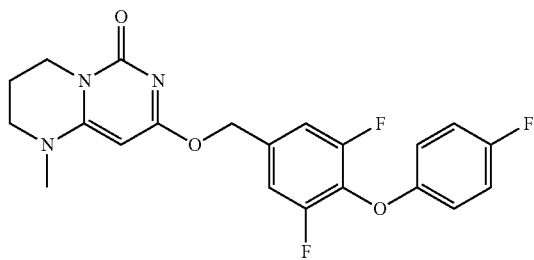 [SMILES: CN1CCCn2c1cc(OCc1cc(F)c(Oc3ccc(F)cc3)c(F)c1)nc2=O]

The title compound or its salt was prepared by a procedure similar to that described for E2 starting from (3,5-difluoro-4-(4-fluorophenoxy)phenyl)methanol and 8-chloro-1-methyl-3,4-dihydro-1H-pyrimido[1,6-a]pyrimidin-6(2H)-one.
LC-MS (ESI): m/z 418 [M+1]$^+$; 2.68 (ret time).

E88

8-((3,5-difluoro-4-(4-fluoro-3-(trifluoromethyl)phenoxy)benzyl)oxy)-1-methyl-3,4-dihydro-1H-pyrimido[1,6-a]pyrimidin-6(2H)-one

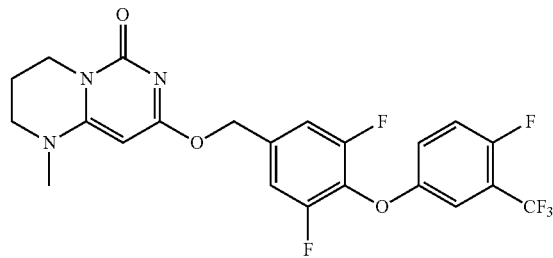 [SMILES: CN1CCCn2c1cc(OCc1cc(F)c(Oc3ccc(F)c(C(F)(F)F)c3)c(F)c1)nc2=O]

The title compound or its salt was prepared by a procedure similar to that described for E2 starting from (3,5-difluoro-4-(4-fluoro-3-(trifluoromethyl)phenoxy)phenyl)methanol and 8-chloro-1-methyl-3,4-dihydro-1H-pyrimido[1,6-a]pyrimidin-6(2H)-one.
LC-MS (ESI): m/z 486 [M+1]$^+$; 3.00 (ret time).

E89

8-((3,5-difluoro-4-(4-(trifluoromethyl)phenoxy)benzyl)oxy)-1-methyl-3,4-dihydro-1H-pyrimido[1,6-a]pyrimidin-6(2H)-one

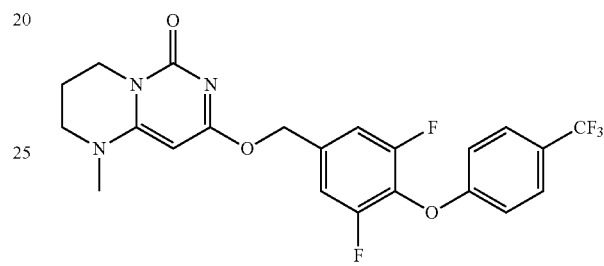

The title compound or its salt was prepared by a procedure similar to that described for E2 starting from (3,5-difluoro-4-(4-(trifluoromethyl)phenoxy)phenyl)methanol and 8-chloro-1-methyl-3,4-dihydro-1H-pyrimido[1,6-a]pyrimidin-6(2H)-one.
LC-MS (ESI): m/z 468 [M+1]$^+$; 2.98 (ret time).

E90

8-((4-(3-chlorophenoxy)-3,5-difluorobenzyl)oxy)-1-methyl-3,4-dihydro-1H-pyrimido[1,6-a]pyrimidin-6(2H)-one

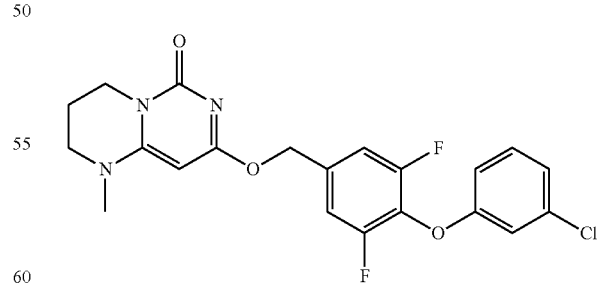

The title compound or its salt was prepared by a procedure similar to that described for E2 starting from (4-(3-chlorophenoxy)-3,5-difluorophenyl)methanol and 8-chloro-1-methyl-3,4-dihydro-1H-pyrimido[1,6-a]pyrimidin-6(2H)-one.
LC-MS (ESI): m/z 434 [M+1]$^+$; 2.88 (ret time).

E91

8-((4-(3,4-difluorophenoxy)-3,5-difluorobenzyl)oxy)-3,4-dihydro-1H-pyrimido[1,6-a]pyrimidin-6(2H)-one

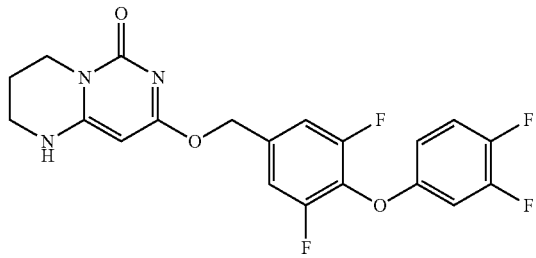 [SMILES: O=c1nc(OCc2cc(F)c(Oc3ccc(F)c(F)c3)c(F)c2)cc2n1CCCN2]

The title compound or its salt was prepared by using (4-(3,4-difluorophenoxy)-3,5-difluorophenyl)methanol and 2,4,6-trichloropyrimidine as starting materials in D54, followed by hydrolysis described in D55 and then cyclization described for E53.

LC-MS (ESI): m/z 422 [M+H]$^+$; 2.59 min (ret time).

E92

5-((((6-oxo-2,3,4,6-tetrahydro-1H-pyrimido[1,6-a]pyrimidin-8-yl)oxy)methyl)-2-((5-(trifluoromethyl)pyridin-2-yl)oxy)benzonitrile

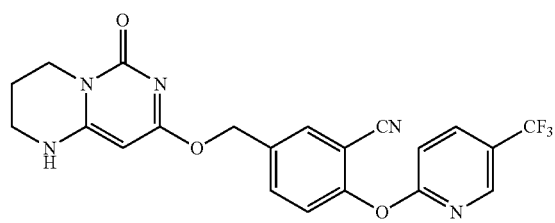 [SMILES: N#Cc1cc(COc2cc3n(c(=O)n2)CCCN3)ccc1Oc1ccc(C(F)(F)F)cn1]

The title compound or its salt was prepared by using 5-(hydroxymethyl)-2-((5-(trifluoromethyl)pyridin-2-yl)oxy)benzonitrile and 2,4,6-trichloropyrimidine as starting materials in D54, followed by hydrolysis described in D55 and then cyclization described for E53.

LC-MS (ESI): m/z 444 [M+H]$^+$; 2.47 min (ret time).

E93

8-((3,5-difluoro-4-(4-fluoro-3-(trifluoromethyl)phenoxy)benzyl)oxy)-3,4-dihydro-1H-pyrimido[1,6-a]pyrimidin-6(2H)-one

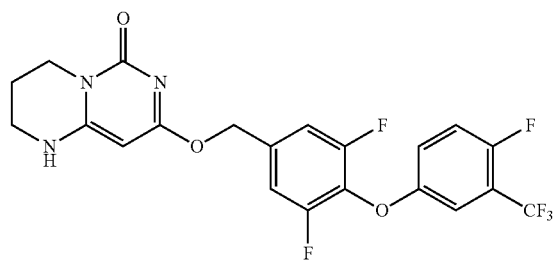 [SMILES: O=c1nc(OCc2cc(F)c(Oc3ccc(F)c(C(F)(F)F)c3)c(F)c2)cc2n1CCCN2]

The title compound or its salt was prepared by using (3,5-difluoro-4-(3-fluoro-4-(trifluoromethyl)phenoxy)phenyl) methanol and 2,4,6-trichloropyrimidine as starting materials in D54, followed by hydrolysis described in D55 and then cyclization described for E53.

LC-MS (ESI): m/z 472 [M+H]$^+$; 2.80 min (ret time).

E94

2-(3,4-difluorophenoxy)-5-((((6-oxo-2,3,4,6-tetrahydro-1H-pyrimido[1,6-a]pyrimidin-8-yl)oxy)methyl)benzonitrile

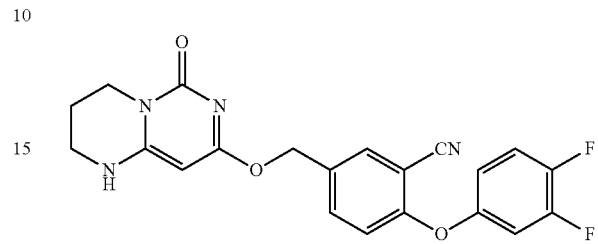

The title compound or its salt was prepared by using 2-(3,4-difluorophenoxy)-5-(hydroxymethyl)benzonitrile and 2,4,6-trichloropyrimidine as starting materials in D54, followed by hydrolysis described in D55 and then cyclization described for E53.

LC-MS (ESI): m/z 411 [M+H]$^+$; 2.38 min (ret time).

E95

8-((4-((6-chloropyridin-3-yl)oxy)-3-fluorobenzyl)oxy)-1-methyl-3,4-dihydro-1H-pyrimido[1,6-a]pyrimidin-6(2H)-one

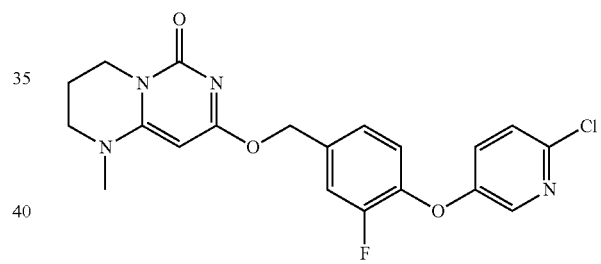

The title compound or its salt was prepared by a procedure similar to that described for E2 starting from (4-((6-chloropyridin-3-yl)oxy)-3-fluorophenyl)methanol and 8-chloro-1-methyl-3,4-dihydro-1H-pyrimido[1,6-a]pyrimidin-6(2H)-one.

LC-MS (ESI): m/z 417 [M+1]$^+$; 2.38 (ret time).

E96

2-(4-chloro-3-fluorophenoxy)-5-(((1-methyl-6-oxo-2,3,4,6-tetrahydro-1H-pyrimido[1,6-a]pyrimidin-8-yl)oxy)methyl)benzonitrile

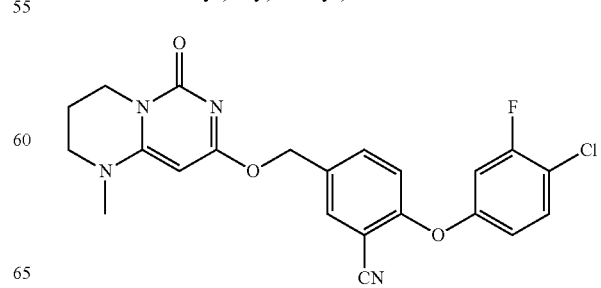

similar to that described for E2 starting from 2-(4-chloro-3-fluorophenoxy)-5-(hydroxymethyl)benzonitrile and 8-chloro-1-methyl-3,4-dihydro-1H-pyrimido[1,6-a]pyrimidin-6(2H)-one.

LC-MS (ESI): m/z 441 [M+1]$^+$; 2.71 (ret time).

E97

8-((4-(4-chloro-3-(trifluoromethyl)phenoxy)-3-fluorobenzyl)oxy)-3,4-dihydro-1H-pyrimido[1,6-a]pyrimidin-6(2H)-one

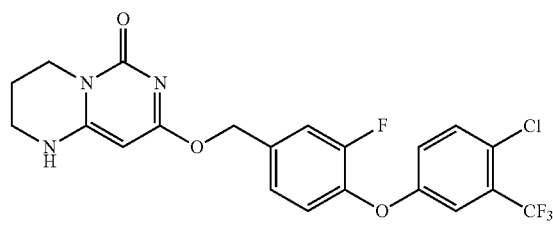 [SMILES: O=c1nc(OCc2ccc(Oc3ccc(Cl)c(C(F)(F)F)c3)c(F)c2)cc2n1CCCN2]

The title compound or its salt was prepared by a procedure similar to that described for E53 starting from [4-(4-chloro-3-trifluoromethyl-phenoxy)-3-fluoro-phenyl]-methanol and 2,4,6 trichloropyrimidine.

LC-MS (ESI): m/z 470 [M+H]$^+$; 2.98 min (ret time).

E98

3-fluoro-5-(2-fluoro-4-(((1-methyl-6-oxo-2,3,4,6-tetrahydro-1H-pyrimido[1,6-a]pyrimidin-8-yl)oxy)methyl)phenoxy)benzonitrile

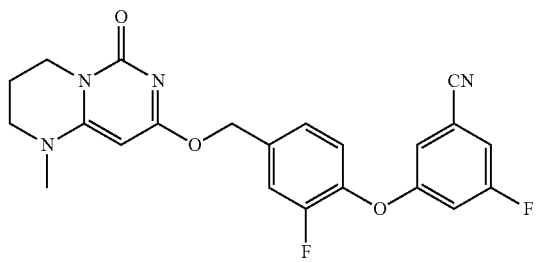 [SMILES: CN1CCCn2c1cc(OCc1ccc(Oc3cc(F)cc(C#N)c3)c(F)c1)nc2=O]

The title compound or its salt was prepared by a procedure similar to that described for E2 starting from 3-fluoro-5-(2-fluoro-4-(hydroxymethyl)phenoxy)benzonitrile and 8-chloro-1-methyl-3,4-dihydro-1H-pyrimido[1,6-a]pyrimidin-6(2H)-one.

LC-MS (ESI): m/z 425 [M+1]$^+$; 2.59 (ret time).

E99

8-((3,4-difluorobenzyl)oxy)-3,4-dihydro-1H-pyrimido[1,6-a]pyrimidin-6(2H)-one

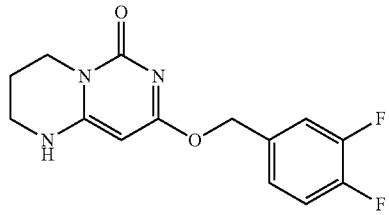 [SMILES: O=c1nc(OCc2ccc(F)c(F)c2)cc2n1CCCN2]

The title compound or its salt was prepared by using (3,4-difluorophenyl)methanol and 2,4,6-trichloropyrimidine as starting materials in D54, followed by hydrolysis described in D55 and then cyclization described for E53.

LC-MS (ESI): m/z 294 [M+1]$^+$; 1.86 (ret time).

E100

8-((4-(4-fluoro-3-(trifluoromethyl)phenoxy)benzyl)oxy)-3,4-dihydro-1H-pyrimido[1,6-a]pyrimidin-6(2H)-one

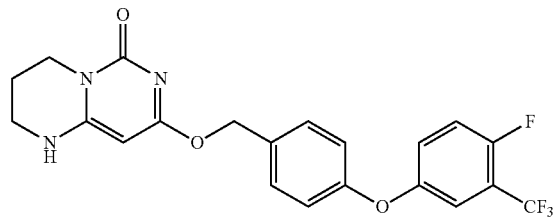 [SMILES: O=c1nc(OCc2ccc(Oc3ccc(F)c(C(F)(F)F)c3)cc2)cc2n1CCCN2]

The title compound or its salt was prepared by using (4-(4-fluoro-3-(trifluoromethyl)phenoxy)phenyl)methanol and 2,4,6-trichloropyrimidine as starting materials in D54, followed by hydrolysis described in D55 and then cyclization described for E53.

LC-MS (ESI): m/z 436 [M+H]+; 2.83 min (ret time).

E101

8-((3-fluoro-4-(3-(trifluoromethyl)phenoxy)benzyl)oxy)-3,4-dihydro-1H-pyrimido[1,6-a]pyrimidin-6(2H)-one

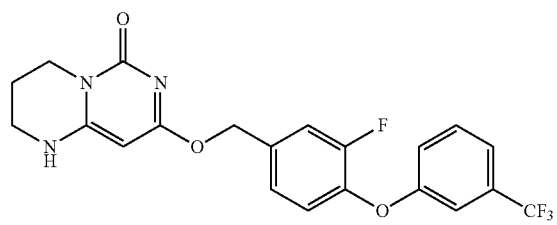

The title compound or its salt was prepared by using (3-fluoro-4-(3-(trifluoromethyl)phenoxy)phenyl)methanol and 2,4,6-trichloropyrimidine as starting materials in D54, followed by hydrolysis described in D55 and then cyclization described for E53.

LC-MS (ESI): m/z 436 [M+H]+; 2.76 min (ret time).

E102

8-(4-(4-chloro-3-fluorophenoxy)-3-fluorophenethoxy)-1-methyl-3,4-dihydro-1H-pyrimido[1,6-a]pyrimidin-6(2H)-one

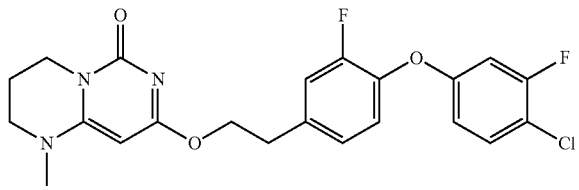 [SMILES: CN1CCCn2c1cc(OCCc1ccc(Oc3ccc(Cl)c(F)c3)c(F)c1)nc2=O]

The title compound or its salt was prepared by a procedure similar to that described for E2 starting from 2-(4-(4-chloro-3-fluorophenoxy)-3-fluorophenyl)ethanol and 8-chloro-1-methyl-3,4-dihydro-1H-pyrimido[1,6-a]pyrimidin-6(2H)-one.

LC-MS (ESI): m/z 448 [M+1]$^+$; 2.88 (ret time).

E103

8-(4-(4-chloro-3-fluorophenoxy)phenethoxy)-1-methyl-3,4-dihydro-1H-pyrimido[1,6-a]pyrimidin-6(2H)-one

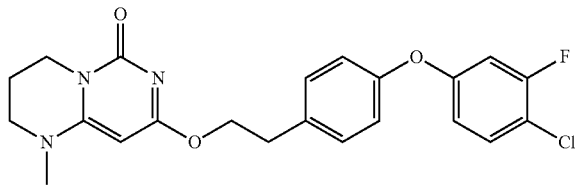 [SMILES: CN1CCCn2c1cc(OCCc1ccc(Oc3ccc(Cl)c(F)c3)cc1)nc2=O]

The title compound or its salt was prepared by a procedure similar to that described for E2 starting from 2-(4-(3-chloro-4-fluorophenoxy)phenyl)ethanol and 8-chloro-1-methyl-3,4-dihydro-1H-pyrimido[1,6-a]pyrimidin-6(2H)-one.

LC-MS (ESI): m/z 430 [M+1]$^+$; 2.82 (ret time).

E104

4-(2-cyano-4-(((6-oxo-2,3,4,6-tetrahydro-1H-pyrimido[1,6-a]pyrimidin-8-yl)oxy)methyl)phenoxy)-2-fluorobenzonitrile

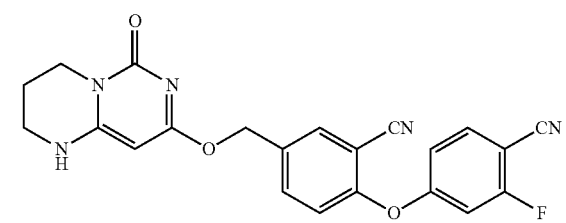 [SMILES: N#Cc1ccc(Oc2ccc(COc3cc4n(c(=O)n3)CCCN4)cc2C#N)cc1F]

The title compound or its salt was prepared by using 4-(2-cyano-4-(hydroxymethyl)phenoxy)-2-fluorobenzonitrile and 2,4,6-trichloropyrimidine as starting materials in D54, followed by hydrolysis described in D55 and then cyclization described for E53.

LC-MS (ESI): m/z 410 [M+H]$^+$; 2.23 min (ret time).

E105

8-(3-fluoro-4-(3-(trifluoromethyl)phenoxy)phenethoxy)-1-methyl-3,4-dihydro-1H-pyrimido[1,6-a]pyrimidin-6(2H)-one

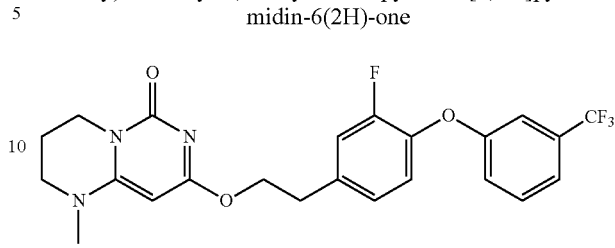

The title compound or its salt was prepared by a procedure similar to that described for E2 starting from 2-(3-fluoro-4-(3-(trifluoromethyl)phenoxy)phenyl)ethanol and 8-chloro-1-methyl-3,4-dihydro-1H-pyrimido[1,6-a]pyrimidin-6(2H)-one.

LC-MS (ESI): m/z 464 [M+1]$^+$; 2.93 (ret time).

E106

2-chloro-4-(2-cyano-4-(((6-oxo-2,3,4,6-tetrahydro-1H-pyrimido[1,6-a]pyrimidin-8-yl)oxy)methyl)phenoxy)benzonitrile

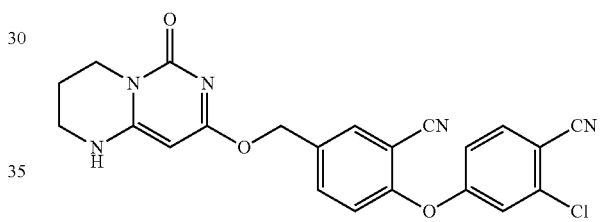

The title compound or its salt was prepared by using 2-chloro-4-(2-cyano-4-(hydroxymethyl)phenoxy)benzonitrile and 2,4,6-trichloropyrimidine as starting materials in D54, followed by hydrolysis described in D55 and then cyclization described for E53.

LC-MS (ESI): m/z 434 [M+H]$^+$; 2.36 min (ret time).

E107

2-(4-chloro-3-(trifluoromethyl)phenoxy)-5-(((6-oxo-2,3,4,6-tetrahydro-1H-pyrimido[1,6-a]pyrimidin-8-yl)oxy)methyl)benzonitrile

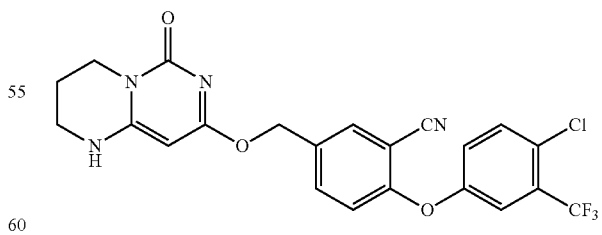

The title compound or its salt was prepared by using 2-(4-chloro-3-(trifluoromethyl)phenoxy)-5-(hydroxymethyl)benzonitrile and 2,4,6-trichloropyrimidine as starting materials in D54, followed by hydrolysis described in D55 and then cyclization described for E53.

LC-MS (ESI): m/z 477 [M+H]$^+$; 2.78 min (ret time).

E108

8-((4-(3-fluoro-4-methylphenoxy)benzyl)oxy)-3,4-dihydro-1H-pyrimido[1,6-a]pyrimidin-6(2H)-one

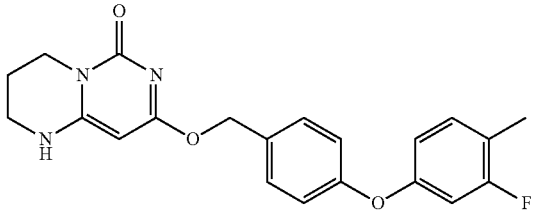 [SMILES: Cc1ccc(Oc2ccc(COc3cc4n(c(=O)n3)CCCN4)cc2)cc1F]

The title compound or its salt was prepared by a procedure similar to that described for E53 starting from (4-(3-fluoro-4-methylphenoxy)phenyl)methanol and 2,4,6 trichloropyrimidine. The title compound or its salt was prepared by using (4-(3-fluoro-4-methylphenoxy)phenyl)methanol and 2,4,6-trichloropyrimidine as starting materials in D54, followed by hydrolysis described in D55 and then cyclization described for E53.

LC-MS (ESI): m/z 382 [M+1]$^+$; 2.70 (ret time).

E109

8-(2-(5-(3,4-difluorophenoxy)-4-fluoropyridin-2-yl)ethoxy)-1-methyl-3,4-dihydro-1H-pyrimido[1,6-a]pyrimidin-6(2H)-one

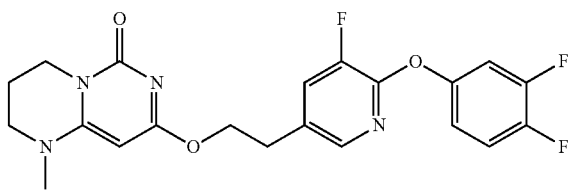 [SMILES: CN1CCCn2c1cc(OCCc1cnc(Oc3ccc(F)c(F)c3)c(F)c1)nc2=O]

The title compound or its salt was prepared by a procedure similar to that described for E2 starting from 2-(6-(3,4-difluorophenoxy)-5-fluoropyridin-3-yl)ethanol and 8-chloro-1-methyl-3,4-dihydro-1H-pyrimido[1,6-a]pyrimidin-6(2H)-one.

LC-MS (ESI): m/z 433 [M+H]$^+$; 2.59 min (ret time)

E110

8-(4-(3,4-difluorophenoxy)phenethoxy)-1-methyl-3,4-dihydro-1H-pyrimido[1,6-a]pyrimidin-6(2H)-one

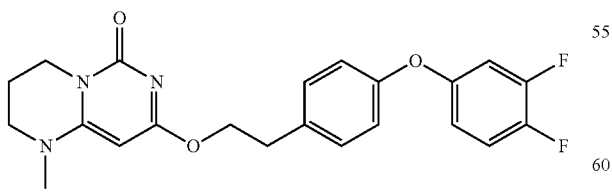

The title compound or its salt was prepared by a procedure similar to that described for E2 starting from 2-(4-(3,4-difluorophenoxy)phenyl)ethanol and 8-chloro-1-methyl-3,4-dihydro-1H-pyrimido[1,6-a]pyrimidin-6(2H)-one.

LC-MS (ESI): m/z 414 [M+H]$^+$; 2.68 min (ret time).

E111

8-(3,4-difluorophenethoxy)-3,4-dihydro-1H-pyrimido[1,6-a]pyrimidin-6(2H)-one

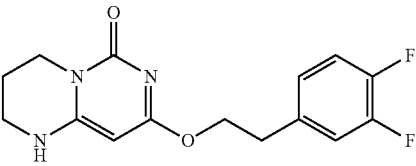 [SMILES: O=c1nc(OCCc2ccc(F)c(F)c2)cc2n1CCCN2]

To a solution of 2-(3,4-difluorophenyl)ethanol (221 mg, 1.400 mmol) in THF (5 mL) was added NaH (112 mg, 2.80 mmol) at 0° C. The reaction mixture was stirred for 10 min at 0° C., and then tert-butyl 8-chloro-6-oxo-2,3,4,6-tetrahydro-1H-pyrimido[1,6-a]pyrimidine-1-carboxylate (400 mg, 1.400 mmol) was added and stirred for another 0.5 hr at 0° C. The mixture was poured into ice water and extracted with DCM (10 mL×3). The combined extracts were washed with water (10 mL) then brine (10 mL) and then dried over Na$_2$SO$_4$. The mixture was concentrated to give tert-butyl 8-(3,4-difluorophenethoxy)-6-oxo-2,3,4,6-tetrahydro-1H-pyrimido[1,6-a]pyrimidine-1-carboxylate. A solution of the crude compound in 1,4-dioxane (10 mL) was added 4N HCl, stirred for 3 h at rt, and then concentrated. The residue was purified by MDAP to afford the HCl salt of the title product as a white solid (46 mg, 10.8% yield).

LC-MS (ESI): m/z 308 [M+H]$^+$; 0.94 min (ret time).

E112

8-(3,4-dichlorophenethoxy)-3,4-dihydro-1H-pyrimido[1,6-a]pyrimidin-6(2H)-one

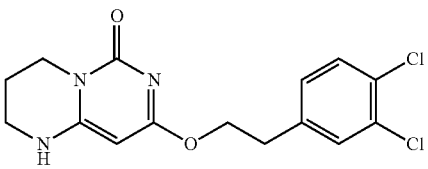 [SMILES: O=c1nc(OCCc2ccc(Cl)c(Cl)c2)cc2n1CCCN2]

The title compound or its salt was prepared by a procedure similar to that described for E111 starting from 2-(3,4-dichlorophenyl)ethanol and tert-butyl 8-chloro-6-oxo-2,3,4,6-tetrahydro-1H-pyrimido[1,6-a]pyrimidine-1-carboxylate.

LC-MS (ESI): m/z 340 [M+H]$^+$; 1.04 min (ret time).

E113

8-(3,4,5-trifluorobenzyloxy)-3,4-dihydro-1H-pyrimido[1,6-a]pyrimidin-6(2H)-one

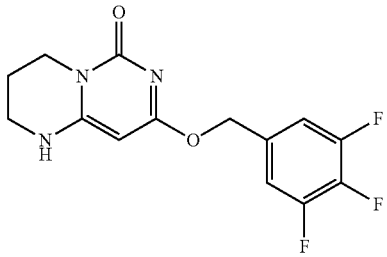 [SMILES: O=c1nc(OCc2cc(F)c(F)c(F)c2)cc2n1CCCN2]

The title compound and/or its salt was prepared by a procedure similar to that described for E111 starting from (3,4,5-trifluorophenyl)methanol and tert-butyl 8-chloro-6-oxo-2,3,4,6-tetrahydro-1H-pyrimido[1,6-a]pyrimidine-1-carboxylate.

LC-MS (ESI): m/z 312 [M+H]$^+$; 0.51 min (ret time).

E114

8-((3,5-difluoro-4-(4-fluorophenoxyl)benzyl)oxy)-3,4-dihydro-1H-pyrimido[1,6-a]pyrimidin-6(2H)-one

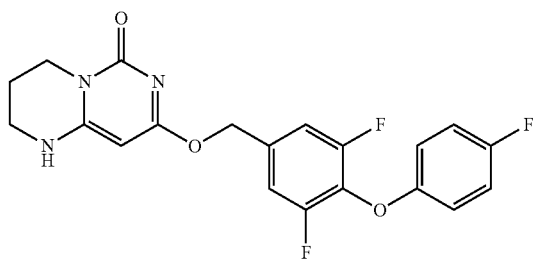 [SMILES: O=c1nc(OCc2cc(F)c(Oc3ccc(F)cc3)c(F)c2)cc2n1CCCN2]

The title compound or its salt was prepared by a procedure similar to that described for E111 starting from (3,5-difluoro-4-(4-fluorophenoxyl)phenyl)methanol and tert-butyl 8-chloro-6-oxo-2,3,4,6-tetrahydro-1H-pyrimido[1,6-a]pyrimidine-1-carboxylate.

LC-MS (ESI): m/z 404 [M+H]$^+$; 0.94 min (ret time).

E115

8-((3,5-difluoro-4-(3-fluorophenoxyl)benzyl)oxy)-3,4-dihydro-1H-pyrimido[1,6-a]pyrimidin-6(2H)-one

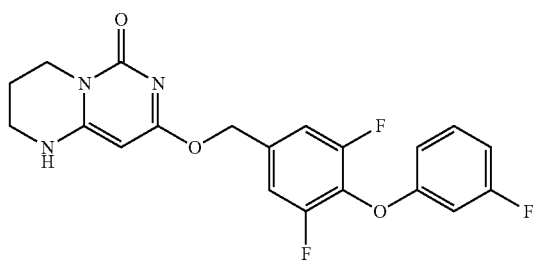 [SMILES: O=c1nc(OCc2cc(F)c(Oc3cccc(F)c3)c(F)c2)cc2n1CCCN2]

The title compound or its salt was prepared by a procedure similar to that described for E111 starting from (3,5-difluoro-4-(3-fluorophenoxyl)phenyl)methanol and tert-butyl 8-chloro-6-oxo-2,3,4,6-tetrahydro-1H-pyrimido[1,6-a]pyrimidine-1-carboxylate.

LC-MS (ESI): m/z 404 [M+H]$^+$; 0.93 min (ret time).

E116

8-((3-fluoro-4-(3-fluorophenoxyl)benzyl)oxy)-3,4-dihydro-1H-pyrimido[1,6-a]pyrimidin-6(2H)-one

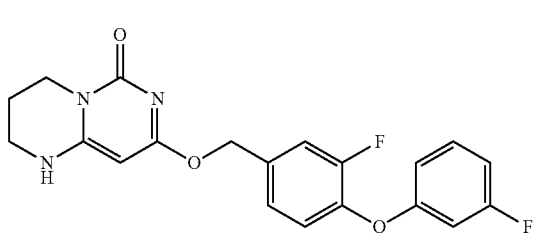

The title compound or its salt was prepared by a procedure similar to that described for E111 starting from (3-fluoro-4-(3-fluorophenoxyl)phenyl)methanol and tert-butyl 8-chloro-6-oxo-2,3,4,6-tetrahydro-1H-pyrimido[1,6-a]pyrimidine-1-carboxylate.

LC-MS (ESI): m/z 386 [M+H]$^+$; 0.90 min (ret time).

E117

8-((4-(3,4-difluorophenoxy)-3-fluorobenzyl)oxy)-3,4-dihydro-1H-pyrimido[1,6-a]pyrimidin-6(2H)-one

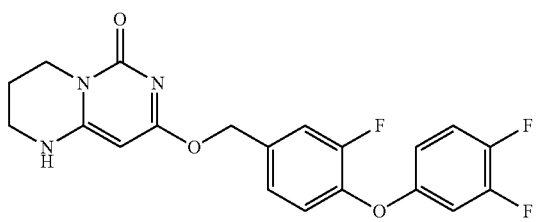

The title compound or its salt was prepared by a procedure similar to that described for E111 starting from (4-(3,4-difluorophenoxy)-3-fluorophenyl)methanol and tert-butyl 8-chloro-6-oxo-2,3,4,6-tetrahydro-1H-pyrimido[1,6-a]pyrimidine-1-carboxylate.

LC-MS (ESI): m/z 404 [M+H]$^+$; 0.94 min (ret time).

E118

8-((3-fluoro-4-(4-fluorophenoxyl)benzyl)oxy)-3,4-dihydro-1H-pyrimido[1,6-a]pyrimidin-6(2H)-one

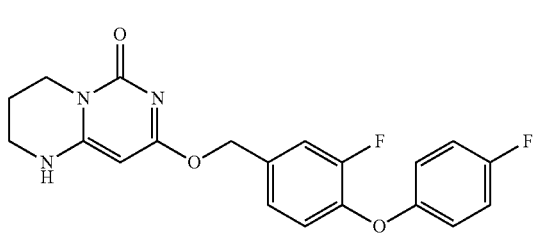 [SMILES: O=c1nc(OCc2ccc(Oc3ccc(F)cc3)c(F)c2)cc2n1CCCN2]

The title compound or its salt was prepared by a procedure similar to that described for E111 starting from (3-fluoro-4-

(4-fluorophenoxyl)phenyl)methanol and tert-butyl 8-chloro-6-oxo-2,3,4,6-tetrahydro-1H-pyrimido[1,6-a]pyrimidine-1-carboxylate.

LC-MS (ESI): m/z 386 [M+H]$^+$; 0.92 min (ret time).

E119

8-((4-(3,4-difluorophenoxy)benzyl)oxy)-3,4-dihydro-1H-pyrimido[1,6-a]pyrimidin-6(2H)-one

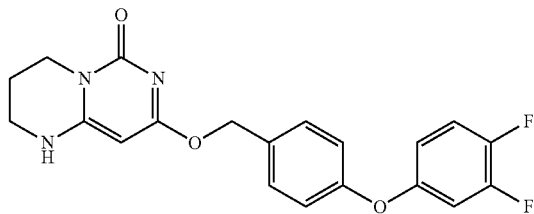

The title compound or its salt was prepared by a procedure similar to that described for E111 starting from (4-(3,4-difluorophenoxy)phenyl)methanol and tert-butyl 8-chloro-6-oxo-2,3,4,6-tetrahydro-1H-pyrimido[1,6-a]pyrimidine-1-carboxylate.

LC-MS (ESI): m/z 386 [M+H]$^+$; 0.93 min (ret time).

D. BIOLOGICAL ASSAYS AND DATA

The compounds of present invention are Lp-PLA$_2$ inhibitors, and are useful in the treatment of diseases mediated by Lp-PLA$_2$. The biological activities of the compounds of present invention can be determined by using any suitable assay for determining the activity of a compound as a Lp-PLA$_2$ inhibitor, as well as tissue and in vivo models.

The biological activity data for each compound was either reported in at least one experiment or the average of multiple experiments. It is understood that the data described herein may have reasonable variations depending on the specific conditions and procedures used by the person conducting the experiments.

Lipoprotein-Associated Phospholipase A2 (Lp-PLA$_2$) Biochemical Assay (1) Recombinant Human Lp-PLA$_2$ Assay (rhLp-PLA$_2$) (Also Referred to as "PED6" Assay)

N-((6-(2,4-dinitrophenyl)amino)-hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6) is a commercially available fluorescently-labeled phospholipid, which is commercially available from Invitrogene and Molecular Probes. There is a quenching para-nitro phenyl (PNP) group in the sn3 position and a Bodipy fluorescein (FL) group in the sn2 position. Upon cleavage with Lp-PLA$_2$, the Bodipy FL group is liberated and then may result in an increase in fluorescence Inhibitors of Lp-PLA$_2$ therefore prevent this cleavage and no fluorescent increase is observed.

The PED6 assay was run as an unquenched 10 µL assay. The source plate containing the compounds to be tested was prepared by making 1:3 (by volume) serial dilution of the compounds within DMSO on 384-well microplate. Then, 0.01 µL of the compounds on compound source plate were transferred into 384 well Greiner 784076 (black) plates using ECHO liquid dispenser. 5 µL of recombinant human Lp-PLA$_2$ enzyme (4 nM (or 110 pM) rhLp-PLA$_2$ in assay buffer of 50 mM HEPES, pH 7.4, 150 mM NaCl, 1 mM CHAPS) was added to each well of the plate. Plates were centrifuged for 10 sec at 500 rpm. After 30 minutes preincubation, 5 µL of substrate (4 µM (or 5 µM) PED6 [from 5 mM DMSO stock] in assay buffer of 50 mM HEPES, pH 7.4, 150 mM NaCl, 1 mM CHAPS) was added to 384 well Greiner 784076 (black) plates. Plates were centrifuged for 10 sec at 500 rpm. The plate was covered to protect it from light and incubated for 20 min at room temperature. The plates were read for fluorescence intensity at ex: 480/em: 540 using ViewLux microplate imager for Envision spectrofluroimeters pIC50 data, curve and QC analysis was conducted by using XL fit module in Excel.

All exemplified compounds of the present invention were tested according to the above assays or similar assay as described above and were found to demonstrate inhibition activity to Lp-PLA$_2$. The compounds described below were tested generally according to the PED6 assay described above. The pIC$_{50}$ value for each compound was either reported in at least one experiment or the average of multiple experiments. The upper limit for pIC$_{50}$ obtained in this PED6 assay is 9.3. If a refined assay is used, compounds that exhibit pIC$_{50}$ equal to 9.3 in the PED6 assay described above may demonstrate pIC$_{50}$ higher than 9.3.

The pIC$_{50}$ values in the PED6 assay for compounds of all examples were at least 5.0.

The pIC$_{50}$ values in the PED6 assay for examples 1-7, 10, 13-17, 21, 25, 28-30, 32, 34, 38, 40, 42, 53-56, 58, 74-85, 87-108, 110, and 113-119 were at least 8.0.

The pIC$_{50}$ values in the PED6 assay for examples 3, 7, 53, 55, 56, 58, 75, 79, 80-84, 88, 90, 91, 93-98, 100-102, 104, 105, 107, and 114-119 were at least 9.0.

Table 1 below provides the pIC50 for some exemplified compounds.

| Example No. | rhLp-PLA$_2$ (PED6 assay) (pIC50) |
|---|---|
| 2 | 8.6 |
| 3 | 9.0 |
| 7 | 9.1 |
| 21 | 8.7 |
| 28 | 8.6 |
| 40 | 8.0 |
| 42 | 8.3 |
| 53 | 9.0 |
| 58 | >9.3 |
| 75 | >9.3 |
| 76 | 8.9 |
| 79 | 9.1 |
| 83 | >9.3 |
| 93 | 9.3 |

(2) PLA2 VIIB Assay

PLA2 VIIB (also known as Novel Serine Dependent Lipase, NSDL) is a serine hydrolase with 40% amino acid identity with human Lp-PLA$_2$. Sequence comparisons indicate that the PLA VIIB active site catalytic triad positions are similar to those of Lp-PLA$_2$. Similar to Lp-PLA$_2$, it is capable of hydrolyzing oxidatively modified phospholipids and may be assayed using known Lp-PLA$_2$ substrates.

Upon cleavage by a phopholipase, PLA2 VIIB liberates a fluorescent Bodipy group. Recombinant human PLA2 VIIB is used as the phospholipase source in this assay, and compounds are screened to test their degree of inhibition in this assay. The assay is used to determine the degree of selectivity of the testing compounds between PLA2 VIIB and Lp-PLA$_2$.

The PLA2 VIIB assay was applied as an unquenched 10 µL assay. The source plate containing the compounds is prepared by making 1:3 (by volume) serial dilution of the compounds with pure DMSO on 384-well microplate. 0.01 µL of compounds on the compound source plate were transferred into 384 well Greiner 784076 (black) plates-by ECHO liquid dispenser. 5 µL of Novel Serine Dependent Lipase (NSDL) enzyme (5 nM NSDL in assay buffer of 50 mM HEPES, pH 7.4, 150 mM NaCl, 1 mM CHAPS) was added to each well. Plates were centrifuged for 10 sec at 500 rpm. After 30 minutes preincubation, 5 µL of substrate (5 µM PED6 [from 5 mM DMSO stock] in assay buffer of 50 mM HEPES, pH 7.4, 150 mM NaCl, 1 mM CHAPS) was added to 384 well Greiner 784076 (black) low-volume plates. Plates were kinetic read by starting read immediately after PED6 addition at ex: 480/em: 540 using ViewLux microplate reader or Envision spectrofluorimeters. IC 50 data (which may be converted to pIC50 data), curve and QC analysis was conducted using XLfit module in Excel.

All exemplified compounds of the present invention were tested in PLA2 VIIB assay or similar assay as described above. All tested compounds except Examples 9, 11, 18-19, 22-24, 28, 36, 39, 43-52, 59-65, 67-73, 109 and 111 had over 100 fold selectivity between human recombinant Lp-PLA$_2$ and PLA2 VIIB.

(3) Lipoprotein-Associated Phospholipase A2 (Lp-PLA$_2$) Human Plasma Assay (Also Referred to as "Thio-PAF Assay")

The human plasma assay utilizes a thioester analog of PAF (phosphatidylcholine), where hydrolysis yields to the formation of a phospholipid containing a free thiol group. The amount of thiol is quantitated continuously by reacting with CPM (7-diethylamino-3-(4'-maleimidylphenyl)-4-methylcoumarin), a maleimide which increases in fluoresence after Michael addition of thiols. This assay may detect the activity of Lp-PLA$_2$ in human plasma, as determined by specific inhibition by Lp-PLA$_2$ inhibitors.

The thio-PAF assay was run as a quenched 15 µL assay. Compounds source plate was prepared by making 1:3 (by volume) serial dilution of the compounds into pure DMSO on 384-well microplate. 0.01 µL of compounds on compound source plate were transferred to 384 well Greiner 784076 (black) low-volume plates by ECHO liquid dispenser. 8 µL pooled human plasma, which was previously aliquoted and frozen, was added. Plates were centrifuged for 10 sec at 500 rpm. After 30 minutes preincubation, 2 µL of substrate solution comprising 2.5 mM 2-thio-PAF [from ethanol stock], 32 µM CPM [from a DMSO stock] and 3.2 mM NEM (N-ethylmaleimide) [made fresh daily in DMSO] in assay buffer of 50 mM HEPES, pH 7.4, 150 mM NaCl, 1 mM CHAPS was added to 384 well Greiner 784076 (black) low-volume plates by BRAVO liquid handling station. After 2 mins, reaction was quenched with 5 µL of 5% aqueous trifluoroacetic acid (TFA). Plates were covered to protect from light and incubated for 40 min at room temperature. Plates were read at ex: 380/em: 485 using-Envision microplate reader. pIC50 data, curve and QC analysis was conducted by using XLFit module in Excel.

All exemplified compounds of the present invention were tested in thio-PAF assay or similar assay as described above.

The pIC$_{50}$ values in the thio-PAF assay for all compounds except examples 18, 19, 22-24, 39, 43, 45-50, 52, 57, 59-65, 67-73 were at least 5.0.

The pIC$_{50}$ values in the thio-PAF assay for examples 1-10, 12, 13, 15-17, 20, 21, 25, 27-34, 37, 38, 40, 42, 53-56, 58, 66, 74-107, and 111-119 were at least 6.0.

The pIC$_{50}$ values in the thio-PAF assay for examples 1-5, 7, 10, 13, 15, 16, 21, 27-30, 33, 34, 37, 38, 40, 42, 53, 55, 56, 58, 75, 76, 79-84, 88, 89, 91-101, 104-107, and 112-119 were at least 7.0.

E. METHODS OF USE

The compounds of this invention are inhibitors of Lp-PLA$_2$. Therefore, these compounds may be used in therapy, for example, in the treatment of disorders associated with the activity of Lp-PLA$_2$. Accordingly, another aspect of the invention is directed to methods of treating conditions associated with the activity of Lp-PLA$_2$. As will be appreciated by those skilled in the art, a particular condition or its treatment may involve one or more underlying mechanisms associated with Lp-PLA$_2$ activity, including one or more of the mechanisms described herein.

In some embodiments, an inhibitor of Lp-PLA$_2$ according to the invention may be used in treating any of the disorders disclosed in the following published patent applications: WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, WO08/048866, WO05/003118 CA 2530816A1), WO06/063811, WO06/063813, WO 2008/141176, JP 200188847, US 2008/0279846 A1, US 2010/0239565 A1, and US 2008/0280829 A1.

In certain embodiments, the compounds of this invention may be used to treat any diseases that involve endothelial dysfunction, for example, atherosclerosis, (e.g. peripheral vascular atherosclerosis and cerebrovascular atherosclerosis), diabetes, hypertension, angina pectoris and after ischaemia and reperfusion.

In certain embodiments, the compounds of the present invention may be used to treat any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischaemia, reperfusion injury, sepsis, and acute and chronic inflammation.

In certain embodiments, the compounds of the present invention may be used to treat diseases that involve activated monocytes, macrophages or lymphocytes, as all of these cell types express Lp-PLA$_2$ including diseases involving activated macrophages such as M1, dendritic and/or other macrophages which generate oxidative stress; exemplary disorder includes, but are not limited to, psoriasis, rheumatoid arthritis, wound healing, chronic obstructive pulmonary disease (COPD), liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In certain embodiments, the present invention provides methods of treating a disease associated with the activity of Lp-PLA$_2$, which comprises treating a subject in need thereof with a therapeutically effective amount of an inhibitor of Lp-PLA$_2$. The disease may be associated with the increased involvement of monocytes, macrophages or lymphocytes; with the formation of lysophosphatidylcholine and oxidized free fatty acids; with lipid oxidation in conjunction with Lp-PLA$_2$ activity; or with endothelial dysfunction.

In other embodiments, the compounds of the invention may be used for the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiment, the compounds of the present invention may be used to treat the disease described herein in combination with an anti-hyperlipidaemic, anti-atherosclerotic, anti-diabetic, anti-anginal, anti-inflammatory, or anti-hypertension agent or an agent for lowering Lipoprotein (a) (Lp(a)). Examples of the above include, but are not limited to, cholesterol synthesis inhibitors such as statins, anti-oxidants such as probucol, insulin sensitizers, calcium channel antagonists, and anti-inflammatory drugs such as non-steroidal anti-inflammatory Drugs (NSAIDs). Examples of agents for lowering Lp(a) include the aminophosphonates described in WO 97/02037, WO 98/28310, WO 98/28311 and WO 98/28312.

In one embodiment, the compounds of the present invention may be used with one or more statins. The statins are a well-known class of cholesterol lowering agents and include atorvastatin, simvarstatin, pravastatin, cerivastatin, fluvastatin, lovastatin and rosuvastatin. The two agents may be administered at substantially the same time or at different times, according to the discretion of the physician.

In a certain embodiment, the compounds of the present invention may be used with an anti-diabetic agent or an insulin sensitizer. In one embodiment, a compound of the present invention may be used with PPAR gamma activators, for instance GI262570 (GlaxoSmithKline) and the glitazone class of compounds such as rosiglitazone, troglitazone and pioglitazone.

In one embodiment, the compounds of the present invention may be used to treat a neurodegeneration disease in a subject. The methods comprise administering to a subject in need thereof a pharmaceutical composition comprising an agent that inhibits the activity of Lp-PLA$_2$. Exemplary neurodegeneration diseases include, but are not limited to, Alzheimer's disease, vascular dementia, Parkinson's disease and Huntington's disease. In a certain embodiment, the neurodegeneration disease described herein is associated with an abnormal blood brain barrier. In one embodiment, the subject which is administered an agent that inhibits the activity of Lp-PLA$_2$ is a human.

In one embodiment, the present invention provides methods of treating a subject with or at risk of vascular dementia. The methods comprise administering to the subject a pharmaceutical composition comprising a safe and effective amount of a compound of the present invention. In a certain embodiment, the vascular dementia is associated with Alzheimer's disease.

In certain embodiments, the present invention provides methods of treating a neurological disorder associated with an abnormal blood brain barrier (BBB) function, inflammation, and/or microglia activation in a subject in need thereof. The methods comprise administering to the subject a safe and effective amount of a compound of the present invention. In a further embodiment, the abnormal BBB is a permeable BBB. In yet a further embodiment, the disease is a neurodegeneration disease. Such neurodegeneration diseases are, for example, but are not limited to, vascular dementia, Alzheimer's disease, Parkinson's disease and Huntington's disease. In one embodiment, the present invention provides methods of treating disease associated with a subject with blood brain barrier (BBB) leakage. Exemplary diseases include, but are not limited to, brain hemorrhage, cerebral amyloid angiopathy. In one embodiment, the neurodegeneration disease is Alzheimer's disease. In a certain embodiment, the neurodegeneration disease is vascular dementia. In one embodiment, the neurodegeneration disease is multiple sclerosis (MS).

In certain embodiments, the present invention provides methods of decreasing beta amyloid, referred to as "Aβ" accumulation in the brain of a subject. The methods comprise administering to a subject in need thereof a pharmaceutical composition comprising a safe and effective amount of a compound of the present invention. In a further embodiment, the beta amyloid is Abeta-42.

In certain embodiments, when a subject is administered a safe and effective amount of a compound of the present invention, the methods may further comprise administering to the subject another therapeutic agent that may be useful in treating the neurodegenerative disease for which the subject is being treated, or that may be a co-morbidity. For example, when the neurodegenerative disease is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation.

In certain embodiments, the present invention relates to methods of treating metabolic bone diseases by administering to the subject in need thereof a safe and effective amount of a compound of the present invention. Exemplary metabolic bone diseases include, diseases associated with loss of bone mass and density including, but are not limited to, osteoporosis and osteopenic related diseases. Exemplary osteoporosis and osteopenic related diseases include, but are not limited to, bone marrow abnormalities, dyslipidemia, Paget's diseases, type II diseases, metabolic syndrome, insulin resistance, hyperparathyroidism and related diseases. In a further embodiment, the subject in need thereof is a human.

It is believed that methods of preventing osteoporosis and/or osteopenic diseases described herein may be affected by inhibiting the expression of Lp-PLA$_2$ and/or inhibiting the protein activity of Lp-PLA$_2$. Accordingly, some embodiments of the present invention provide methods for inhibiting Lp-PLA$_2$ by blocking enzyme activity. In a further embodiment, methods for inhibiting Lp-PLA$_2$ by reducing and/or down-regulating the expression of Lp-PLA$_2$ RNA are provided. In a further embodiment, preventing and/or reducing loss of bone mass and/or loss of bone density leads to preventing or reducing symptoms associated with metabolic bone diseases such as osteoporosis and/or osteopenic diseases.

In certain embodiments, the methods further comprise administering to a subject in need thereof additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene, a selective estrogen modulator (SERM), estrogen therapy, hormone replacement therapy (ET/HRT) and teriparatide) may be used.

One aspect of the present invention provides methods for treating eye diseases by administering a safe and effective amount of a compound of the present invention. Eye diseases applicable in the present invention may be associated with the breakdown of the inner blood-retinal barrier (iBRB). Exemplary eye diseases relate to diabetic eye diseases and disorders, which includes macular edema, diabetic retinopathy, and the like. Further, in one embodiment, the present invention relates to methods for treating eye diseases by administering a compound of the present invention to inhibit Lp-PLA$_2$. Exemplary eye diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like.

Further, some embodiments of the present invention provide methods for treating diabetic macular edema in a subject. The method comprises administering to a subject in need thereof a safe and effective amount of a compound of the present invention.

In certain embodiments, the present invention provides methods of treating a subject with or at risk of macular edema. The methods comprise administering to the subject a safe and effective amount of a compound of the present invention. In a further embodiment, the macular edema is associated with diabetic eye disease, for example, diabetic retinopathy. In yet a further embodiment, the macular edema is associated with posterior uveitis.

In certain embodiments, the present invention provides methods of treating glaucoma or macular degeneration. The methods comprise administering to the subject a safe and effective amount of a compound of the present invention.

In one embodiment, the present invention provides methods of treating a disease associated with the breakdown of the inner blood-retinal barrier in a subject in need thereof. The methods comprise administering to the subject a safe and effective amount of a compound of the present invention.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. The present invention relates to methods for treating posterior uveitis or any of these systemic inflammatory diseases by administering a safe and effective amount of a compound of the present invention.

It is believed that Lp-PLA$_2$ inhibitors may have beneficial effects on indications associated with M1/M2 macrophage polarization. The belief is based on the following studies. A study was carried out by GSK to investigate the relationship between M1/M2 macrophage polarization and different diseases. 94 human markers described in Martinez F O et al., which distinguished M1 and M2 phenotypes was used against a GSK subscribed GeneLogic database. (See Martinez F O et al. (2006) J Immunol 177, 7303-7311.) The Connectivity Map methodology described in Lamb J et al. was used to identify the fraction of samples in each disease state having expression characteristics consistent with a M1-favoring or M2-favoring macrophage population. (See Lamb J et al. (2006) Science 313, 1929-1935) (PMID 17008526)). The study showed that liver cirrhosis, skin psoriasis, atopic dermatitis, pulmonary emphysema, chronic pancreatitis, chronic gastritis, and aortic aneurysm have M1/M2 imbalance.

A further study was carried out to study the impact of Lp-PLA$_2$ inhibitors on modulating M1/M2 imbalance. In this study, rats were induced to develop experimental autoimmune encephalomyelitis (EAE) by immunization with myelin basic protein (MBP) antigen and treated with a known Lp-PLA$_2$ inhibitor: 5-((9-Methoxy-4-oxo-6,7-dihydro-4H-pyrimido[6,1-a]isoquinolin-2-yl)oxy)-2-(3-(trifluoromethyl)phenoxy)benzonitrile (See PCT application no. PCT/CN2011/001597). In this preventive treatment model, the compound was administered at day 0 (day of immunization) and continued to administer until day 22. The study lasted for 25 days. Rats were subsequently monitored for symptoms of EAE. Rats were immunized with MBP to develop EAE and symptoms were monitored daily. Plasma Lp-PLA$_2$ activity, OxLDL, and LysoPC concentration were determined at different time points through the course of EAE. The results showed that plasma Lp-PLA$_2$ activity, OxLDL, and LysoPC concentrations increased as the clinical EAE disease progressed in the model, which indicates that they played a role in the pathology development. Lp-PLA$_2$ inhibitor treatment led to reduction in clinical disease associated with decreased Lp-PLA$_2$ activity and LysoPC levels in rat EAE plasma. Hence, inhibition of Lp-PLA$_2$ activity is beneficial in ameliorating disease in the rat EAE model.

Ex vivo analysis of proinflammatory (M1) and anti-inflammatory (M2) markers in control and compound treated EAE rats. Splenic macrophages were harvested at day 13 post MBP-immunization and assayed for expression of a variety of markers by realtime PCR. CNS infiltrating cells were harvested and macrophages were analyzed for expression of M1 and M2 markers by realtime PCR. Treatment with compound resulted in the decrease in M1 markers and increase in M2 markers, which potentially indicated the possibility of anti-inflammation and tissue repair.

Therefore, in certain embodiments, the present invention provides methods of treating disease associated with macrophage polarization, for example, M1/M2 macrophage polarization. Exemplary diseases associated with macrophage polarization include, but are not limited to, liver cirrhosis, skin psoriasis, atopic dermatitis, pulmonary emphysema, chronic pancreatitis, chronic gastritis, aortic aneurysm, atherosclerosis, multiple sclerosis, and other autoimmune diseases that are associated with macrophage polarization.

One aspect of the present invention provides the use of a compound of the present invention for the preparation of a medicament for carrying out a method described herein. Another aspect of the present invention provides a compound of the present invention for use in carrying out methods of treatment described herein. A further aspect of the present invention provides a compound described herein or a pharmaceutically acceptable salt thereof, for use in therapy.

F. COMPOSITION

The compounds of the present invention may be formulated into pharmaceutical compositions prior to administration to a subject. Accordingly, one aspect of the invention is directed to pharmaceutical compositions comprising a compound of the invention and one or more pharmaceutically-acceptable excipients. In accordance with another aspect of the invention, a process is provided for the preparation of a pharmaceutical composition including admixing a compound of the Formula (I) Formula (IA), Formula (IB), Formula (IC), or salts thereof, solvates etc thereof, with one or more pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the condition being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

An effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of present invention for the treatment of anemia will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. An effective amount of a salt or solvate, etc., may be determined as a proportion of the effective amount of the compound of Formula (I), Formula (IA), Formula (IB), or Formula (IC), per se. It is envisaged that similar dosages would be appropriate for treatment of the other conditions referred to above.

The pharmaceutical compositions of the invention may contain one or more compounds of the invention. In some embodiments, the pharmaceutical compositions may contain more than one compound of the invention. For example, in some embodiments, the pharmaceutical compositions may contain two or more compounds of the invention. In addition, the pharmaceutical compositions may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically-acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any methods known in the art of pharmacy, for example by bringing into association a compound of Formula (I), Formula (IA), Formula (IB), or Formula (IC) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate carrying or transporting the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In certain embodiment, the present invention is directed to a pharmaceutical composition comprising 0.01 to 1000 mg of one or more compounds described herein or a pharmaceutically acceptable salt thereof and 0.01 to 5 g of one or more pharmaceutically acceptable excipients.

In another embodiment, the present invention is directed a pharmaceutical composition for the treatment of neurodegeneration disease comprising a compound described herein or a pharmaceutically acceptable salt thereof.

What is claimed is:

1. A compound of Formula (I) or a pharmaceutically acceptable salt thereof,

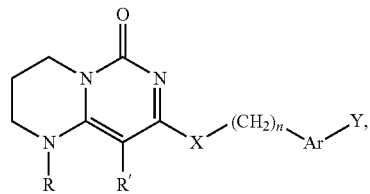

Formula (I)

wherein:
R is H or $C_1$-$C_6$alkyl,
R' is H, halo, or $C_1$-$C_6$alkyl,
X is —O—, —NH—, —N($C_1$-$C_6$alkyl)-, —S— or —$CH_2$—,
n is 0, 1, 2 or 3, or when X is —$CH_2$—, n is 1 or 2,
Ar is phenyl or heteroaryl, either of which is unsubstituted or substituted with one or more groups selected from the group consisting of CN, halo, OH, —$NH_2$, —$NHR_1$, —$NR_1R_2$, $C_1$-$C_6$alkyl, $C_1$-$C_6$alkoxy, and $C_1$-$C_6$haloalkyl, and
Y is absent or —O—Ar', —NH—Ar', —N($C_1$-$C_6$alkyl)-Ar', or —($CH_2$)—Ar',
wherein Ar' is phenyl or heteroaryl, either of which is unsubstituted or substituted with one or more groups selected from the group consisting of CN, halo, OH, —$NH_2$, —$NHR_1$, —$NR_1R_2$, $C_1$-$C_6$alkyl, $C_1$-$C_6$alkoxy, and $C_1$-$C_6$haloalkyl, and
each occurrence of $R_1$ and $R_2$ is independently $C_1$-$C_6$alkyl.

2. The compound according to claim 1, wherein the compound has the structure of Formula (IB), Formula (IB)

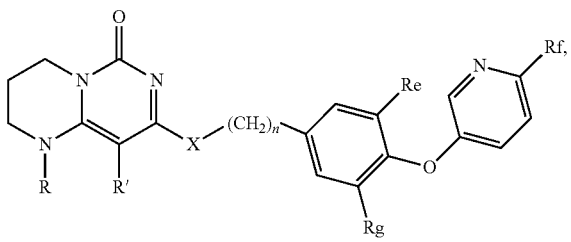

wherein Re, Rf and Rg are independently selected from the group consisting of hydrogen, CN, halo and $CF_3$, or a pharmaceutically acceptable salt thereof.

3. The compound according to claim 2 having the structure of

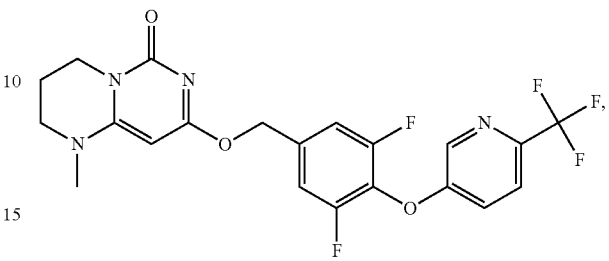

or a pharmaceutically acceptable salt thereof.

4. The compound according to claim 1, wherein the compound has the structure of Formula (IC), Formula (IC)

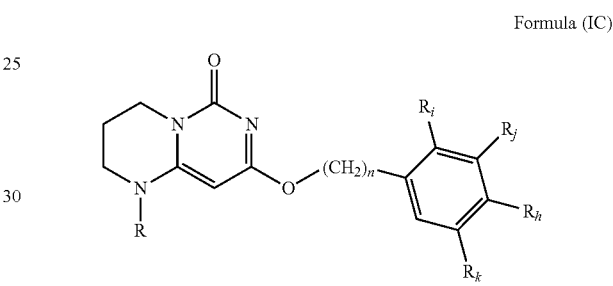

wherein
R is $CH_3$, or iso-propyl,
n is 1 or 2,
Ri is selected from the group consisting of F, Cl and H,
Rj is selected from the group consisting of H, F, Cl, $CF_3$, CN and $OCH_3$,
Rh is selected from the group consisting of H, F, Cl, CN, and $CF_3$, and
Rk is selected from the group consisting of H, F and CN, or a pharmaceutically acceptable salts thereof.

5. The compound according to claim 4 having the structure of

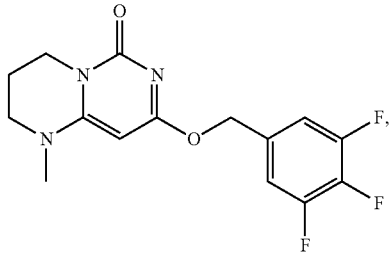 [SMILES: CN1CCCn2c1cc(OCc1cc(F)c(F)c(F)c1)nc2=O]

or a pharmaceutically acceptable salt thereof.

6. The compound according to claim 1, wherein R is $CH_3$.
7. The compound according to claim 1, wherein R' is H.
8. The compound according to claim 1, wherein X is —O—.
9. The compound according to claim 1, wherein n is 1 or 2.
10. The compound according to claim 1, wherein Ar is unsubstituted phenyl, or phenyl substituted with one or more groups selected from the group consisting of CN, F, $CF_3$, Cl, OMe, and $CH_3$, or Ar is pyridinyl or thiophenyl, either of which is unsubstituted or substituted with one or more F.

11. The compound according to claim 1, wherein Y is absent or Y is —O—Ar', wherein Ar' is unsubstituted phenyl, or phenyl substituted with one or more groups selected from the group consisting of $CF_3$, F, Cl, CN, and $CH_3$, or Ar' is pyridinyl or pyrimidinyl, either of which is unsubstituted or substituted with one or more groups selected from the group consisting of $CF_3$ and $CH_3$.

12. A pharmaceutical composition comprising a compound of Formula (I) according to claim 1 or a pharmaceutically acceptable salt thereof, and one or more pharmaceutically acceptable excipients.

* * * * *